United States Patent
Son et al.

(10) Patent No.: US 9,051,605 B2
(45) Date of Patent: Jun. 9, 2015

(54) MAGNETIC BEAD QUANTUM DOT NANOPARTICLE ASSAY

(75) Inventors: Ahjeong Son, Aurbun, AL (US); Yeomin Yoon, Irmo, SC (US)

(73) Assignees: AUBURN UNIVERSITY, Auburn, AL (US); UNIVERSITY OF SOUTH CAROLINA, Columbia, SC (US)

( * ) Notice: Subject to any disclaimer, the term of this patent is extended or adjusted under 35 U.S.C. 154(b) by 0 days.

(21) Appl. No.: 13/560,162

(22) Filed: Jul. 27, 2012

(65) Prior Publication Data

US 2013/0029333 A1   Jan. 31, 2013

Related U.S. Application Data

(60) Provisional application No. 61/574,249, filed on Jul. 29, 2011.

(51) Int. Cl.

| | |
|---|---|
| *C12Q 1/68* | (2006.01) |
| *C12P 19/34* | (2006.01) |
| *C07H 21/02* | (2006.01) |
| *C07H 21/04* | (2006.01) |
| *G01N 21/64* | (2006.01) |
| *B82Y 15/00* | (2011.01) |
| *B82Y 30/00* | (2011.01) |

(52) U.S. Cl.
CPC .......... *C12Q 1/6813* (2013.01); *G01N 21/6428* (2013.01); *G01N 2021/6417* (2013.01); *G01N 2021/6432* (2013.01); *G01N 2201/0221* (2013.01); *B82Y 15/00* (2013.01); *B82Y 30/00* (2013.01)

(58) Field of Classification Search
CPC .. C12Q 1/6813; C12Q 1/6816; C12Q 1/6825; C12Q 1/6832; C12Q 1/3876
USPC ................... 435/6.1, 6.11, 91.1; 436/94, 501; 536/23.1, 24.3, 24.33; 977/704, 705, 977/728, 742, 752, 773, 774, 876
See application file for complete search history.

(56) References Cited

U.S. PATENT DOCUMENTS

| | | |
|---|---|---|
| 6,361,944 B1 * | 3/2002 | Mirkin et al. ................ 435/6.11 |
| 7,575,934 B2 | 8/2009 | Atwood |
| 2008/0135490 A1 | 6/2008 | Li et al. |
| 2011/0065086 A1 | 3/2011 | Bruno |
| 2012/0196302 A1 | 8/2012 | Lai et al. |

OTHER PUBLICATIONS

Bruno et al., Plastic-Adherent DNA Aptamer-Magnetic Bead and Quantum Dot Sandwich Assay for Campylobacter Detection. J. Fluoresc., 19, 427-435, 2009.*
Chi et al., A quantum dot-aptamer beacon using a DNA intercalating dye as the FRET reporter: Application to label-free thrombin detection. Biosensors and Bioelectronics, 26, 3346-3352, Mar. 2011.*
"DNA" from Wikipedia, the free encyclopedia. Printed on May 30, 2014.*

* cited by examiner

*Primary Examiner* — Frank Lu
(74) *Attorney, Agent, or Firm* — Thomas Horstemeyer, LLP

(57) ABSTRACT

The present disclosure includes a magnetic bead (MB) quantum dot (QD) nanoparticle assay for detecting, capturing, separating, and/or quantifying a target in a sample.

9 Claims, 40 Drawing Sheets

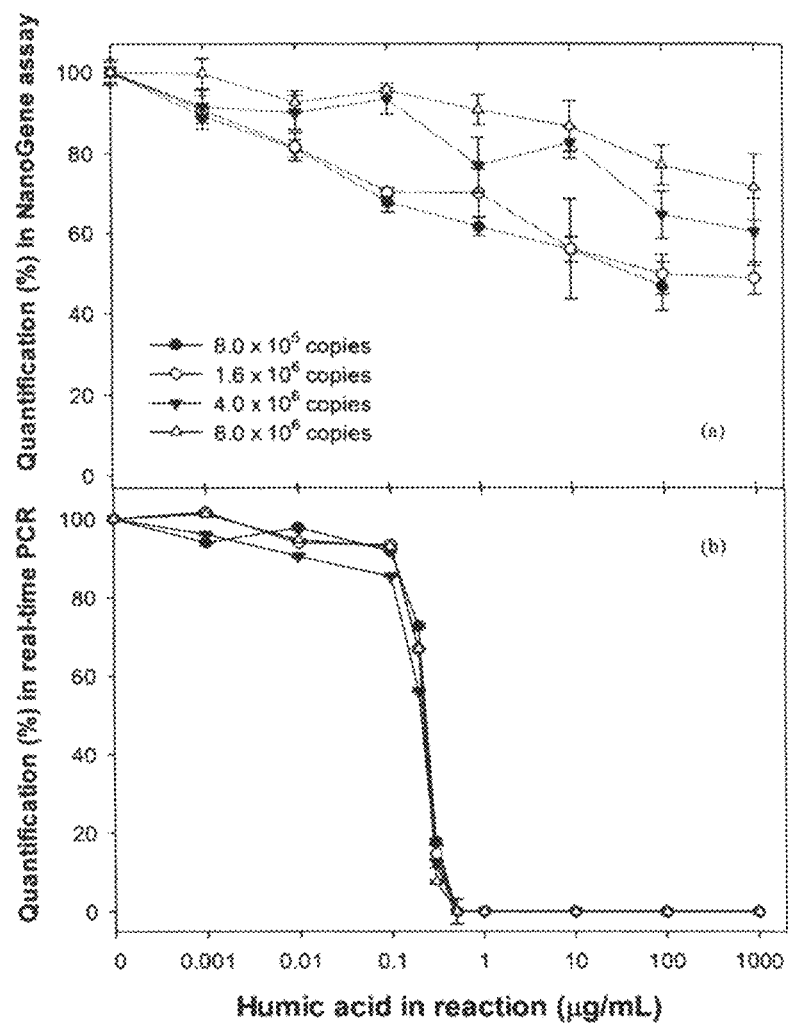
FIGS. 26A-B

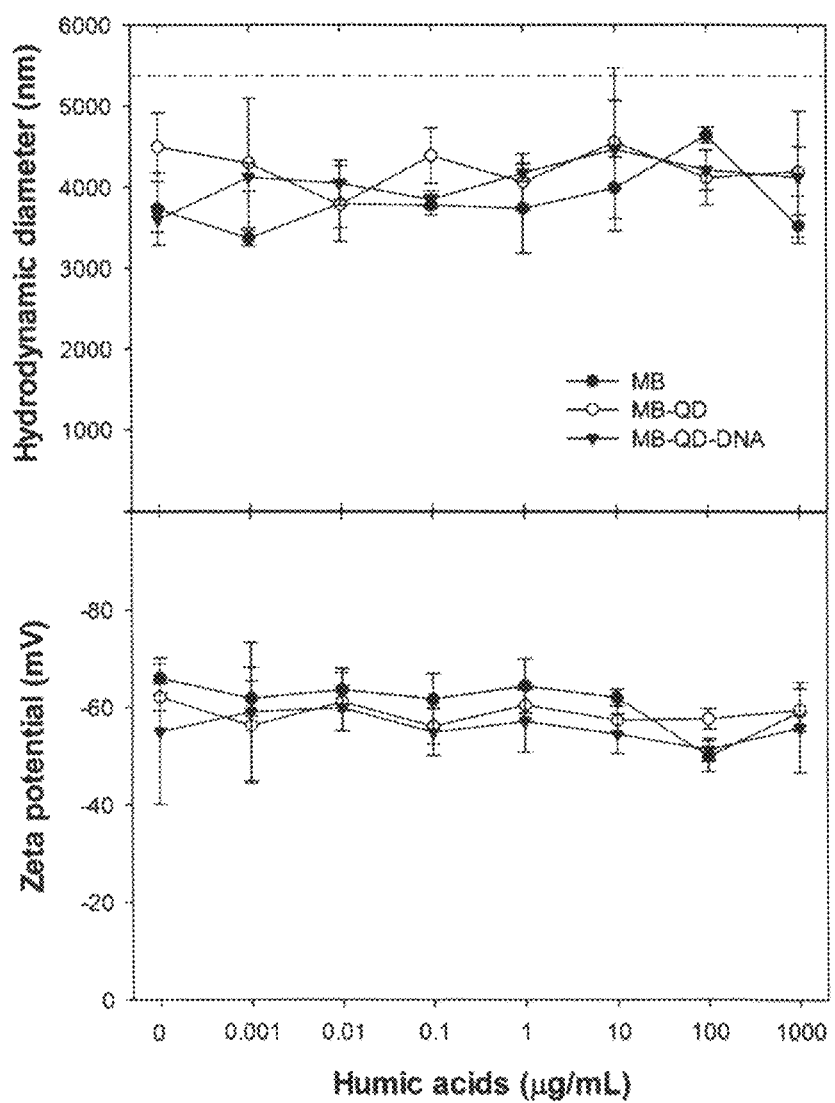
FIGS. 28A-B

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Chemically synthesized Probe DNA

```
<400> SEQUENCE: 1
cggataagac ttcggctaaa                                              20

<210> SEQ ID NO 2
<211> LENGTH: 20
<212> TYPE: DNA
<213> ORGANISM: Artificial Sequence
<220> FEATURE:
<223> OTHER INFORMATION: Chemically synthesized 1 bp mismatched probe
      DNA

<400> SEQUENCE: 2
cttataccgc gaccgtgaaa                                              20

<210> SEQ ID NO 3
<211> LENGTH: 20
<212> TYPE: DNA
<213> ORGANISM: Artificial Sequence
<220> FEATURE:
<223> OTHER INFORMATION: Chemically synthesized signaling probe DNA

<400> SEQUENCE: 3
cttataccgc gacggtgaaa                                              20

<210> SEQ ID NO 4
<211> LENGTH: 55
<212> TYPE: DNA
<213> ORGANISM: Escherichia coli

<400> SEQUENCE: 4
accgtcgcgg tataagtaat ggtatcggcg ttatccgctt tagccgaagt cttat       55

<210> SEQ ID NO 5
<211> LENGTH: 20
<212> TYPE: DNA
<213> ORGANISM: Artificial Sequence
<220> FEATURE:
<223> OTHER INFORMATION: Chemically synthesized forward primer

<400> SEQUENCE: 5
ggcggataag acttcggcta                                              20

<210> SEQ ID NO 6
<211> LENGTH: 20
<212> TYPE: DNA
<213> ORGANISM: Artificial Sequence
<220> FEATURE:
<223> OTHER INFORMATION: Chemically synthesized 1 bp mismatched forward
      primer

<400> SEQUENCE: 6
ggcggataac acttcggcta                                              20

<210> SEQ ID NO 7
<211> LENGTH: 20
<212> TYPE: DNA
<213> ORGANISM: Artificial Sequence
<220> FEATURE:
<223> OTHER INFORMATION: Chemically synthesized reverse primer

<400> SEQUENCE: 7
cgttttggca ctatttgccc                                              20
```

MAGNETIC BEAD QUANTUM DOT NANOPARTICLE ASSAY

CROSS-REFERENCE TO RELATED APPLICATION

This application claims priority to U.S. provisional application entitled "Method for Detection and Quantification of Carbon Nanotubes in Water Containing Other Carbon Compounds," having Ser. No. 61/574,249 filed on Jul. 29, 2011, which is entirely incorporated herein by reference.

STATEMENT REGARDING FEDERALLY SPONSORED RESEARCH OR DEVELOPMENT

This invention was made with government support under the Auburn University start-up fund and U.S. Geological Survey Section 104, Water Resources Research Institute Program, USGS-06HQGR0070 and the National Science Foundation Career Funding No. 1054768. The government has certain rights in the invention.

BACKGROUND

The availability of nanostructured materials has enabled numerous sensing technologies to leverage their advanced material properties in order to significantly improve performance and robustness. Bioassays using nanoparticle labels have the potential to be implemented as part of a miniaturized, portable device for the in-situ monitoring of bacteria. Despite the efforts in developing nanoparticle based assays to advance bioanalytics, the related DNA detection technologies are relatively recent and are still in the early stage of development.

Several studies project the production of CNTs at millions of tons in 2010 and the worldwide market for nanoproducts as $1 trillion by 2015. The escalating pace, scope, and scale at which engineered nanomaterials such as CNTs are being produced and used in numerous aspects of our lives parallel that of asbestos more than a century ago. Just as the newly industrialized world in the 1800s was mesmerized by the versatility of asbestos, the past few decades have witnessed burgeoning interest in the unique properties of engineered nanomaterials. As history has a tendency to repeat itself, it is not surprising that health implications of CNTs have begun to surface. Potential health risks of CNTs have been demonstrated in mice, rats, pigs, and human skin, all of which have experienced consequences of various diseases or cancer. Unfortunately, there are no CNT specific detection and quantification technologies developed for field studies on potential CNT contaminated sites.

SUMMARY

Embodiments of the present disclosure, in one aspect, relate to a magnetic bead (MB) quantum dot (QD) nanoparticle assay.

Briefly described, an embodiment of the present disclosure includes a method of analyzing at least one target in a sample comprising a MB, a dual fluorescent nanoparticle, a probe DNA and a capturing DNA based inhibitor-resistant and interference-resistant assay, where the at least one target is selected from the group consisting of: a single wall carbon nanotube (CNT), a multi-wall CNT, a genomic substance, a single strand DNA, a double strand DNA, and a combination thereof.

In an embodiment of the present disclosure, a method of rapidly analyzing at least one target gene in a sample comprises encapsulating an aminated magnetic bead (MB) with a first carboxyl quantum dot (QD) nanoparticle to form an MB-QD particle complex; conjugating a capturing probe DNA to the MB-QD particle complex; labeling a signaling probe DNA with a second carboxyl QD nanoparticle; hybridizing the target genomic DNA (gDNA) with the capturing probe DNA conjugated with MB-QD and the signaling probe DNA conjugated with QD; separating the DNA particle hybrids by magnetic application; and detecting and quantifying the target gene via fluorescence measurement.

In another embodiment, a method of analyzing at least one carbon nanotube (CNT) in a sample comprises encapsulating a magnetic bead (MB) with a first carboxyl quantum dot (QD) nanoparticle to form an MB-QD particle complex; conjugating a capturing probe DNA to the MB-QD particle complex; labeling a signaling probe DNA with a second carboxyl QD nanoparticle; hybridizing the at least one target CNT with the capturing probe DNA conjugated with MB-QD and the signaling probe DNA conjugated with QD; extracting the MB-CNT complexes via a magnetic field; and quantifying the at least one CNT using fluorescence measuring.

Embodiments of the present disclosure include a structure comprising a capturing probe DNA covalently conjugated with at least one magnetic bead (MB) encapsulated with at least one carboxyl quantum dot (QD) nanoparticle linked to a signaling probe DNA conjugated with at least one QD nanoparticle via sandwich hybridization with a target DNA.

In another embodiment, a structure comprises a carbon nanotube (CNT) wrapped with a first and a second ssDNA, where the first ssDNA is labeled with a magnetic fluorescent bead or MB-QD complex, and where the second ssDNA is labeled with a fluorophore or QD.

Embodiments of the present disclosure also include a portable device comprising an automated portable system contained within a structure comprising: reagents, a sample loader, a fluidic mixer, an inline magnetic trap, and a spectrofluorometer, where the reagents are prepared and stored at about ambient temperature for at least about six months prior to use; the sampler loader draws the sample and reagents into the fluidic mixer; the fluidic mixer mixes the injected reagents and sample and performs hybridization in about 45 minutes at about ambient temperature or about ambient room temperature; the inline magnetic trap captures magnetic bead (MB) and DNA conjugate with an actuatable magnet as the hybridized reagents and sample flow through it; and the spectrofluorometer measures optical intensity at the corresponding wavelengths of the magnetically captured MB and DNA conjugates; and where the method results are obtained within about 45 minutes.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 26A-B are graphs that illustrate a comparison of the quantification of the eaeA gene of *E. coli* O157:H7 by (A) NanoGene and (B) qPCR assays in the presence of various concentrations of humic acids. Four tested target gDNAs for both NanoGene and qPCR assays were identical to $8.0 \times 10^5$ through $8.0 \times 10^6$ eaeA gene copy numbers of *E. coli* O157:H7. The signal and error bar represent the mean and the standard deviation, respectively, based on five measurements. Note that this caption also applies for the following FIGS. 28-31.

FIGS. 28A-B are graphs that illustrate particle aggregation effect by humic acids. (A) Hydrodynamic diameters and (B) zeta potential (surface charge) distribution the particle complex of the NanoGene assay (i.e., MB, MB-QD, and MB-QD-DNA) in the presence of varying humic acids.

DETAILED DESCRIPTION

Figure 1:
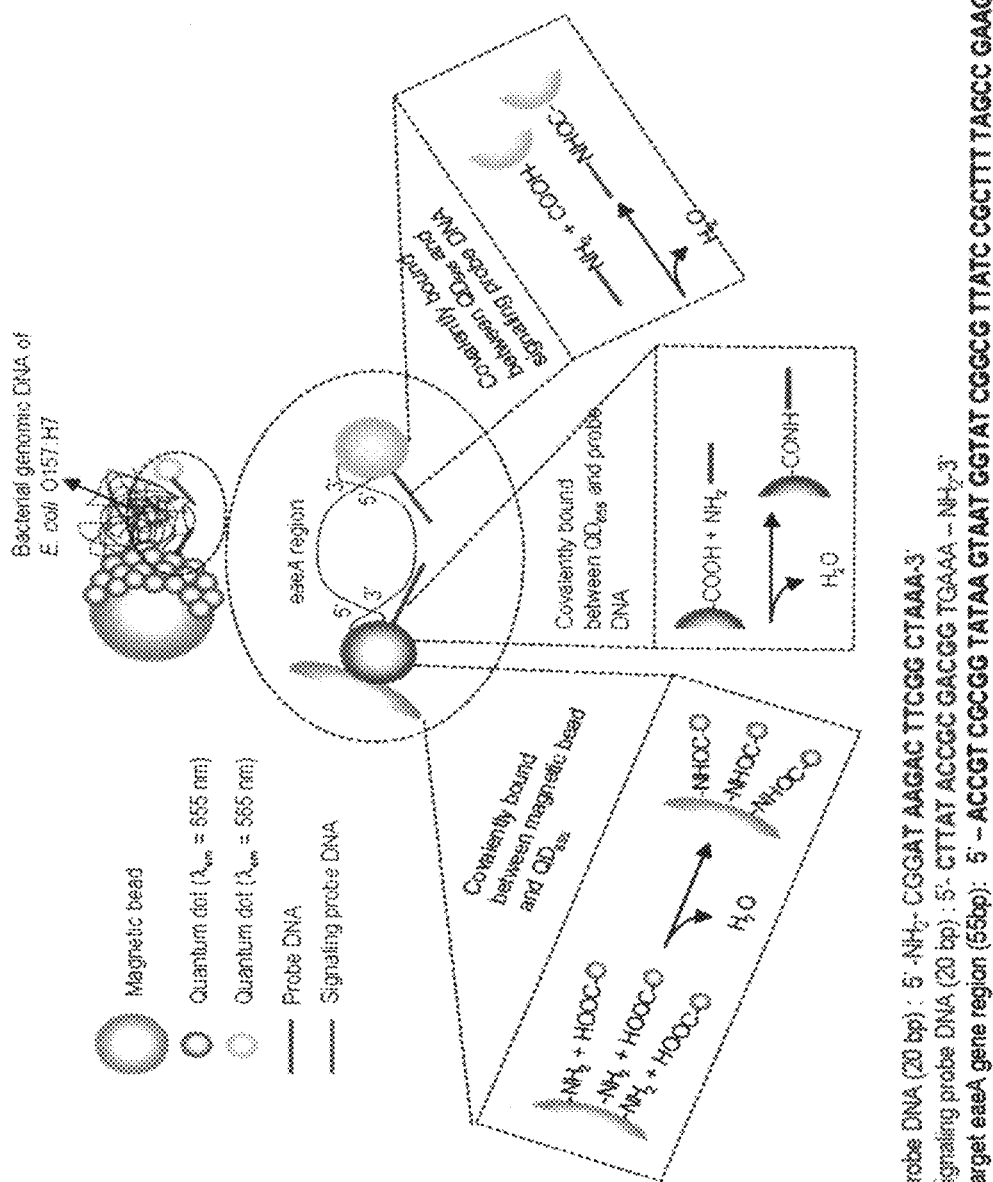
FIG. 1 is a schematic diagram that illustrates an embodiment of the gene quantification assay using magnetic beads and a set of quantum dot nanoparticles (i.e., $QD_{655}$ as an internal standard and $QD_{565}$ as a label). Probe DNA, as shown in FIG. 1, corresponds to SEQ ID NO: 1. Signaling probe DNA, as shown in FIG. 1, corresponds to SEQ ID NO: 3. Target eaeA region, as shown in FIG. 1, corresponds to SEQ ID NO: 4.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

The terms "quantum dot" (QD) and "nanoparticle" (NP) are used interchangeably herein. Both terms refers to semiconductor or insulator nanoparticle with or without one or more dopants. When doped with more than one dopant, the nanoparticle is sometimes called "co-doped". These nanoparticles are also known as nanocrystals, or artificial atoms, which are crystals that contain about 100 to 500,000 atoms or have a diameter of about 1-250 nm. In an embodiment, NP can be a sphere having a diameter of about 1-250 nm. In an embodiment, NP can be a nanorod with diameters of about 1-100 nm and lengths between about 2× and 1000× the diameter. In an embodiment, NP can be luminescent, i.e., emits electromagnetic radiation commonly UV or within the visible spectrum upon stimulation e.g., from a light source of appropriate wavelength, or from ionizing radiation, or neutrons. Scintillation can be understood as the generation of UV or visible light due to irradiation of ionizing radiation, or neutrons. The terms "luminescent" and "scintillation" and other related terms are used interchangeably herein. In an embodiment, NPs are non-luminescent and the matrix containing the NPs is luminescent. In an embodiment, there is more than one type of NP. In an embodiment, at least one type of NP and the matrix are luminescent. The shape of the NP may be complex, such as platelets, faceted particles, cylinders, tetrapods, stars, and the like. Luminescent NPs may have high photon quantum yields, which makes them particularly useful for optical applications. Semiconductor NPs are fluorophores that fluoresce by forming excitons, which can be thought of as the excited state of traditional fluorophores, but may have much longer lifetimes of up to about 200 nanoseconds. This property provides NPs with low photobleaching. Doped insulators fluoresce by recombination of charge carrier at the dopant atom and exhibit lifetimes of less than 1 nanosecond to greater than 5 milliseconds. Rather than luminesce directly, one or more dopants can also be added to compensate charge imbalance due to other dopants or defects, and/or to promote energy transfer to the luminescent center. The energy level of the quantum states of NPs with dimensions less than the Bohr radius can be controlled by changing the size and shape of the NP and the depth of the NPs' potential, and are called quantum dots (QDs). One of the optical features of semiconductor excitonic NPs is coloration, which is determined by the size and composition of the QD. As the dimension of the QD increases approaching the Bohr radius, the color is red-shifted, i.e. exhibits a longer wavelength of the fluorescence. The smaller QD's with dimensions less than the Bohr radius may exhibit a blue-shift towards shorter fluorescence wavelength. The magnitude of the bandgap (in some cases less the excitonic binding energy) determines the energy and hence the color of the fluoresced light. For NP's less than the Bohr radius, the bandgap is inversely proportional to the square of the size of the semiconductor NP. For doped insulators and semiconductors with larger radii, the color of the fluoresced light is equal to the difference between ground and/or lower level excited quantum states and upper level excited states of the dopant(s) that may or may not be a function of the NP size. Larger NPs have more closely spaced energy levels, thus allowing the NP to absorb photons with lower energy, e.g., photons with longer wavelengths.

As mentioned above, NPs can include, but are not limited to, luminescent semiconductor QDs. In general, NP's include a core material and a capping (also called a shell) material, however, uncapped NP's can be used as well. The "core" is a semiconductor or doped or undoped insulator nanoparticle with dimensions of about 1 to 250 nm. While any core of the IIB-VIA, IIIA-VA, or IVA-IVA, IVA-VIA, IB-IIIA-VIA semiconductors or doped or undoped insulator can be used in the context of the present disclosure, the core may or may not be a luminescent NP, whose luminance may be increased by a capping layer. A IIB-VIA semiconductor is a compound that contains at least one element from Group IIB and at least one element from Group VIA of the periodic table, and so on. The core can include two or more elements. In an embodiment, the core of the nanoparticles can also be a transition metal oxide or lanthanide metal oxide NP doped with rare earth or transition metal ions, or a combination thereof. In another embodiment, the core of the NP is a Group IA or IIA or solid solutions between Group IA elements, Group IIA elements, and combination thereof, or lanthanide metals bound to a Group VIIA halide with or without a dopant, particularly rare earth ions and transition metal ions, Ce-doped Lu, Y and Gd oxyorthosilicates, Ce-doped oxyorthosilicates made with a combination of at least two of the elements Y, Lu and Gd, Ce-doped Sr or Ba hafanate, or alloys such as $Lu_{2x}Gd_{2(1-x)}SiO_5$:Ce or $Ce_xLa_{1-x}F_3$ (x is variable from about one to zero). In one embodiment, the core is an IIB-VIA, IIIA-VA, or IVA-IVA semiconductor that can be about 1 nm to 40 nm, about 1 nm to 30 nm, about 1 nm to 20 nm, or about 1 nm to 10 nm in diameter. In another embodiment, the core can be an IIB-VIA semiconductor and can be about 2 nm to 10 nm in diameter. For example, the core can be CdS, CdSe, CdTe, ZnSe, ZnS, ZnS:Ag, ZnO:Ag, PbS, PbSe, or an alloy such as $Cd_xZn_{1-x}Se_yTe_{1-y}$, where x is a variable from one to zero and y is variable from about one to zero. In an embodiment the core is CdTe.

The "cap" or "shell" may be a semiconductor or insulator that differs from or is the same as the semiconductor or insulator of the core and binds to the core, thereby forming a surface layer on the core. A shell can differ from the core and/or other shells by means of its chemical composition, and/or the presence of one or more dopants, and/or different amounts of a given dopant. The shell typically passivates the core by having a higher band gap than the core, and having an energy offset in the top of the valence band and bottom of the conduction band such that electrons and/or holes may be confined to the core by the shell. Each shell encloses, partially (e.g., about 50% or more, about 60% or more, about 70% or more, about 80% or more, about 90% or more, about 95% or more, about 99% or more) or totally, the adjacent shell closer to the core. In one embodiment, the shell can be a IIB-VIA semiconductor of high band gap. For example, the shell can be ZnS or CdS on a core of $CdSe_yTe_{1-y}$ (y is variable from about one to zero). Other combinations of the core and shell can include, but are not limited to, the shell is ZnS when the core is CdSe or CdS, and the shell is CdS when the core is CdSe. In an embodiment, the shell may also be an organic film, such as silicones, thiophenes, trioctylphosphine, trioctylphosphine oxide, or a combination thereof. Other exemplary NP's include, but are not limited to, CdS, ZnSe, ZnS:Ag, ZnS:Cu, ZnO, CdSe, CdTe, $CdSe_xTe_{1-x}$ (x is variable from about one to zero), InAs, InP, PbTe, PbSe, PbS, HgS, HgSe, HgTe, CdHgTe, and GaAs. The thickness of the shell can be about 0.1 to 20 nm, about 0.1 to 5 nm, or about 0.1 to 2 nm covering the core. In an embodiment, the shell is CdSe. The shells can be of doped or undoped insulators, or a combination of semiconductor and doped and undoped insulators, including but not limited to $CeF_3$, $CeBr_3$, $LaBr_3$, $CaF_2$:Eu, $BaF_2$:Ce, $LaF_3$ doped with one or more lanthanide ions, Ce-doped Lu, Y and Gd oxyorthosilicates, Ce-doped oxyorthosilicates made with a combination of at least two of the elements Y, Lu and Gd, Ce-doped Sr or Ba hafanate, or alloys such as $Cd_xZn_{1-x}Se_yTe_{1-y}$, or $Lu_{2x}Gd_{2(1-x)}SiO_5$:Ce or $Ce_xLa_{1-x}F_3$ (x and y are variable from about one to zero). The core may also be a transition metal or lanthanide metal oxide, nitride, halide, or oxynitride such as LiF, LiCl, $Li_2O$, $PbF_2$, $PbCl_2$, Pb oxide, $Bi_2O_3$, $BiF_3$, $BiCl_3$, $CeF_3$, $CeBr_3$, $LaBr_3$, $CaF_2$:Eu, $BaF_2$:Ce, $LaF_3$ doped with lanthanide ions, $V_2O_3$, $Y_2O_3$, $Gd_2O_3$, doped with a lanthanide ion or undoped, Ce-doped Lu, Y or Gd oxyorthosilicate, Ce-doped Sr or Ba hafanate, $Lu_{2x}Gd_{2(1-x)}SiO_5$:Ce, $Ce_xLa_{1-x}F_3$ (x is variable from about one to zero). In another embodiment, the core may be an alkali halide, such as NaI doped with Tl, or alkaline earth halide, such as $CaF_2$ or $BaF_2$, without a dopant or with a lanthanide ion dopant, such as Eu or Ce.

The wavelength of the light emitted (e.g., color) by the QDs can be selected according to the physical properties of the NP's, such as the size, the material of the nanocrystal, and the dopant. Nanoparticles are known to emit light from about 200 nanometers (nm) to 2000 nm (e.g., UV, visible, near IR, and IR). The colors of the nanoparticles include, but are not limited to, UV, red, blue, violet, green, and combinations thereof. The color or the fluorescence emission wavelength of semiconductor QDs with a size less than the Bohr radius can be tuned continuously. The wavelength band of light emitted by the NP's may be determined by either the size of the core or the size of the core and shell, depending on the materials that make up the core and shell. The emission wavelength band can be tuned by varying the composition and the size of the NP and/or adding one or more shells around the core in the form of concentric shells. In the case of doped insulators, the color of emitted light is generally independent of the size of the quantum dot, and is mostly related to the nature of the dopant and host. However the excitation wavelength for photoluminescence may depend upon the size of the quantum dot. Frequently the quantum dot may contain intrinsic point defects and defect complexes that are optically active and result in emitted light. Emission from point defects and complexes may be influenced by the quantum dot size.

The term "nanoparticle" includes crystals with dimensions of about 1 and 250 nm (in diameter or length of the longest dimension), with spherical or more complex shapes such as platelets, faceted particles, cylinders, tetrapods, stars, etc. An embodiment of the nanoparticle can include, but are not limited to, semiconductor or doped insulator nanocrystals or undoped insulator nanocrystals. In an embodiment, the nanoparticles may have no shell, when they are sometimes called "core", or may have one or more shells, with the outer shell partially or entirely enclosing the adjacent shell closest to the core. The core and shells can have the same composition, or have different compositions, including luminescent and non-luminescent materials, and a combination thereof. The composition of the core and shells may differ by the presence or absence of one or more dopants and/or by the amount of the dopants. In an embodiment, the dopants can be, but are not limited to, lanthanides and transition metal ions, and a combination thereof. For example, nanoparticle can be, CdS, CdSe, CdTe, ZnSe, ZnS, ZnS:Ag, ZnO:Ag, PbS, PbSe, LiF, LiCl, $PbF_2$, $PbCl_2$, Pb oxide, $BiF_3$, $BiCl_3$, $Bi_2O_3$, $Li_2O$, $CeF_3$, $CeBr_3$, $LaBr_3$, $CaF_2$:Eu, $BaF_2$:Ce, $LaF_3$ doped with one or more lanthanide ions, Ce-doped Lu, Y and Gd oxyorthosilicates, Ce-doped oxyorthosilicates made with a combination of at least two of the elements Y, Lu and Gd, Ce-doped Sr or Ba hafanate, or alloys such as $Cd_xZn_{1-x}Se_yTe_{1-y}$, $Lu_{2x}Gd_{2(1-x)}SiO_5$:Ce, or $Ce_xLa_{1-x}F_3$ (x and y are variable from about one to zero). The nanoparticles can be non-luminescent or luminescent. Luminescent NPs may have high quantum yields, which make them particularly useful for optical applications.

"DNA" (deoxyribonucleic acid) generally refers to any polynucleotide. "DNA" includes, without limitation, single- and double-stranded DNA and genomic DNA; DNA that is a mixture of single- and double-stranded regions; single- and double-stranded ribonucleic acid (RNA); RNA that is mixture of single- and double-stranded regions; and hybrid molecules comprising DNA and RNA that may be single-stranded or, more typically, double-stranded or a mixture of single- and double-stranded regions. In addition, "DNA" refers to triple-stranded regions comprising RNA or DNA, or both RNA and DNA. The term "DNA" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "DNA" embraces chemically, enzymatically, or metabolically modified forms of polynucleotides as typically found in nature, as well as the chemical forms of DNA and RNA characteristic of viruses and cells. "DNA" also embraces relatively short polynucleotides, often referred to as oligonucleotides.

Discussion:

In accordance with the purpose(s) of the present disclosure, as embodied and broadly described herein, embodiments of the present disclosure, in one aspect, relate to a magnetic bead (MB) quantum dot (QD) nanoparticle assay for analyzing at least one target in a sample. In an embodiment, the method of analyzing at least one target in a sample includes detecting, capturing, identifying, separating, and/or quantifying at least one target in a sample. In another embodiment, the target is selected from carbon nanotubes (CNT) and genes.

An embodiment of the present disclosure includes a method of analyzing at least one target in a sample comprising: using an inhibitor-resistant and interference-resistant assay comprising at least one magnetic bead (MB), at least one dual fluorescent nanoparticle, at least one probe DNA, and at least one capturing DNA to detect, capture, identify, separate, or quantify the at least one target, where the at least one target is selected from the group consisting of: a single wall carbon nanotube (CNT), a multi-wall CNT, a genomic substance, a single strand DNA, a double strand DNA, and a combination thereof. In an embodiment, the assay is performed at at least about room temperature.

In an embodiment of the present disclosure, the magnetic bead(s) is comprised, at least in part, of a magnetic material. In another embodiment, the magnetic bead(s) comprise a coating. In another embodiment, the magnetic bead(s) are about 5 nm to about 500 µm in diameter.

In an embodiment of the present disclosure, the sample is selected from the group consisting of: a purified sample and an unpurified sample. In an embodiment, the unpurified sample comprises interference and inhibitory substances selected from the group consisting of: an organic compound, a non-target genomic substance, a non-target DNA, a humic acid, a mineral, an ion, a carbon chemistry based compound, graphene, a residual reagent, and a combination thereof.

In an embodiment of the present disclosure, the fluorescent nanoparticle comprises photo emission stable materials, where the materials emit detectable wavelengths when excited. In another embodiment, the photo emission stable materials comprise quantum dots.

In an embodiment of the present disclosure, the geometry of the MB is selected from the group consisting of: a two-dimensional geometry, a three-dimensional geometry, and a combination thereof. In an embodiment, the two-dimensional geometry is selected from the group consisting of: a flat disc, a flat square, a flat irregular shape, and a combination thereof. In another embodiment, the three-dimensional geometry is selected from the group consisting of: a sphere, a block, and a combination thereof.

An embodiment of the present disclosure includes a method of rapidly analyzing at least one target gene in a sample comprising: encapsulating an aminated magnetic bead (MB) with a first carboxyl quantum dot (QD) nanoparticle to form an MB-QD particle complex; conjugating a capturing probe DNA to the MB-QD particle complex; labeling a signaling probe DNA with a second carboxyl QD nanoparticle; hybridizing the target genomic DNA (gDNA) with the capturing probe DNA conjugated with MB-QD and the signaling probe DNA conjugated with QD; separating the DNA particle hybrids by magnetic application; and detecting and quantifying the target gene via fluorescence measurement. In an embodiment, the method is performed at at least about room temperature.

In an embodiment, the sample is selected from the group consisting of: a purified sample and an unpurified sample. In another embodiment, the sample is selected from the group consisting of: water, a suspension, an emulsion, a colloidal liquid, a mixed phase medium, a solid-liquid medium, and a combination thereof.

In an embodiment of the present disclosure, the sample comprises interference and inhibitory substances selected from the group consisting of: an organic compound, a non-target genomic substance, a non-target DNA, a humic acid, a mineral, an ion, a carbon chemistry based compound, graphene, a residual reagent, and a combination thereof.

In an embodiment of the method of the present disclosure, the first quantum dot is $QD_{655}$, which serves as an internal standard. In another embodiment, the second quantum dot is $QD_{565}$, which serves as a reporter. In another embodiment, the combination of the first and second quantum dot comprise any quantum dot(s).

In an embodiment, the magnetic beads are encapsulated with carboxyl quantum dot nanoparticles (e.g., $QD_{655}$) via a covalent bond between the amine group of the MB and the carboxyl group of the QD. The probe DNA is covalently conjugated with MB-$QD_{655}$ (the covalent bonds are formed between the carboxyl groups of the QDs and the amine groups at the 5' end of the probe DNA). The signaling probe DNA is covalently conjugated with $QD_{565}$ (the covalent bonds are formed between the carboxyl groups of the QDs and the amine groups at the 3' end of the signaling probe DNA).

The use of inorganic QD nanocrystals in labeling oligonucleotides (i.e., probe and signaling probe DNAs) stabilizes the quantification output of the assay (i.e., minimum photobleaching) with a single source of excitation (i.e., $\lambda=360$ nm). The quantification of target DNA is based on sandwich hybridization between the probe and signaling probe DNAs. The capturing MB-$QD_{655}$ particles' functional groups (i.e., carboxyl) is linked to a large number of probe DNAs' functional groups (i.e., amine) to maximize available counterparts for the target DNA. Since the target and signaling probe DNAs are simultaneously hybridized with the probe DNA, the successful hybridization between the target and the signaling probe DNAs is essential for the complete hybridization.

The MB-QD assay of the present disclosure comprises a capturing probe DNA selectively linked to the signaling probe DNA via the target DNA during DNA hybridization. The signaling probe DNA is covalently labeled with fluorescent $QD_{565}$ nanoparticle, which serves as a reporter. The capturing probe DNA is conjugated to both magnetic bead and another $QD_{655}$ nanoparticle, which serve as a carrier and an internal standard, respectively. Successfully hybridized target DNA is separated using a magnetic field. By using a spectrofluorometer, $QD_{565}$ and $QD_{655}$ simultaneously emit at different wavelengths ($\lambda=570$ nm and 660 nm, respectively) under the same excitation source ($\lambda=360$ nm). The output of quantification is expressed by the ratio of the fluorescence between $QD_{565}$ and $QD_{655}$ (i.e., $QD_{565}/QD_{655}$), as the signal (i.e., $QD_{565}$) is normalized by the internal standard (i.e., $QD_{655}$).

In an embodiment of the present disclosure, the target gene to be analyzed comprises bacterial gDNA. In an embodiment, the detection limit is about 890 zeptomolar concentration of ssDNA and 87 gene copies of dsDNA. In another embodiment, the detection limit for bacteria is below the minimum infectious dose.

Embodiments of the present disclosure include a method of analyzing at least one target in a sample where the reagent synthesis, probe preparation, and detection are completed within about 1 day.

Embodiments of the present disclosure include a method of analyzing at least one carbon nanotube (CNT) in a sample comprising: encapsulating a magnetic bead (MB) with a first carboxyl quantum dot (QD) nanoparticle to form an MB-QD particle complex; conjugating a capturing probe DNA to the MB-QD particle complex or magnetic fluorescent bead; labeling a signaling probe DNA with a second carboxyl QD nanoparticle or organic fluorophore; hybridizing the at least one target CNT with the capturing probe DNA conjugated with MB-QD and the signaling probe DNA conjugated with QD; extracting the MB-CNT complexes via a magnetic field; and quantifying the at least one CNT using fluorescence measuring.

In an embodiment of the present disclosure, the sample comprises unpurified water comprising interference and inhibitory substances selected from the group consisting of: an organic compound, a non-target genomic substance, a non-target DNA, a humic acid, a minerals, an ion, a carbon chemistry based compound, graphene, and a combination thereof.

In an embodiment, the magnetic fluorescent bead comprises a fluorophore embedded magnetic particle, where the materials are paramagnetic and emit detectable wavelengths when excited. In another embodiment, the fluorophore comprises a photo emission stable organic material, where the material emits detectable wavelengths when excited. In another embodiment, the photo emission stable organic material comprises Cy5.

Embodiments of the present disclosure include a method of analyzing CNT's in a sample where both probe and signaling DNA co-capture a single CNT during incubation.

Embodiments of the present disclosure include a DNA assay using nanoscale fluorescent quantum dots (QD) and magnetic beads to detect and quantify bacteria. In an embodiment, the assay can detect the minimum infectious dose of the target bacteria. In another embodiment, the assay can be used for the simultaneous quantification of multiple genes.

In an embodiment of the present disclosure, the magnetic bead allows the captured CNT(s) to be separated from any other carbon compounds present in water via magnetic field separation. The fluorescence quantum dots allow the separated CNT(s) to be quantified via fluorescence. The ssDNA allows the CNT(s) to be specifically captured and fastened to the chain of magnetic bead and quantum dots.

Embodiments of the present disclosure include a structure comprising: a capturing probe DNA covalently conjugated with at least one magnetic bead (MB) encapsulated with at least one carboxyl quantum dot (QD) nanoparticle linked to a signaling probe DNA conjugated with at least one QD nanoparticle via sandwich hybridization with a target DNA.

Embodiments of the present disclosure also include a structure comprising: a carbon nanotube (CNT) wrapped with a first and a second ssDNA, where the first ssDNA is labeled with a magnetic fluorescent bead or MB-QD complex, and where the second ssDNA is labeled with a fluorophore or QD.

Embodiments of the present disclosure further include a portable device comprising: an automatic portable system contained within a structure comprising: reagents, a sample loader, a fluidic mixer, an inline magnetic trap, a spectrofluorometer and electronic control board, where the reagents are prepared and stored at about ambient temperature for at least about six months prior to use; the sampler loader draws the sample and reagents into the fluidic mixer; the fluidic mixer mixes the injected reagents and sample and performs hybridization in minutes (e.g., about 45 minutes) at about ambient temperature or about ambient room temperature; the inline magnetic trap captures magnetic bead (MB) and DNA conjugate with an actuatable magnet as the hybridized reagents and sample flow through it; and the spectrofluorometer measures optical intensity at the corresponding wavelengths of the magnetically captured MB and DNA conjugates; and where the method results are obtained within minutes (e.g., about 45 minutes); and most operations are controlled by the electronic control board. In an embodiment, the structure comprises a briefcase. In another embodiment, the structure consists of a stationary robot with robotic arm or tube to sample water in a remote geographical location or hazardous environment and has at least one wireless transceiver to remotely receive operation instructions and send water sample data. In another embodiment, the structure comprises a mobile robot with robotic arm or tube to sample water in remote geographical location or hazardous environment and has at least one wireless transceiver to remotely receive operation instructions and send water sample data wherein the said robot carries the portable device to various water sampling sites for water quality monitoring and analysis.

EXAMPLES

Example 1

A magnetic bead (MB)-quantum dot (QD) nanoparticles based assay capable of quantifying pathogenic bacteria is presently disclosed. The MB-QD assay operates by having a capturing probe DNA selectively linked to the signaling probe DNA via the target genomic DNA (gDNA) during DNA hybridization. The signaling probe DNA is labeled with fluorescent $QD_{565}$ which serves as a reporter. The capturing probe DNA is conjugated simultaneously to a MB and another $QD_{655}$, which serve as a carrier and an internal standard, respectively. Successfully captured target gDNA is separated using a magnetic field and is quantified via a spectrofluorometer. The use of QDs (e.g, $QD_{565}/QD_{655}$) as both a fluorescence label and an internal standard increased the sensitivity of the assay. The passivation effect and the molar ratio between QD and DNA are optimized. The MB-QD assay demonstrated a detection limit of about 890 zeptomolar (i.e., $10^{-21}$ mol $L^{-1}$) concentration for linear single stranded DNA (ssDNA). The present disclosure also demonstrates a detection limit of about 87 gene copies for double stranded DNA (dsDNA) eaeA gene extracted from pure *Escherichia coli* (*E. coli*) O157:H7 culture. Its corresponding dynamic range, sensitivity, and selectivity are also disclosed. Finally, the bacterial gDNA of *E. coli* O157:H7 highlights the MB-QD assay's ability to detect below the minimum infective dose (i.e., 100 organisms) of *E. coli* O157:H7 in water environment.

INTRODUCTION

The availability of nanostructured materials has enabled numerous sensing technologies to leverage their advanced material properties in order to significantly improve performance and robustness [1-3]. Bioassays using nanoparticle labels have the potential to be implemented as part of a miniaturized, portable device for the in-situ monitoring of bacteria [4-7]. Despite the efforts in developing nanoparticle based assays to advance bioanalytics, the related DNA detection technologies are relatively recent and are still in the early stage of development. A number of proof-of-concept studies were confined to the use of single stranded DNA (ssDNA) as the target material and their limitations include compromised sensitivity [8-11]. In addition, there is a current lack in data on their quantification performance in terms of specificity, reproducibility, and sensitivity [12-18].

The present disclosure relates to a DNA assay enabled by nanoscale fluorescent quantum dots (QD) and magnetic beads (MB) which is capable of detecting and quantifying pathogenic bacteria. The presented MB-QD assay is developed specifically for high selectivity and with sufficient sensitivity for detecting the minimum infectious dose of the target pathogen. This disclosure presents the detailed working principle of the MB-QD assay, including the choice of QDs and the conjugation procedure. For an initial demonstration of the sensitivity of the MB-QD assay, varying amount of synthesized target eaeA ssDNA (55 base pairs (bp)) were quantified using the MB-QD assay. To further characterize the MB-QD assay, double stranded DNA (dsDNA) fragment (i.e., 151 bp) from cultured *Escherichia coli* (*E. coli*) O157: H7 bacteria was used as the target DNA. The sensitivity and the selectivity of the MB-QD assay were characterized and validated by real-time polymerase chain reaction (PCR). In particular, the selectivity of the MB-QD assay was investigated through the use of 1 base pair (bp) nucleotide mismatched target DNA. Finally, the functional gene in the bacterial genomic DNA (gDNA) (i.e., 5.4 Mbp) of *E. coli* O157: H7 was used as the target DNA to highlight the MB-QD assay's ability to quantify it in the range of $4 \times 10$-$4 \times 10^5$ colony forming unit (CFU) per mL, which is validated by the agar-based plating counting method. In other words, the MB-QD assay was able to detect below the infectious dose (i.e., 100 organisms) of *E. coli* O157:H7. Note that *E. coli* O157: H7 is chosen because the presence of *E. coli* in water has been an indicator of recent fecal contamination. Among the hundreds of strains of bacterium *E. coli*, the pathogenic *E. coli* O157:H7 is of particular interest. *E. coli* attaching and effacing (eaeA) gene is selected as a target gene because it is relevant and is an excellent genomic marker to many serotypes of pathogenic *E. coli* including *E. coli* O157:H7 [19]. Therefore it is reasonable to select *E. coli* O157:H7 as the study target bacterium as it is food- and water-borne and poses a significant concern in both food safety and aquatic environment [20, 21].

The MB-QD assay comprises a capturing probe DNA selectively linked to the signaling probe DNA via the target DNA during DNA hybridization. The signaling probe DNA is covalently labeled with fluorescent $QD_{565}$ nanoparticle, which serves as a reporter. The capturing probe DNA is conjugated to both magnetic bead and another $QD_{655}$ nanoparticle, which serve as a carrier and an internal standard, respectively. Successfully hybridized target DNA is separated using a magnetic field. By using a spectrofluorometer, $QD_{565}$ and $QD_{655}$ simultaneously emit at different wavelengths ($\lambda$=570 nm and 660 nm, respectively) under the same excitation source ($\lambda$=360 nm). The output of quantification is expressed by the ratio of the fluorescence between $QD_{565}$ and $QD_{655}$ (i.e., $QD_{565}/QD_{655}$), as the signal (i.e., $QD_{565}$) is normalized by the internal standard (i.e., $QD_{655}$). The purpose of the internal standard is to circumvent well known issues such as variable number of particles in each reaction, paramagnetic instability of nanoscale MBs, and aggregation of particles.

The use of various QD labels compensate for the lack of photostability that is common among conventional organic fluorophores [1, 22]. It also allows the particles to be illuminated with a single light source (i.e., excitation). In comparison to the previous studies [23, 24] that employed the organic fluorophores as a part of the signaling probe DNA, higher photostability is expected due to the resistance of inorganic nanocrystals against photobleaching. Another advantage of this format is its potential to be used for the simultaneous detection of multiple genes. By having a magnetic bead in the center of format (i.e., carrier), more pairs of QDs for both signaling probe DNA (i.e., reporter) and capturing probe DNA (i.e., internal standard) can be made available. Therefore, with the same excitation source, it is theoretically possible to perform simultaneous quantification of multiple genes.

Experimental

Materials and Apparatus

The linear DNA oligonucleotides were designed and commercially synthesized (IDT, Coralville, Iowa) based on the sequences of eaeA gene (Genbank accession: X60439.1). The sequences of DNA oligoprobes used in this study are shown in Table 1. The aminated magnetic beads (Dynabead M270, Invitrogen, Carlsbad, Calif.) were encapsulated with carboxyl quantum dot nanoparticles ($QD_{655}$, Invitrogen) and the signaling probe DNA was labeled with carboxyl quantum dot nanoparticles ($QD_{565}$, Invitrogen) via the formation of amide bond. Mono- and di-basic phosphate salt, bovine serum albumin (BSA), ethylcarbodiimide hydrochloride (EDC), N-hydroxysuccinimide (NHS) and hydroxylamine were obtained from Sigma-Aldrich (St. Louis, Mo.). Sodium borohydride ($NaBH_4$) and sodium dodecyl sulfate (SDS) were purchased from MP Biomedicals (Solon, Ohio) and 20×SSC (saline sodium citrate) was provided from Fisher Scientific (Pittsburgh, Pa.). All hybridization reactions were implemented in a 48-well PCR tube plate (Applied Biosystems, Foster City, Calif.) nested inside a hybridization incubator (UVP HB-500 Minidizer Hybridization, Fisher Scientific). DIG easy hybridization buffer (Roche Diagnostic, Basel, Switzerland) was used for the DNA hybridization process. A 96-well magnet (MPC®-965, Invitrogen) was used to extract particle-DNA complexes out of the solution for washing and separation. In order to avoid nonspecific adsorption of QDs on the tube wall [25], the plastic centrifuge tubes were pretreated with the 0.5% BSA solution in phosphate buffer saline (PBS, 0.1 mol $L^{-1}$, pH 7.5).

TABLE 1

The sequences and the modification of *E. coli* O157:H7 eaeA DNA oligonucleotides.

| DNA oligonucleotides | Sequence (5' → 3') and modification |
|---|---|
| Probe DNA | SEQ ID NO: 1 $NH_2$-CGGAT A AGAC TTCGG CTAAA\* |
| 1 bp mismatched probe DNA\*\* | SEQ ID NO: 2 $NH_2$-CTTAT ACCGC GACCG TGA AA |
| Signaling probe DNA | SEQ ID NO: 3 CTTAT ACCGC GACGG TGA AA-$NH_2$<br>SEQ ID NO: 4 ACCGT CGCGG TATAA GTAAT |
| Target ssDNA | GGTAT CGGCG TTATC CGCTT TAGCC GAAGT CTTAT |
| Forward primer\*\*\* | SEQ ID NO: 5 GGCGG ATAAG ACTTC GGCTA |
| 1 bp mismatched Forward primer | SEQ ID NO: 6 GGCGG ATAAC ACTTC GGCTA |
| Reverse primer | SEQ ID NO: 7 CGTTT TGGCA CTATT TGCCC |

\*The complementary sequences in target DNAs corresponding to probe DNAs (including signaling probe DNA) are represented by boldface and mismatched base pairs are underlined.
\*\*1 bp mismatched, both probe DNA and forward primer was designed for the selectivity experiments.
\*\*\*The set of forward and reverse primers is designed to amplify the gene fragment (i.e., 151 bp) that is a part of eaeA gene (i.e., 3131 bp) [25].

Preparation of MB-QDs Particle Complex and DNA-QDs Conjugation

Magnetic beads (MB, $2 \times 10^7$ beads $mL^{-1}$) were encapsulated with $QD_{655}$ (2 μmol $L^{-1}$, 8 μL) via a covalent bond between the amine group of MB and the carboxyl group of QD. The probe DNA and signaling probe DNA were covalently immobilized on the surface $QD_{655}$ and $QD_{565}$, respectively. The covalent bonds were formed between the carboxyl groups of QDs and the amine groups at the 5' end of probe DNA and 3' end of signaling probe DNA. The schematic diagram of the covalent bonds is illustrated in FIG. 1. About 160 μmoles of signaling probe DNA was added to the solution of $QD_{565}$ nanoparticles (2 μmol $L^{-1}$, 8 μL). Subsequent to adding about 10 μL of the mixture of EDC and NHS (about 1:1 in a molar basis), which was prepared immediately prior to use, the particles were incubated at ambient temperature with a slow tilt rotation for about 2 h.

Passivation, Optimum Molar Ratio and Photostability

Preliminary experiments such as passivation, optimum molar ratio, and photostability tests were performed prior to DNA hybridization in order to optimize the MB-QD assay. Passivation is a common method for avoiding a non-specific binding (i.e., particle coagulations in this case) by inactivating the functional groups. The signaling probe DNA labeled with $QD_{565}$ was incubated in a $NaBH_4$ based blocking solution (0.5 g of $NaBH_4$ in the mixture of 10 mL 20×SSC, 0.5 mL 10% SDS, and 90 mL $H_2O$) at 42° C. for 20 min to passivate the remained functional groups on the $QD_{565}$ surface, and washed with 1×SSC and 0.2×SSC twice. The signaling probe DNA with $QD_{565}$ was subsequently collected by centrifuging twice at 10,000 rpm for 5 min. In order to examine the passivation effect of the nanoparticle labels on DNA hybridization, both treated and non-treated QD$_{565}$—signaling probe DNAs were compared during hybridization.

The molar ratio effect of QD$_{565}$ to signaling probe DNA (i.e., about 1:3, 1:10, and 1:30) on the hybridization efficiency was examined. The optimum molar ratio of signaling probe DNA and QD$_{565}$ was determined by the highest output signal of fluorescence after hybridization. The photostability of fluorescent nanocrystal label was compared to organic fluorophore Cy3 in order to verify photobleaching resistance of QDs as labels. Fluorescence measurement was performed for signaling probe DNAs labeled with both QD$_{565}$ and Cy3 and compared in accordance to the relative signal of hybridization between the two labels. The fluorescence intensity was measured for 25 min duration.

Quantification of ssDNA

In order to demonstrate the sensitivity of the present assay compared to other nanoparticle based assays, various amounts of target eaeA ssDNA (55 bp) were quantified in the proposed hybridization platform. The probe DNA conjugated MB-QD particles were resuspended in about 400 μL DIG easy Hyb buffer with about 500 pmoles of signaling probe DNA labeled with QD$_{565}$ and the varying amount of target ssDNA with the range of about 1-10$^5$ attomolar (i.e., 10$^{-18}$ mol L$^{-1}$) concentration. This mixture was incubated for about 8 h at about 37° C. with a slow tilt rotation to facilitate DNA hybridization. The mixture was washed three times with phosphate buffer (PB, about 0.1 mol L$^{-1}$, pH about 7.4) and the fluorescence of both QDs was measured by a spectrofluorometer.

Pure Bacterial *E. coli* O157:H7 Culture and Genomic DNA Extraction

The pure bacterial culture of *E. coli* O157:H7 (ATCC 43888) was grown in about 1 mL of trypticase soy broth (Difco Laboratories, Detroit, Mich.) at about 37° C. for about 20 h based on the ATCC's protocol. Subsequently about 5 μL of the liquid culture was transferred to about 5 mL of trypticase soy media for further growth at the same condition. Genomic DNA was extracted from the cultures using FastDNA® SPIN for Soil kit (MP Biomedicals) in accordance to the manufacturer's instructions. DNA concentration and purity were measured by UV absorption at about 260 nm and 280 nm using a Nanodrop ND-1000 spectrophotometer (Nanodrop Technologies, Wilmington, Del.).

Generation of Test dsDNA Sample Via PCR

In order to characterize the MB-QD assay's sensitivity and selectivity, dsDNA target fragments (151 bp) were produced via PCR reaction. PCR amplification was carried out in the 2720 Thermal Cycler (Applied Biosystems) with the following program: initial denaturation step at about 95° C. for about 3 min, followed by 40 cycles of amplification with denaturation at about 95° C. for about 30 s, annealing at about 60° C. for about 30 s, and elongation at about 72° C. for about 1 min, and ending with a final extension at about 72° C. for about 5 min [20]. PCRs were performed by adding about 5 μL of DNA to about 45 μL of mixture comprising 1×AmpliTaq PCR buffer (Applied Biosystems), about 2 mmol L$^{-1}$ of AmpliTaq MgCl$_2$ (Applied Biosystems), about 0.2 mmol L$^{-1}$ of dNTPs (Takara BIO INC, Shiga, Japan), about 2.5 units of AmpliTaq Gold DNA polymerase (Applied Biosystems), DNAse/RNAse free water (GIBCO®), and about 0.4 μmol L$^{-1}$ of both forward and reverse primers [26]. The sequences of both primers are presented in Table 1. Negative control (i.e., sterile water) was included to verify the accuracy of the amplification. The PCR amplicon fragment size was examined using about 2% agarose gel with about 0.5×TBE (Tris boric acid EDTA, Applied Biosystems) buffer at about 65 V for about 1.5 h and visualized with a UV Transilluminator (Fisher Scientific) by ethidium bromide (about 0.5 μg mL$^{-1}$) staining. A 100 bp DNA ladder (Promega, Madison, Wis.) was used to determine the size of DNA. Prior to hybridization, the PCR products were purified using a DNA Clean and Concentrator kit (Zymo, Orange, Calif.) as described by the manufacturer. The molecular weight of PCR product was calculated to be 46,762.5 g mol$^{-1}$ and was used for the further calculation of the eaeA gene copy numbers.

Sensitivity of Assay

The sensitivity of the MB-QD assay was characterized via the quantification of the PCR amplified dsDNA (151 bp). The hybridization followed the same procedure as that of the ssDNA. The dsDNA target was denatured to open up the double helix structure for the hybridization between probe DNAs and target DNA. The dsDNA was heated at about 95° C. for about 5 min and sonicated for about 30 sec before injecting into the hybridization tube [24]. The subsequent hybridization step followed the same procedure described earlier. The linearity (i.e., regression equation and correlation coefficient), dynamic range of standard curve, and limit of detection (LOD) were determined to indicate the sensitivity of assay. LOD was calculated as follows: LOD=t$_{(n-1,0.99)}$·(s), where t$_{(n-1,0.99)}$: the students' t value appropriate for a 99% confidence level and a standard deviation estimate with n−1 degrees of freedom, s: standard deviation (SD) of the replicate analyses using blank sample, n:10 [27]. In order to examine the precision of the MB-QD assay, two types of coefficient of variation (CV) were calculated. CV is defined as the ratio of the standard deviation to the mean value. Inter-assay CV, which describes the instrumental precision, was obtained from the five measurements of both assay output within one experiment. Intra-assay CV, which describes the errors from each triplicate experiment, was calculated from the three different experiments.

To validate the assay's sensitivity, real-time PCR assay was implemented with the same dsDNA template as our assay. For the real-time PCR assay, the purified PCR products (151 bp) were added to a reaction mix to a final volume of about 25 μL, containing 1×Universal SYBR Green master mix (Applied Biosystems), and about 0.5 μmol L$^{-1}$ of each primer. The reactions were performed by a StepOne™ Real-Time PCR (Applied Biosystems) with the following programs: about 95° C. for about 10 min and 40 cycles of about 95° C. for about 15 s, about 63° C. for about 1 min, and about 72° C. for about 30 s. Subsequent melt curve analysis involved heating the products to about 95° C. for about 15 sec, followed by about 55° C. for about 30 sec and slowly heating to about 95° C. for about 15 sec[28].

Selectivity of MB-QD Assay

The selectivity of the developed assay to discriminate target DNA from 1 by mismatched DNA was demonstrated. The 1 bp mismatched probe DNA-particle conjugates were hybridized with the various amounts of dsDNA fragments and QD$_{565}$-labeled signaling probe DNA. In parallel, real-time PCR analysis was performed with the same procedure as mentioned above with 1 bp mismatched forward primer.

Quantification of *E. coli* O157:H7 by gDNA Hybridization

The quantification of *E. coli* O157:H7 was implemented by using gDNA of pure culture and therefore bypassed an amplification step. The schematic diagram of the MB-QDs particle based gene quantification assay for *E. coli* O157:H7 with signaling probe DNA labeled with QD$_{565}$ is shown in FIG. 1. In parallel to the hybridization of MB-QD, the traditional plate counting assay was performed as verification. *E. coli* O157:H7 pure cultures were serially diluted with PBS to determine the bacterial concentration. One hundred microliter of each dilution was surface plated on trypticase soy agar plates and they were incubated at about 37° C. for about 24 h. The colonies were counted to determine the number of CFU per mL.

Fluorescence Measurement

The quantification of target DNA in our developed assay was performed by measuring the fluorescence of $QD_{565}$ and $QD_{655}$. The fluorescence measurements were performed using a spectramax M2 microplate reader (Molecular Devices, Sunnyvale, Calif.) and 96 well plates (Nunc, Roskilde, Denmark). The maximum endpoint emission wavelength was 570 nm and 660 nm for $QD_{565}$ and $QD_{655}$, respectively, under the same excitation wavelength (i.e., 360 nm). All gene quantification results presented in this study are shown as the normalized fluorescence (i.e., $QD_{565}/QD_{655}$).

Results and Discussion

Optimization of Signaling Probe DNA Labeling with $QD_{565}$

In the developed assay format, the probe and signaling probe DNAs were covalently conjugated with MB-$QD_{655}$ and $QD_{565}$, respectively. The use of inorganic QD nanocrystals in labeling oligonucleotides (i.e., probe and signaling probe DNAs) stabilizes the quantification output of the assay (i.e., minimum photobleaching) with a single source of excitation (i.e., λ=360 nm). The labeling optimization of signaling probe DNA with $QD_{565}$ is shown in FIGS. 2 and 3.

Figure 2:
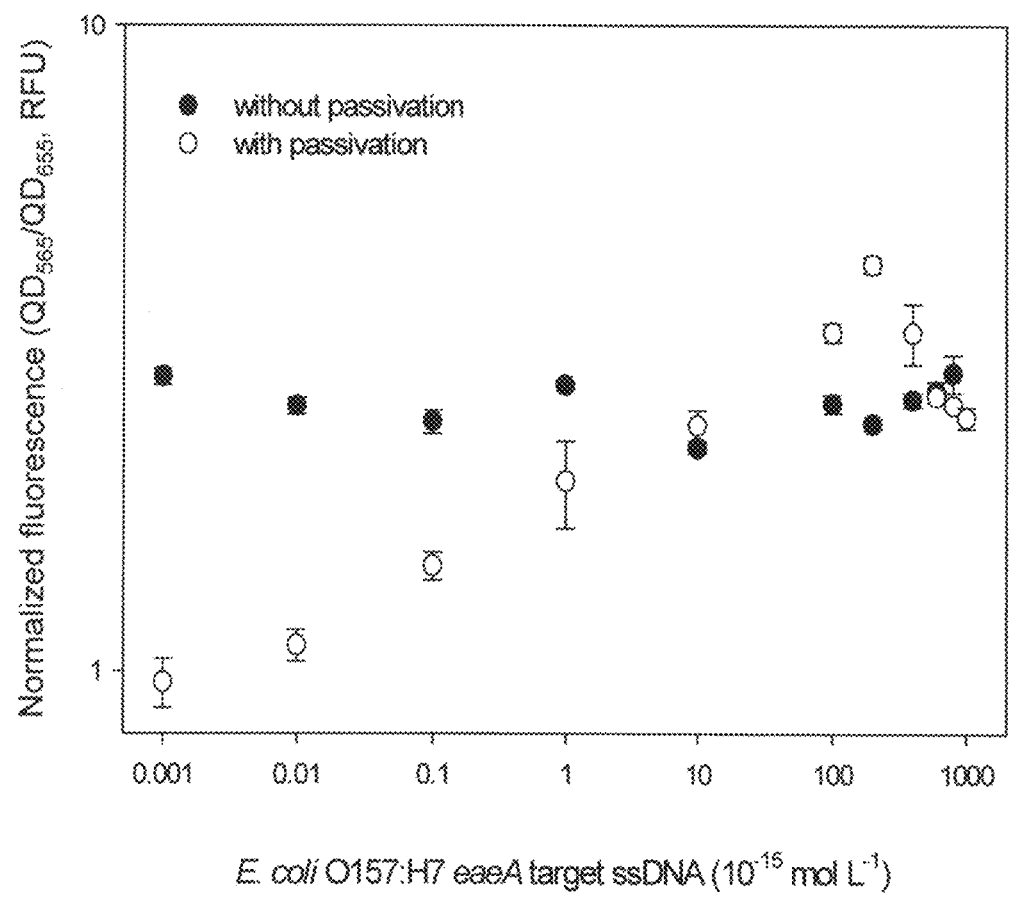
FIG. 2 is a graph that illustrates the effect of passivation treatment for $QD_{565}$ labels. The signal and error bar represent mean and SD, respectively, based on five measurements of fluorescence intensity by a spectrofluorometer (note that this description remains the same for the following FIGS. 3 through 5).
Figure 3:
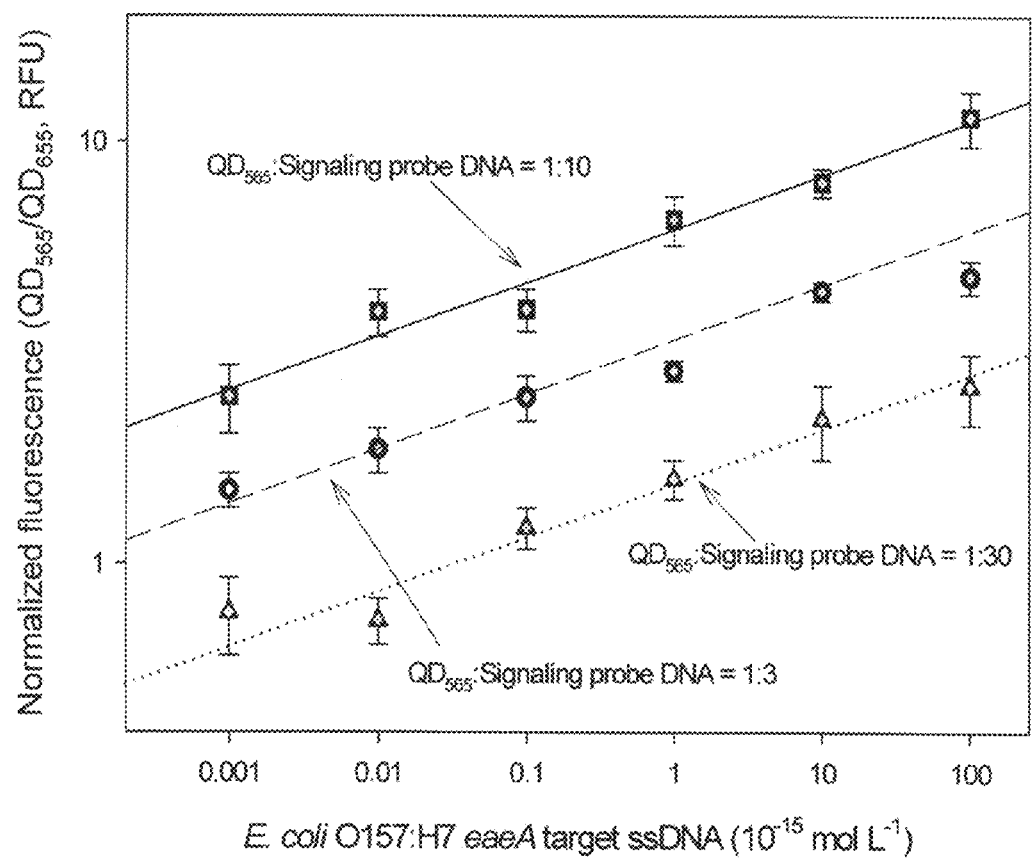
FIG. 3 is a graph that illustrates the effect of the molar ratio of $QD_{565}$ to signaling probe DNA on the DNA quantification. The molar ratio of 10 of signaling probe DNA to $QD_{565}$ was optimized for the signaling probe labeling based on the resulted fluorescence signal.

The effect of passivation treatment for $QD_{565}$ labels (i.e., conjugated with a signaling probe DNA) is presented in FIG. 2. The passivation of $QD_{565}$ labels allowed the fluorescence output to increase accordingly when the amount of target ssDNA increases. This indicated that the quantification is only feasible with the use of passivated nanoparticle labels. For non-passivated labels, no change of fluorescence was observed with a various amount of target ssDNA. One possible cause involves particle aggregation via non-specific binding which can be induced by the remaining functional groups on the surface of non-treated $QD_{565}$ labels. The passivation of QDs in the signaling probe DNA can prevent particle agglomeration which is caused by the unoccupied functional groups of $QD_{565}$.

The quantification of target DNA is based on sandwich hybridization between the probe and signaling probe DNAs. The capturing MB-$QD_{655}$ particles' functional groups (i.e., carboxyl) is linked to a large number of probe DNAs' functional groups (i.e., amine) to maximize available counterparts for the target DNA. Since the target and signaling probe DNAs are simultaneously hybridized with the probe DNA, the successful hybridization between the target and the signaling probe DNAs is essential for the complete hybridization. The ratio between the numbers of signaling probe DNA and label has to be optimized to maximize the output of the assay (i.e., fluorescence). The effect of $QD_{565}$ to signaling probe DNA molar ratio on DNA quantification is shown in FIG. 3. The molar ratios of $QD_{565}$ to signaling probe DNA were varied as 1:3, 1:10, and 1:30. The maximum output of assay was observed at the signaling probe DNA to $QD_{565}$ molar ratio of 10. At higher molar ratio of $QD_{565}$ to signaling probe DNA (e.g., 1:30), one $QD_{565}$ conjugated with signaling probe DNAs may be hybridized with several target DNAs. In this case, relatively less amounts of $QD_{565}$ are utilized for the hybridization, thus resulting in a weak assay signal. On the other hand, lower molar ratio of $QD_{565}$ to signaling probe DNA (e.g., 1:3) will decrease the probability of DNA hybridization due to lesser amount of signaling probe DNA. This can also result in weak assay signal. For this assay format the optimum molar ratio is established at 10. The signaling probe DNA and labels were optimized in terms of molar ratio and passivation prior to the subsequent quantification experiments in later sections.

Photostability of the Assay

Figure 4:
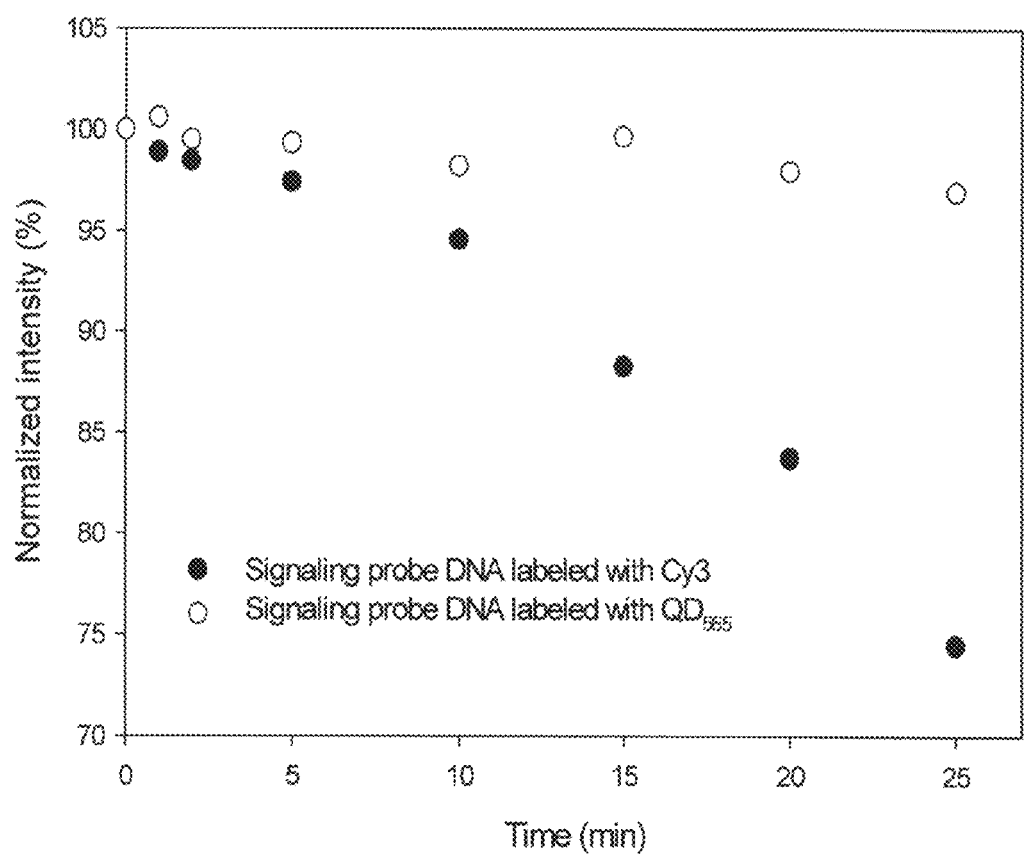
FIG. 4 is a graph that illustrates a comparison of signal photostability obtained by using signaling probe DNA labeled with Cy3 and $QD_{565}$. The QDs nanocrystals that are made of semi-conducting materials have shown the excellent photostability over organic fluorophore, Cy3.

The main advantage of using QD over organic fluorophore as a label for the assay is its photostability, which is defined as the resistance to photobleaching. Photostability of both QDs and Cy3 labeled DNAs was monitored via continuous measurement of the fluorescence intensity for about 25 min. As shown in FIG. 4, the fluorescence intensity of the signaling probe DNA with QDs maintained its initial intensity for the duration of the experiment, but that obtained from the DNA with Cy3 decreased to about 75% after about 25 min. The results showed that the QD nanoparticles label has better stability for the hybridization as compared to the organic fluorophore, Cy3.

Quantification of ssDNA

Figure 5:
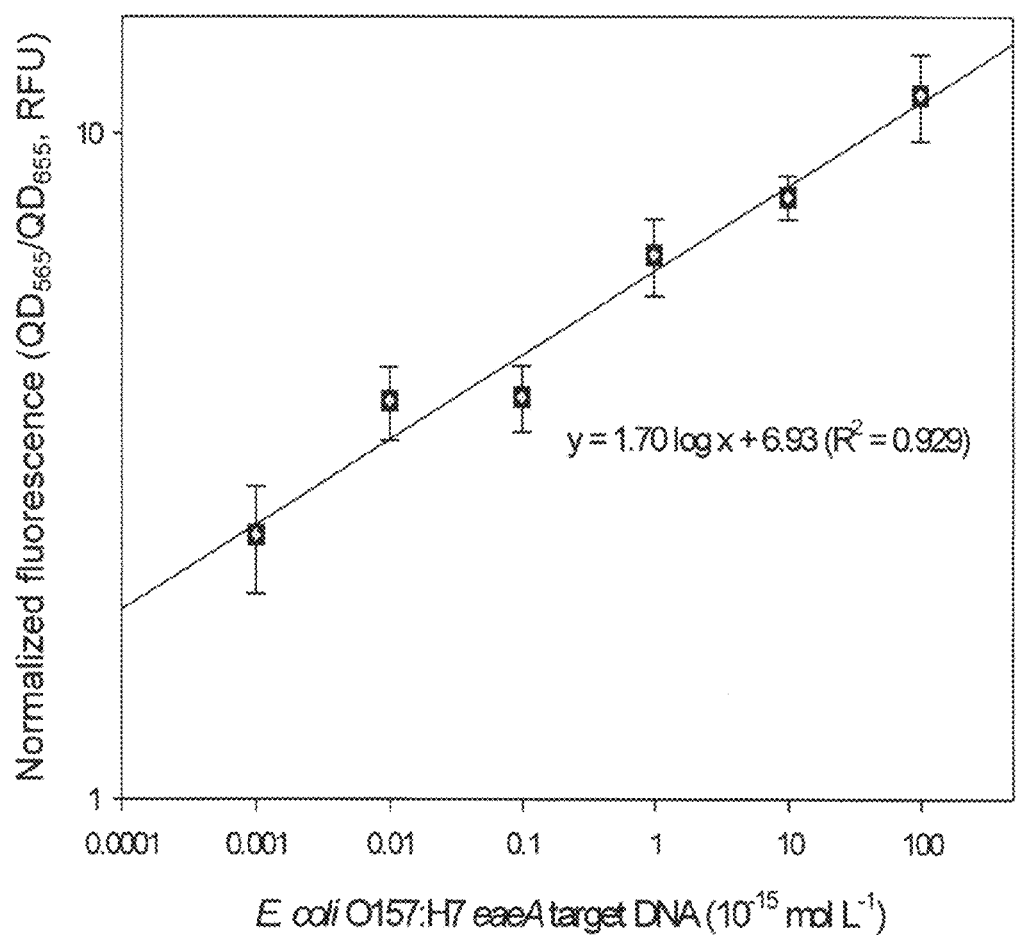
FIG. 5 is a graph that illustrates $E.\ coli$ O157:H7 eaeA target ssDNA quantification in an embodiment of the particle based hybridization assay. The normalized fluorescence has shown the strong linearity ($R^2=0.929$) over 5 magnitude of order with a limit of detection (LOD) of 890 zeptomolar concentration ($10^{-21}$ mol $L^{-1}$).

In order to characterize the quantification range and linearity of the MB-QD assay, hybridization was performed using ssDNA as the target. The quantification result is presented in FIG. 5. A linear quantitative relationship was observed in the range of about $10^{-18}$ to $10^{-13}$ mol L. The normalized fluorescence (i.e., $QD_{565}/QD_{655}$) showed a linearity ($R^2$=0.929) of over 5 orders of magnitude with the LOD of about 890 zeptomolar concentration (i.e., zM=$10^{-21}$ mol L$^{-1}$). The detection of ssDNA in various formats was reported in several prior literatures: $2\times10^{-9}$ mol L$^{-1}$ in the gold nanoparticle based fluorescence quenching method [10]; $1\times10^{-10}$ mol L$^{-1}$ by MB-functionalized fluorescent microspheres [29]; $1\times10^{-12}$ mol L$^{-1}$ in the format of gold nanoparticles coupled light scattering [30]; $8\times10^{-13}$ mol L$^{-1}$ in the dye-doped silica nanoparticle based hybridization [11]; $5\times10^{-15}$ mol L$^{-1}$ in the silver nanoparticle based chemiluminescent method [31]; and $8.3\times10^{-18}$ mol L$^{-1}$ by the magnetic particles with electrogenerated chemiluminescent detection [32]. Recently Liu et al. [8] reported the feasibility of detecting ssDNA of 250 zM (i.e., $2.5\times10^{-19}$ mol L$^{-1}$) by QD nanoparticle labeling. The result however was preliminary. The assay had only three points examined and no LOD reported. More importantly there was no internal standard to normalize the assay output, thereby potentially resulting in the poor reproducibility of the assay. As compared to the previous studies listed above, the MB-QD assay demonstrated excellent sensitivity for the detection of ssDNA.

Quantification of dsDNA: Sensitivity

Figure 6:
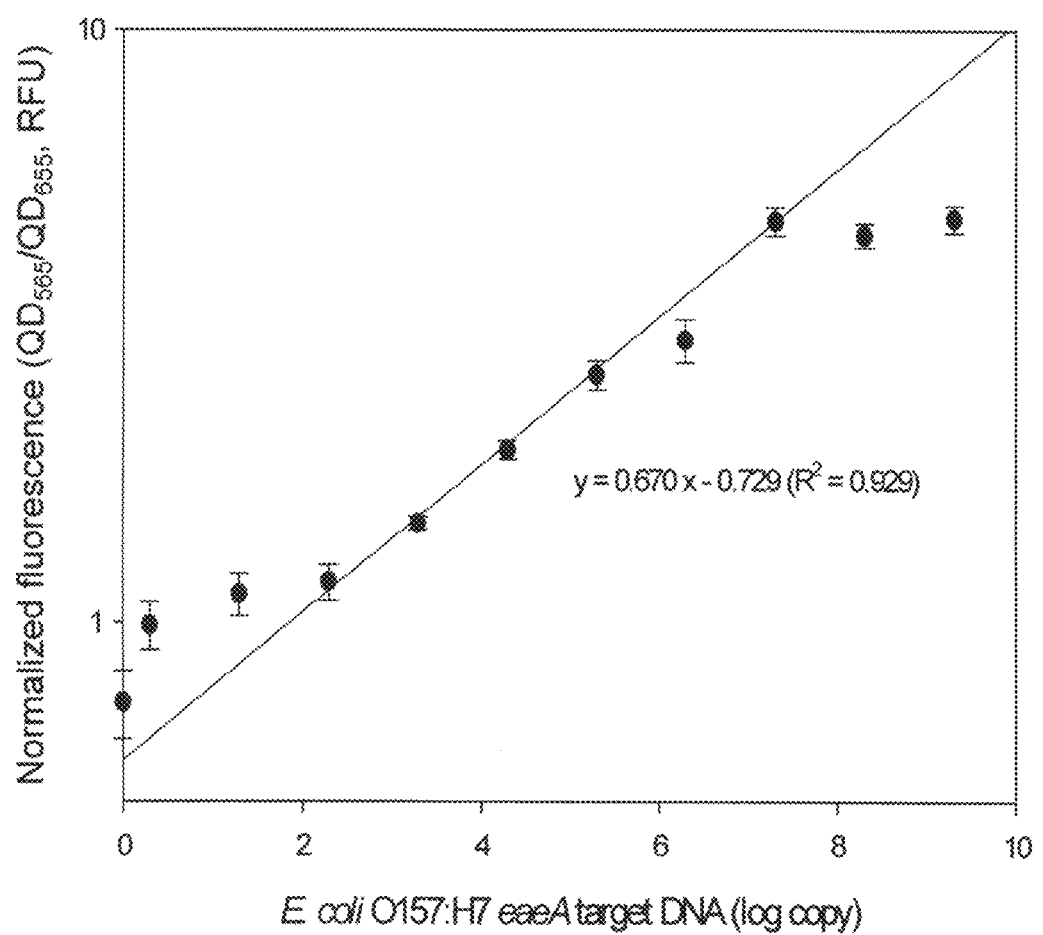
FIG. 6 is a graph that illustrates quantification of $E.\ coli$ O157:H7 eaeA target dsDNA in the MB-QDs particle based DNA hybridization. The normalized fluorescence is plotted against the corresponding $E.\ coli$ O157:H7 eaeA gene copy numbers. The linear range of quantification was $2\times10^2\text{-}2\times10^7$ with the LOD of 87 gene copies. The signal and error bar represent mean and SD, respectively, based on the triplicate experiments (note that this description remain the same for the following FIGS. 7 and 8).

The characterization of the MB-QD assay's sensitivity was carried out via dsDNA quantification. The standard curve constructed by the serial dilution of dsDNA fragments (i.e., 151 bp of PCR amplicon) and the quantification results are presented in FIG. 6 and Table 2. The linear quantification range was $2\times10^2$-$2\times10^7$ with the LOD of 87 gene copies. The dynamic range was 5 orders of magnitude. The lower detection limit of dsDNA in the developed MB-QD assay (i.e., 87 gene copies) presented here is a significant improvement over previously reported assay for the nanoparticle based DNA quantification. For example, Storhoff et al. [33] demonstrated the detection of at least $6\times10^6$ gene copies of the PCR product from human gDNA using silver amplified gold nanoparticles in DNA microarray format; Eastman et al. [34] developed a QD nanobarcode-based magnetic microbead array for gene expression analysis with a sensitivity of $10^4$-$10^6$ gene copies; and Hill et al. [14] reported that $2.5\times10^{-15}$ mol L$^{-1}$ (i.e., $7.5\times10^4$ gene copies) of bacterial gDNA was detected at the bio-bar-code assay using gold nanoparticles. To evaluate the quantification capability of the MB-QD assay, real-time PCR analysis was conducted. The linear range of real-time PCR was $2\times10^2$-$2\times10^9$ with the LOD of 47 gene copies.

TABLE 2

Quantification performance of the particle based assay.

| | |
|---|---|
| Dynamic range (gene copies) | $2 \times 10^2 - 2 \times 10^7$ |
| Regression equation | RFU – 0.670 log (gene copies) – 0.729 |
| Correlation coefficient ($R^2$) | 0.929 |
| Limit of detection (gene copies) | 87 |
| Inter-assay CV (%) | 2.01 |
| Intra-assay CV (%) | 5.74 |

NOTE:
RFU: relative fluorenscence unit;
CV: coefficient of variation.

Quantification of dsDNA: SPECIFICITY

Figure 7:
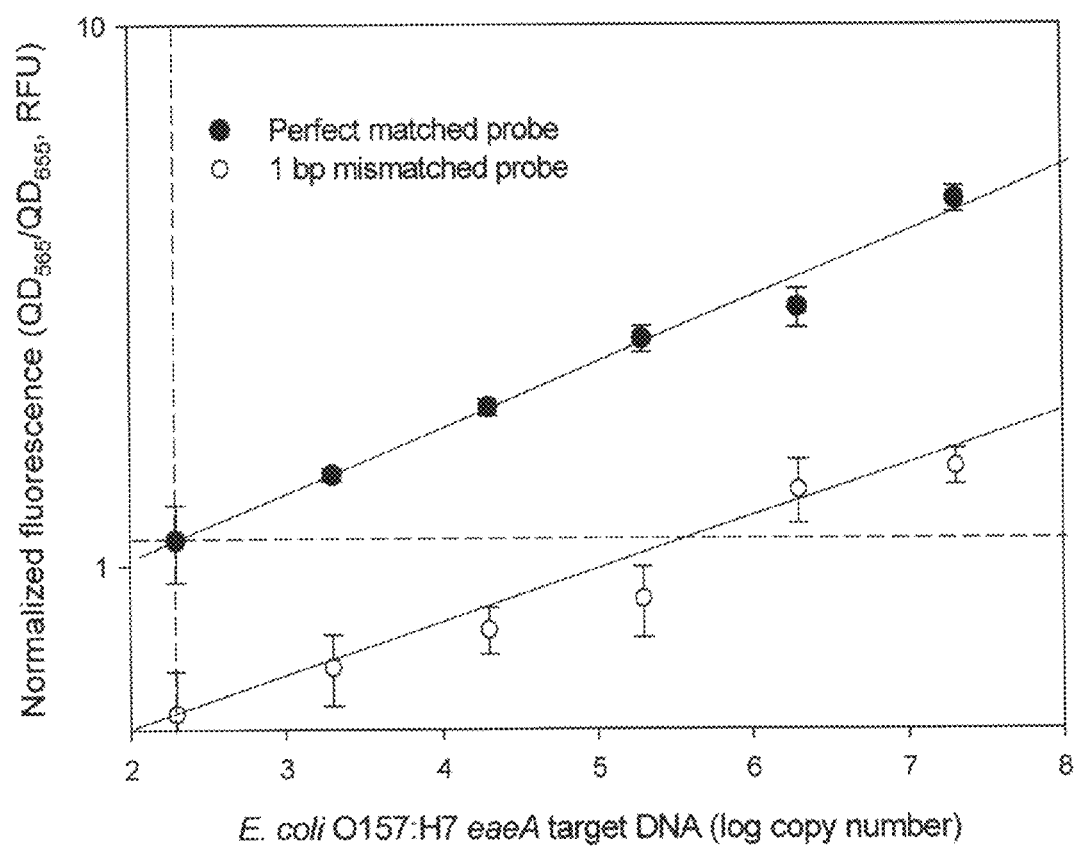
FIG. 7 is a graph that illustrates assay specificity of the MB-QDs particle based DNA hybridization. $E.\ coli$ O157:H7 eaeA target dsDNA was hybridized with both perfectly matched and 1 bp nucleotide mismatched probe DNA.

The specificity of the MB-QD assay was characterized by varying the amount of PCR amplicon hybridized with both perfectly matched and 1 bp nucleotide mismatched probe DNAs. The specificity result is presented in FIG. 7. By comparing the fluorescence signal, 1 bp mismatched probe DNA was clearly discriminated from the perfectly matched probe DNA. When the 1 bp mismatch was used, the quantification results were observed to be below the LOD (i.e., RFU=1.17) in the range of $2 \times 10^2 - 2 \times 10^5$ target gene copies. This result demonstrated the present method is capable of screening and detecting pathogenic bacteria with an excellent selectivity among other non-pathogenic but phylogenetically similar bacteria. Real-time PCR assay (graph not shown) was implemented to validate the specificity of MB-QD assay. In the real-time PCR assay, 1 bp nucleotide mismatched forward primer was adopted to simulate the 1 by nucleotide mismatch effect. When the 1 bp mismatched primer was used, the limit of quantification increased from $2 \times 10^2$ to $2 \times 10^4$ and the dynamic range shifted accordingly.

Quantification of Non-Amplified gDNA and Validation

Figure 8:
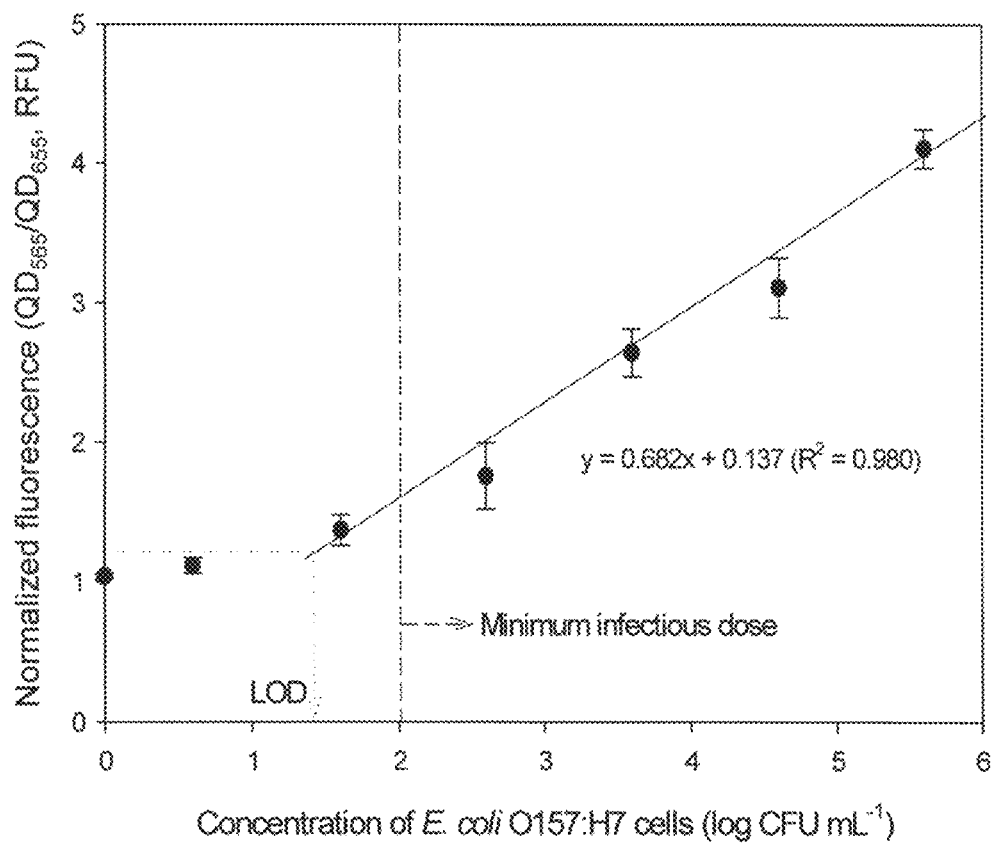
FIG. 8 is a graph that illustrates quantitative detection of $E.\ coli$ O157:H7 using genomic DNA without amplification. Genomic DNA of pure bacterial culture of $E.\ coli$ O157:H7 was quantified targeting eaeA gene in the MB-QD assay. The output of the assay, depicted in y-axis, is the normalized fluorescence. Gene copy numbers (i.e., the variable of assay) were converted to the number of bacterial cells (CFU $mL^{-1}$) and presented to x-axis, based on the result of the plate counting method. The dynamic range of the assay was $4\times10\text{-}4\times10^5$ CFU $mL^{-1}$ ($R^2=0.980$) with the LOD of 25 CFU $mL^{-1}$. This technique is able to detect below the minimum infectious limit (i.e., 100 organisms) as indicated by the vertical dashed line.

In order to demonstrate the assay's capability to perform quantification without the need of amplification, non-amplified genomic DNA of E. coli O157:H7 culture was used as the target. A standard culture based bacteria quantification method was employed to correlate the DNA-based quantification and conventional bacterial cell counts. Target gDNA with various gene copies were hybridized and the quantification result is shown in FIG. 8. The output of the assay, depicted in the y-axis, is the normalized fluorescence. Gene copy numbers (i.e., a variable of assay) were converted to the number of bacterial cells (CFU $mL^{-1}$) based on the result of the plate counting method and subsequently depicted in the x-axis. Plate counting method was implemented using active E. coli O157:H7 cells and correlated with gene quantification results. $4 \times 10^9$ CFU per mL was determined to be equivalent to $2 \times 10^{12}$ gene copy numbers of the eaeA per mL. The dynamic range of the assay was $4 \times 10 - 4 \times 10^5$ CFU $mL^{-1}$ ($R^2$=0.980) with the LOD of 25 CFU $mL^{-1}$. The infectious dose (i.e., >100 organisms) [35, 36] was indicated by the vertical dashed line in FIG. 8. The minimum infectious dose of E. coli O157:H7 was within the range of quantification of the MB-QD assay. In comparison, other studies have shown that their LODs were similar or more than 100 CFU $mL^{-1}$ [20, 37-40], indicating the MB-QD assay has higher sensitivity for the detection of pathogens. Similar techniques have been recently developed and they are based on DNA aptamer or liposome. Bruno et al. [41] have developed DNA aptamer based sandwich hybridization approach with magnetic bead and QDs. Zaytseva et al. [42] used fluorescent liposome as a reporter for the detection of viral nucleic acids. Even though these developments have demonstrated the integration of the assay with portable devices such as microfluidics, they are still in the early stage of development.

Conclusion

A highly sensitive DNA assay using magnetic and quantum dot nanoparticles for the quantification of pathogenic E. coli O157:H7 bacteria is disclosed. The use of $QD_{565}$ as a label for the signaling probe DNA resulted in increased photostability and also allowed the assay to be used with a single, short-wavelength excitation source. The new format of QDs configuration (i.e., $QD_{565}/QD_{655}$) as both a fluorescence label and an internal standard increased the sensitivity of the assay. This MB-QD assay was able to detect ssDNA and dsDNA fragment up to 890 zeptomolar concentration and 87 gene copies, respectively. The specificity of the assay was also demonstrated via the discrimination of target DNA with 1 bp nucleotide mismatched probe DNA. Finally the MB-QD assay was able to detect E. coli O157:H7 with 25 CFU $mL^{-1}$ of the LOD which is below the minimum infectious dose in water. This sensitive nanoparticle based DNA quantification assay is potentially applicable for in-situ monitoring of pathogenic bacteria in aquatic environments.

REFERENCES

Which are Herein Incorporated by Reference

[1] M. Bruchez, M. Moronne, P. Gin, S. Weiss, A. P. Alivisatos, Science 281 (1998) 2013.
[2] W. C. Chan, D. J. Maxwell, X. Gao, R. E. Bailey, M. Han, S. Nie, Curr. Opin. Biotechnol., 13 (2002) 40.
[3] I. Willner, R. Baron, B. Willner, Biosens. Bioelectron., 22 (2007) 1841.
[4] S. Andreescu, J. Njagi, C. Ispas, M. T. Ravalli, J. Environ. Monit., 11 (2009) 27.
[5] N. Sanvicens, C. Pastells, N. Pascual, M.-P. Marco, TrAC, 28 (2009) 1243.
[6] C. Situma, M. Hashimoto, S. A. Soper, Biomol. Eng 23 (2006) 213.
[7] S. P. Mulvaney, C. L. Cole, M. D. Kniller, M. Malito, C. R. Tamanaha, J. C. Rife, M. W. Stanton, L. J. Whitman, Biosens. Bioelectron., 23 (2007) 191.
[8] Y.-J. Liu, D.-J. Yao, H.-Y. Chang, C.-M. Liu, C. Chen, Biosens. Bioelectron., 24 (2008) 558.
[9] X. Zhou, J. Zhou, Anal. Chem., 76 (2004) 5302.
[10] Z.-S. Wu, J.-H. Jiang, L. Fu, G.-L. Shen, R.-Q. Yu, Anal. Biochem., 353 (2006) 22.
[11] X. Zhao, R. Tapec-Dytioco, W. Tan, J. Am. Chem. Soc., 125 (2003) 11474.
[12] Y. S. Kim, B. C. Kim, J. H. Lee, J. Kim, M. B. Gu, Biotechnol. Bioprocess Eng., 11 (2006) 449.
[13] E. Liandris, M. Gazouli, M. Andreadou, M. Comor, N. Abazovic, L. A. Sechi, J. Ikonomopoulos, J. Microbiol. Methods, 260-264 (2009).
[14] H. D. Hill, R. A. Vega, C. A. Mirkin, Anal. Chem., 79 (2007) 9218.
[15] P. Ashtari, X. He, K. Wang, P. Gong, Talanta, 67 (2005) 548.
[16] Y.-T. Chen, C.-L. Hsu, S.-Y. Hou, Anal. Biochem., 375 (2008) 299.
[17] M. Ye, Y. Zhang, H. Li, Y. Zhang, P. Tan, H. Tang, S. Yao, Biosens. Bioelectron., 24 (2009) 2339.
[18] G. Doria, B. G. Baumgartner, R. Franco, P. V. Baptista, Colloids Surf., B 77 (2010) 122.
[19] J. B. Kaper, J. P.Nataro, H. L. T.Mobley, Nature Reviews, 2 (2004) 123.
[20] X. Mao, L. Yang, X.-L. Su, Y. Li, Biosens. Bioelectron., 21 (2006) 1178.
[21] L. C. Shriver-Lake, S. Turner, C. R. Taitt, Anal. Chim. Acta, 584 (2007) 66.

[22] I. L. Medintz, H. T. Uyeda, E. R. Goldman, H. Mattoussi, Nat. Mater., 4 (2005) 435.
[23] A. Son, D. Dosev, M. Nichkova, Z. Ma, I. M. Kennedy, K. M. Scow, K. R. Hristova, Anal. Biochem., 370 (2007) 186.
[24] A. Son, A. Dhirapong, D. K. Dosev, I. M. Kennedy, R. H. Weiss, K. R. Hristova, Anal. Bioanal. Chem., 390 (2008) 1892.
[25] H. Wang, J. Wang, C. Timchalk, Y. Lin, Anal. Chem., 80 (2008) 8477.
[26] V. K. Sharma, E. A. Dean-Nystrom, T. A. Casey, Mol. Cell. Probes 13 (1999) 291.
[27] J. Ripp, Analytical Detection Limit Guidance in: T. D.o.N. Resources (Ed.), Wisconsin, 1996.
[28] C. M. Carey, M. Kostrzynska, S. Thompson, J. Microbiol. Methods, 77 (2009) 235.
[29] J. A. Ferguson, F. J. Steemers, D. R. Walt, Anal. Chem., 72 (2000) 5618.
[30] Q. Dai, X. Liu, J. Coutts, L. Austin, Q. Huo, J. Am. Chem. Soc., 130 (2008) 8138.
[31] C.-H. Liu, Z.-P. Li, B.-A. Du, X.-R. Duan, Y.-C. Wang, Anal. Chem., 78 (2006) 3738.
[32] F. Patolsky, Y. Weizmann, E. Katz, I. Willner, Angew. Chem. Int. Ed., 42 (2003) 2372.
[33] J. J. Storhoff, S. S. Marla, P. Bao, S. Hagenow, H. Mehta, A. Lucas, V. Garimella, T. Patno, W. Buckingham, W. Cork, U. R. Müller, Biosens. Bioelectron., 19 (2004) 875.
[34] P. S. Eastman, W. Ruan, M. Doctolero, R. Nuttall, G.d. Feo, J. S. Park, J. S.F. Chu, P. Cooke, J. W. Gray, S. Li, F. F. Chen, Nano Lett., 6 (2006) 1059.
[35] J. Tuttle, T. Gomez, M. P. Doyle, J. G. Wells, T. Zhao, R. V. Tauxe, P. M. Griffin, Epidemiol. Infect., 122 (1999) 185.
[37] X.-L. Su, Y. Li, Anal. Chem., 76 (2004) 4806.
[38] L. Yang, Y. Li, G. F. Erf, Anal. Chem., 76 (2004) 1107.
[39] S. Huang, P. Pang, X. Xiao, L. He, Q. Cai, C. A. Grimes, Sens. Actuators, B 131 (2008) 489.
[40] X. Xue, J. Pan, H. Xie, J. Wang, S. Zhang, Talanta, 77 (2009) 1808.
[41] J. G. Bruno, T. Phillips, M. P. Carrillo, R. Crowell, J. Fluoresc., 19 (2009) 427.
[42] N. V. Zaytseva, R. A. Montagna, A. J. Baeumner, Anal. Chem., 77 (2005) 7520.

Example 2

We have demonstrated in-situ monitoring capability of inhibitor resistant gene quantification assay using magnetic bead (MB) and quantum dot (QD) nanoparticle (hereafter "MB-QD assay") for the detection of E. coli O157:H7. in environmental samples. The selectivity of the MB-QD assay was demonstrated via the discrimination of the target bacteria in the presence of nonspecific microbal populations. The effect of temperature on the assay was examined to evaluate the necessity of elevated temperature incubation. The reagents (i.e., particle complex and particle-DNA conjugate) were also shown to have a stability of at least 10 days without refrigeration, therefore enabling prior preparation and the subsequent storage of these reagents. In addition, it was found that the MB-QD assay was resistant to the presence of naturally occurring inhibitors (i.e., humic acids, $Ca^{2+}$) and residual reagents from DNA extraction (i.e., surfactant, ethanol). Overall the results indicated that the MB-QD assay is suitable as an in-situ bacteria monitoring method for working with inhibitor laden samples without requiring additional purification steps and elevated temperature process.

Introduction

E. coli are common bacteria in the intestines of human and warm-blooded animals and most of the strains are harmless. However, some groups of E. coli are the causative agents of many enteric infections worldwide. Among the hundreds of strains of the bacterium E. coli, the pathogenic E. coli O157:H7 is of particular interest. Ever since E. coli O157:H7 was first discovered in 1982, it has been the most common pathogenic E. coli seen in the United States[1]. E. coli O157:H7 is a food-borne pathogenic bacterium that poses a significant concern in water supply systems[2-4].

In order to detect the presence of pathogens and to predict the safety in environment, the availability of a pathogen detection system for real environmental samples will be necessary[5,6]. The detection system can potentially operate autonomously and perform measurement regularly to deliver high resolution temporal data and to issue advance warning on contamination. However, the development of such an pathogen detection system is contingent on the availability of an inhibitor resistant, robust and economically viable detection technique which can work with minimally prepared and inhibitor-laden samples. In this case, a robust technique will imply minimal dependence on elevated temperature processes as well as ability to prepare and store necessary reagents ahead of time.

Recent improvement of biotechnology and genomics has enabled new development in DNA detection technology that is based on DNA amplification. Amplification techniques such as real-time PCR were developed for pathogen detection including including E. coli O157:H7[7,8]. It has a relatively wide quantification range of more than 5 orders of magnitude[9] and a low detection limit[10,11]. However, it is difficult to lend the PCR-based method to minimally prepared environmental samples due to its susceptibility to contamination, which will result in either the amplification of undesired DNA along with the target DNA[12,13] or the incomplete amplification due to the inhibitory mechanisms[14-16]. In order to avoid the PCR inhibition due to contamination, field samples have to undergo extensive preparation in a laboratory environment. Owing to its vulnerability to contamination that is typical of gene amplification technique, the real-time PCR requires extensive steps and apparatus, including a clean bench. Therefore PCR based techniques, in its current state, may not be ideal for further development into an in-situ capable method.

The ideal technique for in-situ bacterial monitoring must be able to maintain 1) its selectivity in the presence of other phylogenetically similar bacteria. 2) Its sensitivity should be also comparable or better than that of the real-time PCR such that it can detect the minimum infectious does, which are 100 organisms per mL water for E. coli O157:H7[17,18]. 3). The technique would be viable for ambient temperature incubation, which will reduce the complexity of the apparatus required for using the technique outside a laboratory setting. 4) A relatively short analysis time (e.g., hours) from sample injection to pathogen quantification is also critical for effective monitoring. In other words, there should be minimal processing steps from sample injection to quantification. 5) The reagents used in the technique must be stable over a range of temperatures for extended time in order to prepare them in advance and to avoid reagent preparation at the sampling site. 6) Most importantly, the technique should be resistant to a number of contaminants and inhibitors (e.g., humic acids, cations) that are present in a large amount in environmental samples. These naturally occurring compounds behave as inhibitors to the gene quantification methods such as real-time PCR assay[19-26] and in general it is difficult to remove these inhibitors from the sample matrix[27,28]. Another type of interference to the reaction is the residual reagents (e.g., surfactant, ethanol) from nucleic acid extraction. These inhibitors are well known to be detrimental to the amplification based assay[15,29].

Figure 9:
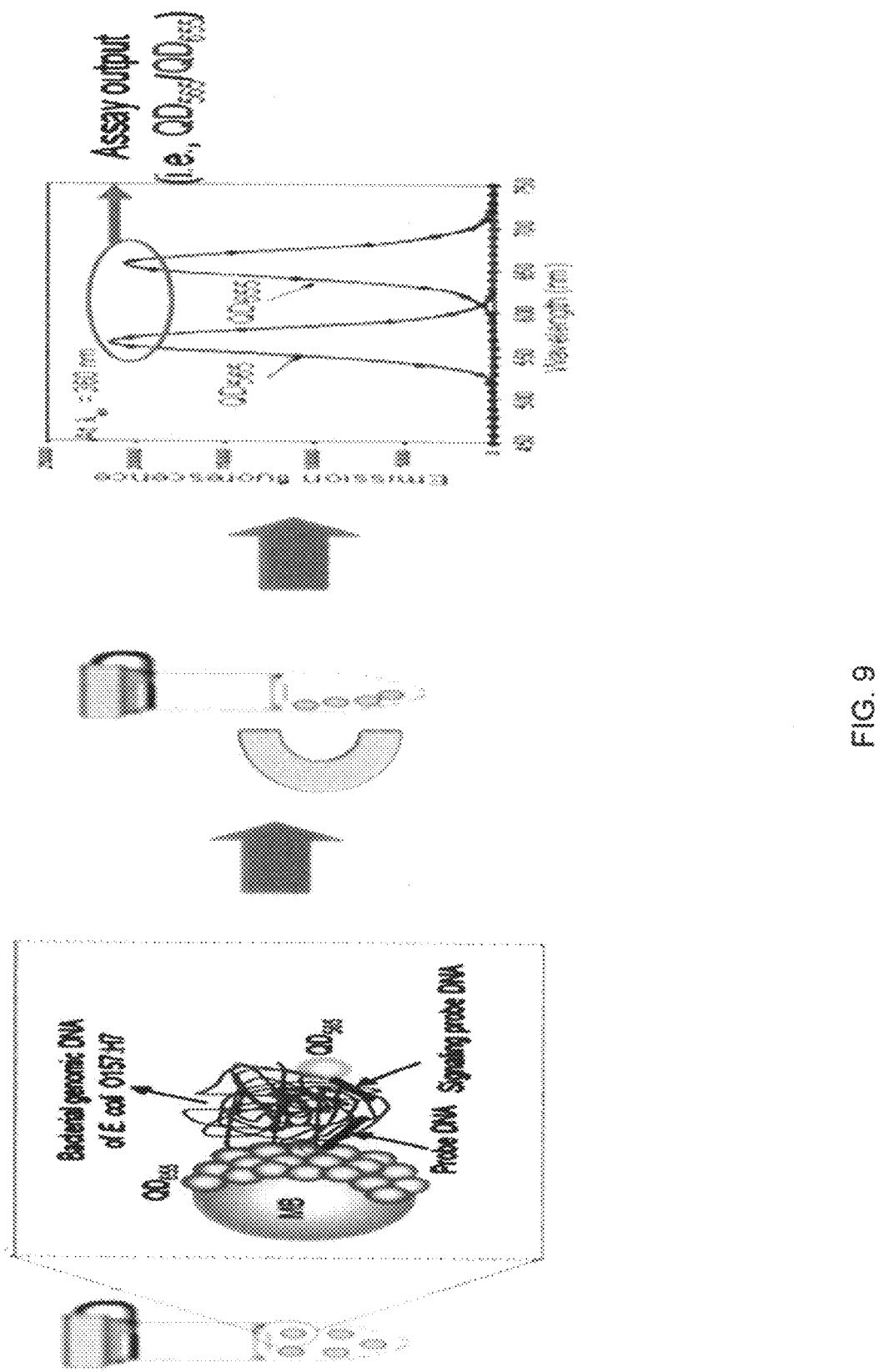
FIG. 9 is a schematic diagram of an embodiment of the gene quantification assay using MB and a set of QD nanoparticles (MB-QD assay). The first step illustrates sandwich hybridization of target DNA with probe and signalling probe DNAs conjugated with MB-$QD_{655}$ and $QD_{565}$, respectively. The second step illustrates separation of the DNA-particle hybrids by magnetic application. Finally, a graph illustrates fluorescence measurement.

The present disclosure relates to a new type of gene quantification technique based on solution hybridization using magnetic bead-quantum dots nanoparticles (hereafter, "MB-QD assay") (FIG. 9). This technique has demonstrated detection limits of both about 890 zeptomolar ($10^{-21}$ M) concentration of ssDNA and 87 gene copies of dsDNA[30]. In addition, the MB-QD assay was able to detect $E.\ coli$ O157:H7 with about 25 CFU/mL of the LOD which is below the minimum infectious dose[17,31]. In this prior proof-of-concept study[30], the quantification capability such as sensitivity and selectivity was demonstrated in an ideal laboratory setting with an elevated temperature incubation, freshly prepared reagents and the absence of contaminants in the test samples. More importantly, prior studies[32-34] pertaining to other gene quantification techniques in general were often demonstrated in the context of an ideal laboratory setting. In other words, these techniques have not demonstrated their potential to be used in a non-laboratory environment.

The present disclosure involves the MB-QD assay for non-laboratory environment usage, in particular its inhibitor resistance and eventual in-situ monitoring capability with consideration to the criteria as described above. This understanding is at the core of the further development of our new bioassay into a well-designed, in-situ capable engineered system. This system will be a valuable tool for the reliable assessment of environment. The present disclosure includes 1) selectivity of the assay in the presence of nonspecific microorganisms; 2) temperature effect on the assay along with kinetics (i.e., time factor); 3) stability of reagents over time and necessity of mechanical agitation device; 4) resistance to naturally occurring inhibitors and residual reagents from DNA extraction as compared to the real-time PCR assay.

Materials and Methods

MB-QD Assay

The recent study by Kim and Son[30] described the details of the MB-QD assay and the corresponding materials used. The procedure of MB-QD assay used for the current study is summarized below. Note that the MB-QD assay procedures including the types and concentrations of reagents have been previously optimized[30]. The schematic diagram of the gene quantification assay using MB and QD is represented in FIG. 9.

$E.\ coli$ O157:H7 Culture and gDNA Extraction.

The $E.\ coli$ O157:H7 strain was purchased from American Type Culture Collection (ATCC, Manassas, Va.) and cultured in trypticase soy broth at 37° C. The genomic DNA (gDNA) was extracted from the overnight culture of $E.\ coli$ by FastDNA® SPIN for Soil kit (MP Biomedicals, Solon, Ohio). DNA concentration and purity were determined by UV absorption at 260 nm and 280 nm using Nanodrop ND-1000 spectrophotometer (Nanodrop Technologies, Wilmington, Del.).

DNA Hybridization.

The DNA oligoprobes targeting eaeA gene (Genbank accession: X60439.1) of $E.\ coli$ O157:H7 were designed and synthesized (IDT, Coralville, Iowa). The DNA sequences of both probe and signaling probe DNAs, which are hybridized with the gDNA of $E.\ coli$ O157:H7, are as follows: probe DNA sequence is SEQ ID NO: 1 5'-NH$_2$—CGGATAA-GACTTCGG CTAAA-3' and signaling probe DNA sequence is SEQ ID NO: 3 5'-CTTAT ACCGCGACGGTGAAA-NH$_2$-3' (the complementary sequences to the target DNA in both probe DNAs are in bold). The target DNA region (151 bp) defined by both probe DNAs corresponds to 1896-2047 in eaeA gene (X60439.1). The aminated MBs (Dynabead M270, Invitrogen, Carlsdad, Calif.) were encapsulated with carboxyl CdSe/ZnS quantum dot nanoparticles (QD$_{655}$, Invitrogen) by forming an amide covalent bond. Both aminated probe and signaling probe DNAs were also respectively labeled with the MB-QD$_{565}$ complex and another type of quantum dot nanoparticles (QD$_{565}$). After immobilizing QD$_{655}$ (about 2 μM, 8 μL) on the surface of MB (about 2×10$^7$ beads mL$^{-1}$), it was conjugated with the probe DNA (about 500 μmoles). The signaling probe DNA (about 160 μmoles) was covalently labeled with QD$_{565}$ (about 2 μM, 8 μL) and subsequently incubated in NaBH$_4$. Its purpose is to serve as a blocking solution to deactivate the remaining functional groups of nanoparticles. The gDNA of $E.\ coli$ O157:H7 was denatured by sonication and high-temperature incubation (about 95° C.) prior to the hybridization. The denatured form of target gDNA was hybridized with MB-QD$_{655}$-probe DNA and QD$_{565}$-signaling probe DNA at about 37° C. using a gentle tilt rotation. Prior to fluorescence measurement, the DNA-particle hybrids were subsequently separated by the magnet (MPC®-96S, Invitrogen) and washed three times with phosphate buffer.

Fluorescence Detection.

The quantification output of the MB-QD assay was obtained via the QDs fluorescence. The florescence was measured by a Spectramax M2 microplate reader (MDS, Sunnyvale, Calif.). Respective endpoint emission wavelength ($\lambda_m$) for QD$_{565}$ and QD$_{655}$ at a single excitation wavelength (i.e., $\lambda_{ex}$=360 nm) was 570 nm and 660 nm. The fluorescence of QD$_{565}$ was subsequently normalized (i.e., QD$_{565}$/QD$_{655}$) by that of QD$_{655}$ to account for the different number of nanoparticles that were captured in each reaction.

Specificity, Kinetics, and Stability of Assay

Various parameters were tested to investigate the feasibility of MB-QD assay for in-situ appliation.

Specificity.

The specificity of the MB-QD assay was demonstrated by quantifying the eaeA gene of $E.\ coli$ O157:H7's gDNA from a mixed pool of target and non-target gDNA. Mixed (non-target) microorganisms were obtained from the mixed liquor in the aeration basin of an activated sludge process (Auburn wastewater treatment plant, Auburn, Ala.). Both gDNA extracted from pure $E.\ coli$ O157:H7 and mixed liquor samples were mixed in various ratios (about 0, 40, 160, and 400 ng of $E.\ coli$ gDNA per reaction and 0, 80, and 400 ng of activated sludge gDNA per reaction). The gDNA mixture was denatured and used for the subsequent DNA hybridization.

Kinetics.

Kinetic experiments were used to investigate the MB-QD assay's performance at ambient temperature. About 40 ng of gDNA per reaction was hybridized at about 15, 25, and 37° C. Normalized fluorescence (i.e., QD$_{565}$/QD$_{655}$) was measured at about 0.5, 1, 2, 4, 6, and 8 h. Kinetic order was determined via the R$^2$ values of regression equations for various kinetic reactions. The hybridization capability (%) was calculated based on the assumption that 100% of gDNA hybridization was achieved under the continuous agitation. The effect and necessity of mechanical agitation on the gDNA hybridization was also investigated. About 40 ng of gDNA per reaction was hybridized at about 37° C. for about 8 h with three different mixing conditions: continuous agitation, pulsed agitation (i.e., agitation for only 10 min in every 2 h), and no agitation. The hybridization capability (%) was calculated based on the assumption that 100% of gDNA hybridization was achieved under the continuous agitation.

Stability.

The stability of the MB-QD particle complex was examined under various storage conditions (i.e., ambient and refrigeration temperature). Storage stability will enable reagent to be prepared in advance and stored prior to DNA hybridization. Pre-incubations for covalent bonds formation are required for making MB-QD particle complex and immobilizing probe DNA on QDs. $QD_{655}$ only and MB-$QD_{655}$ complex were stored in phosphate buffer at about 4° C. and ambient temperature for about 30 days. The storage stability was monitored by measuring the fluorescence of $QD_{655}$ for the MB-$QD_{655}$ complex. The stability of MB-$QD_{655}$ indicates the covalent bonding stability between particles. The fluorescence of $QD_{655}$ itself was also monitored simultaneously to investigate the photobleaching effect of QD nanoparticles.

Assay Interference Test

Four types of inhibiting compounds were used to examine the robustness of the MB-QD assay in the presence of contaminants. These compounds are either abundant in the environment (i.e., humic acids and $Ca^{2+}$) or employed in the nucleic acid extraction (i.e., sodium dodecyl sulfate (SDS) and ethanol). Commercially available humic acids were used for the experiment. Per manufacturer's specifications (Aldrich, St. Louis, Mo.), the humic acids originated from decomposition of dead plant and its molecular composition includes polysaccharides, proteins, simple phenols and chelated metal ions. Humic acids (about 0.0001, 0.01, 0.1, 1, 10, and 100 ng $\mu L^{-1}$ of reaction), $CaCl_2$ (about 1, 5, 10, 50, and 100 mM), SDS (about 0.0001, 0.0001, 0.01, 0.1, and 1%, v/v), and ethanol (about 0.01, 0.1, 1, 2, and 5%, v/v) were added to the hybridization buffer. The buffer was subsequently used for the hybridization of MB-QD assay where about 800 ng of gDNA of E. coli O157:H7 per about 400 µL reaction (i.e., about 2 ng $\mu L^{-1}$ reaction) were added as a template. The interference test output was represented by the quantification capability (%). It was determined by the ratio (i.e., $F_{w, inhibitor}/F_{w/o}$ inhibitor) of the fluorescence in the presence and absence of inhibitors.

Real-Time PCR Assay.

Real-time PCR assays were used to study the relative inhibitory effects of four compounds as described above. The standard templates of eaeA gene for real-time PCR assay were generated by $PCR^2$ and the subsequent serial dilution of PCR amplicons (i.e., 2×10 to 2×10$^9$). The reaction mixture includes 1×Universal SYBR Green master mix (Applied Biosystems, Foster City, Calif.), about 0.5 µM of eaeA targeting forward and reverse primers (forward SEQ ID NO: 5: 5'-GGCGGATAAGACTTCGGCTA-3', reverse SEQ ID NO: 7: 5'-CGTTT TGGCACTATTTGCCC-3'), about 2 µL of standard or sample DNA template, and filter-sterilized DNase/RNase free water (GIBCO®, Invitrogen) to bring the final reaction volume to about 25 $\mu L^{35}$. In parallel to MB-QD assay, the same amount of four inhibitors (i.e., humic acids, $CaCl_2$, SDS, and ethanol) was added to the PCR reaction mixture containing about 50 ng of gDNA per about 25 µL of reaction (i.e., about 2 ng $\mu L^{-1}$ of reaction). The concentrations of inhibitors (ng $\mu L^{-1}$ of reaction) were calculated based on the total volume. The real-time PCR reaction was performed using StepOne™ Real-Time PCR system (Applied Biosystems) based on the thermal cycles presented by Carey et al.[36]. Following PCR amplification, melting curve analysis of amplified DNA products was performed to confirm product purity with the temperature at a rate of about 0.3° C. $s^{-1}$ from about 55° C. to 95° C. The quantification capability (%) of real-time PCR assay was obtained by the ratio of gene copies determined in the presence and absence of inhibitors.

Results and Discussion

Specificity of Assay

Figure 10:
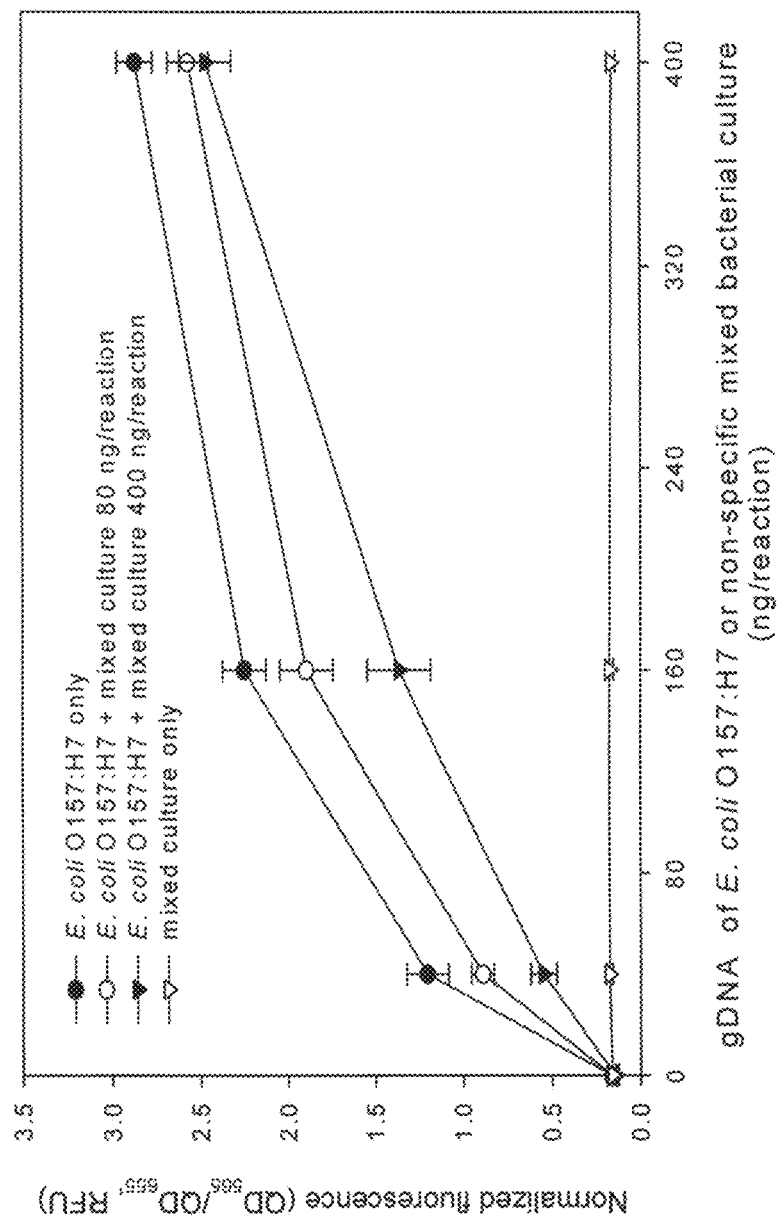
FIG. 10 is a graph that illustrates specificity of an embodiment of the MB-QD assay. The ability of assay that can specifically detect eaeA gene was demonstrated in the presence of non-specific gDNA in the hybridization reaction. The signal and error bars represent mean and standard deviation based on five measurements of fluorescence. The same description regarding the error bars applies to FIGS. 10 through 13.

The sensitivity of the assay has been previously demonstrated for both ssDNA and dsDNA[30]. In this study, the specificity of the MB-QD assay was examined by using the gDNA mixture of both E. coli O157:H7 and mixed microbial cultures in activated sludge. The result is presented in FIG. 10. The gDNA of activated sludge was used as a negative control, and it had a negligible fluorescence signal. In other words, the MB-QD-probe did not capture any non-target gDNA during hybridization. Various amounts of non-target gDNA (e.g., about 0, 80, 400 ng reaction$^{-1}$) were mixed with the target gDNA (e.g., about 0, 40, 160, 400 ng reaction$^{-1}$) to simulate real environmental condition. The assay output decreased about 50% of initial fluorescence signal as the amount of non-target gDNA increased from about 0 to 160 ng/reaction. However, the assay output was almost recovered at the about 400 ng of target gDNA per reaction. Although not intendint to be bound by any particular theory, it seems that the hybridization kinetics of target gDNA in the presence of nonspecific target may affect the quantification output of assay.

The Effect of Temperature and Mixing Condition

Figure 11:
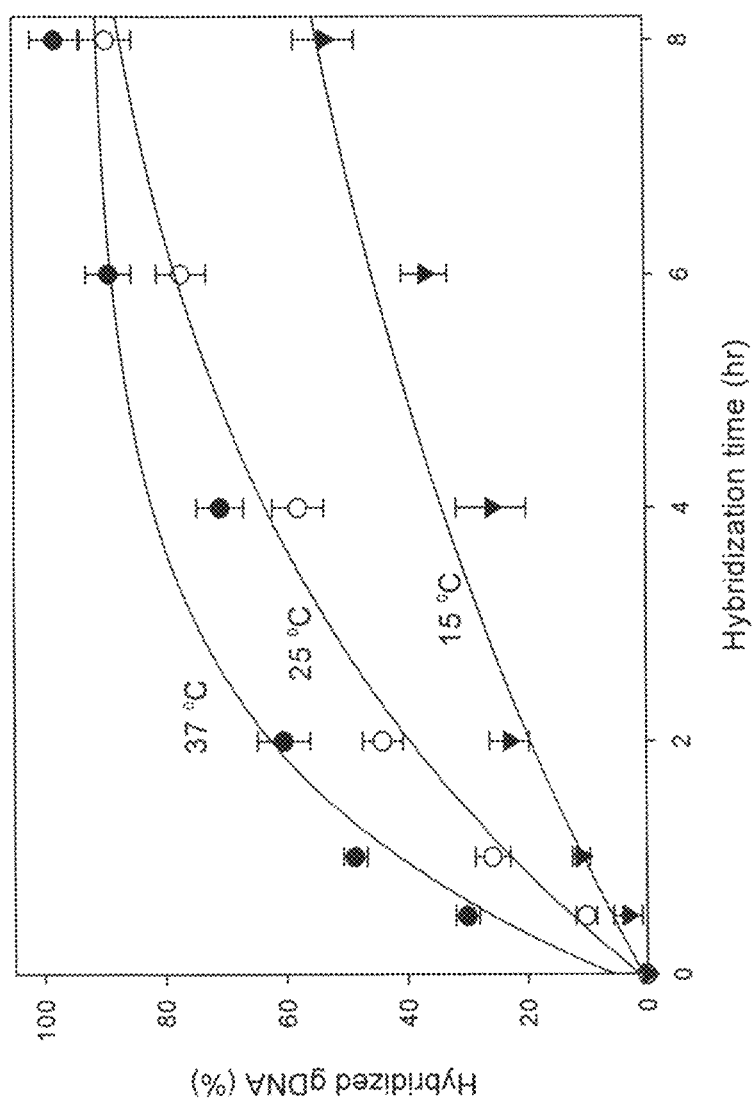
FIG. 11 is a graph that illustrates the effect of various temperatures on the DNA hybridization kinetics.

In order to examine the suitability of the MB-QD assay for on-site measurement without the benefit of an incubator, kinetic experiments were performed with the target gDNA at three different temperatures: about 15, 25 (i.e., ambient condition), and 37° C. The three temperatures were selected to represent ambient temperature in different regions. FIG. 11 shows the hybridized amount of gDNA at various temperatures for about 8 hours. The y-axis of FIG. 11 indicated the relative hybridized amount of gDNA (%). In order to better visualize the kinetic result, the concentration unit of hybridized gDNA was converted to the percentile unit. The amount of hybridized gDNA at about 37° C. and about 8 h was assumed to be the maximum possible for hybridization, since it was shown as the plateau (i.e., reaching the equilibrium) in the original kinetic plot. Thus, the gDNA value at about 37° C. and about 8 h was assumed to represent 100% hybridization. Although the higher temperature accelerates the gDNA hybridization process, the gDNA hybridization could also be achieved at the ambient temperature or lower. For example, at the temperature of about 25° C., about 3 h was required to achieve 50% hybridization. At about 15° C., 50% hybridization was achieved after about 8 h incubation. The hybridization rate constants measured from the linear regression analysis using the second-order kinetic model[37-39] are shown in Table 1. Since the target concentration is another rate-limiting factor in a hybridization reaction based on the second order kinetics, the hybridization efficiency at ambient temperature can be increased by using a higher amount of target gDNA. This kinetic result indicates that hybridization incubator may not be required for the MB-QD assay as DNA hybridization can also be achieved at ambient temperature.

TABLE 1

The hybridization rate constants ($k_h$) and the correlation co-efficient ($R^2$) measured by the linear regression analysis based on the second order kinetics model.

| | Second-order kinetics | |
|---|---|---|
| Temperature (° C.) | $k_h$ (×10$^6$ M$^{-1}$ h$^{-1}$) | $R^2$ |
| 25 | 0.140 | 0.991 |
| 37 | 0.571 | 0.943 |
| 42 | 0.643 | 0.964 |

Figure 12:
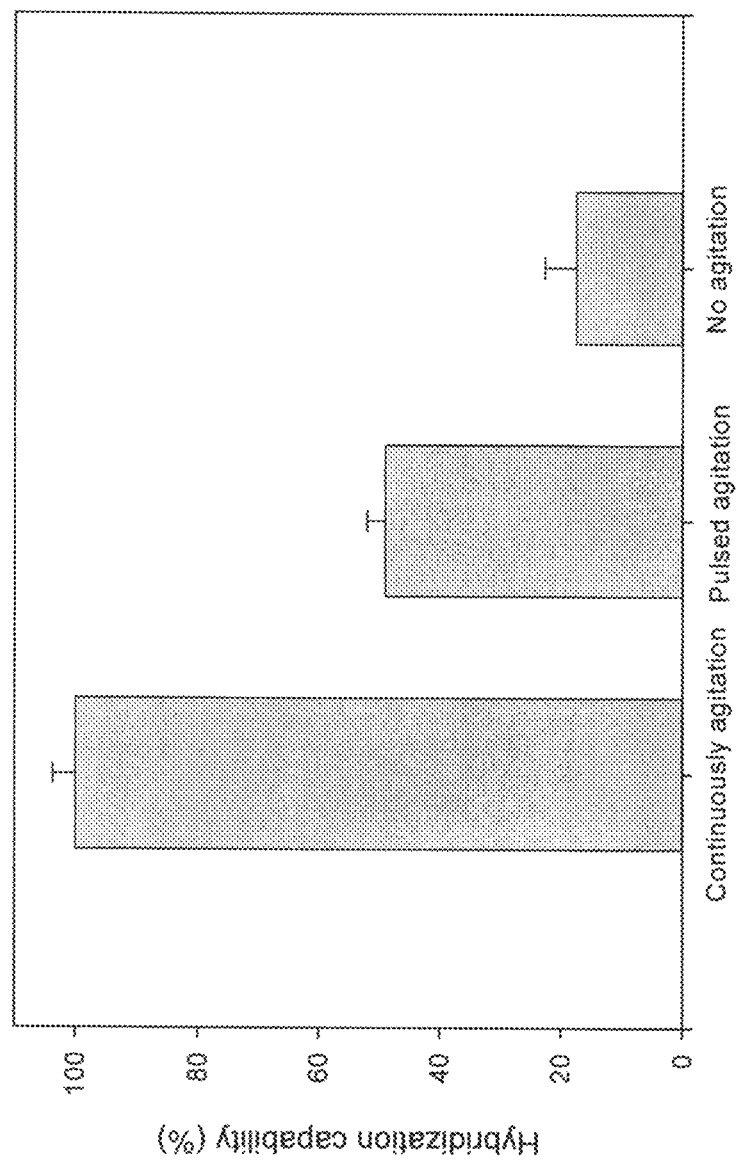
FIG. 12 is a graph that illustrates the effect of mechanical strength agitation on the DNA hybridization efficiency.

Thorough mixing is also beneficial for the successful DNA hybridization (FIG. 12). Compared to the amount of hybridization achieved via continuous agitation for about 8 h, 20% hybridization was achieved without agitation and 50% of gDNA was hybridized using pulsed agitation. It is interesting to note that 50% hybridization is achieved with about 10 minutes agitation every about 2 h for a total of about 8 h. This finding can be beneficial for actual on-site application where the agitation device is not available.

Stability of Reagents

Figure 13:
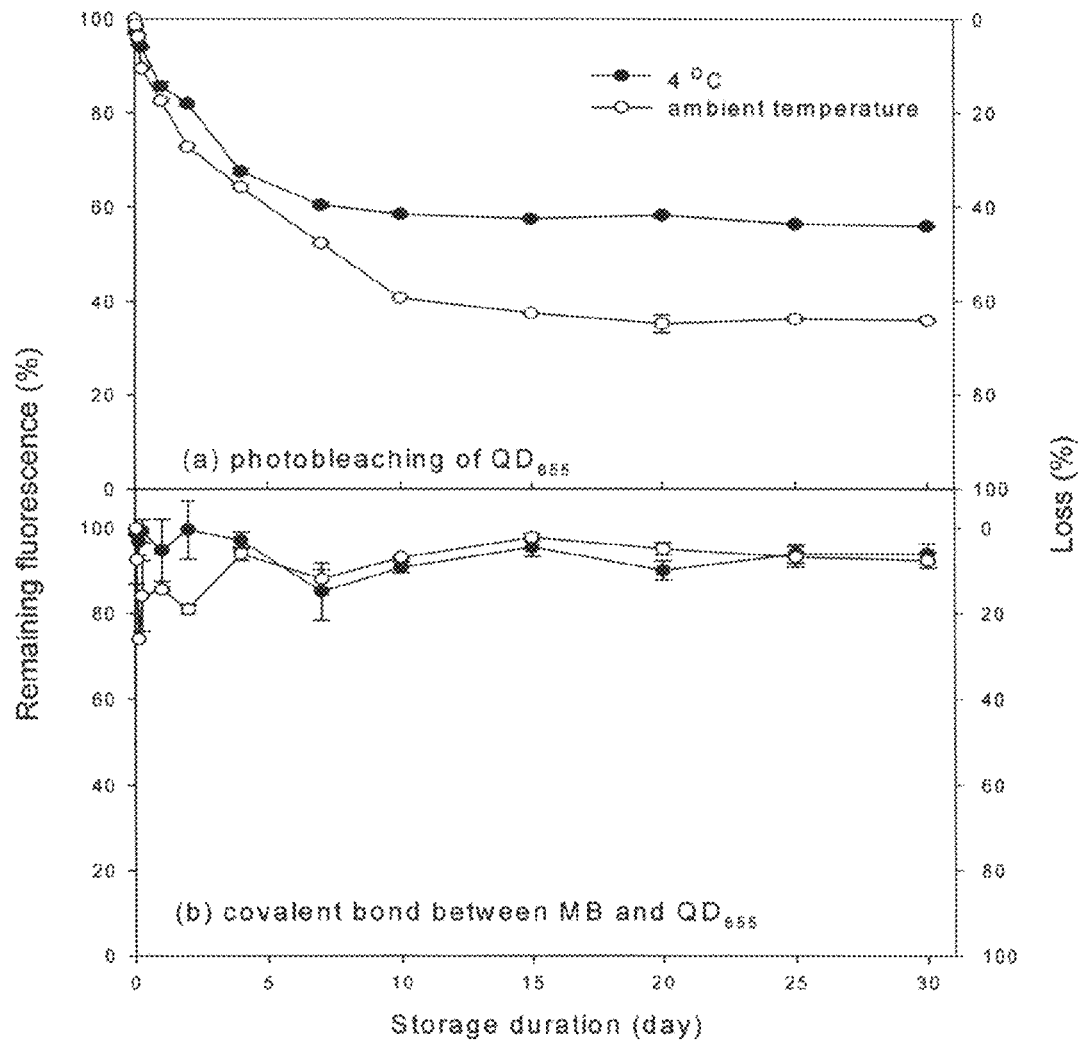
FIGS. 13A-B are graphs that illustrate the stability of reagents: (A) photobleaching effect of $QD_{655}$ and (B) covalent bond between MB and $QD_{655}$ at both ambient and refrigeration (4° C.) temperature. The change of fluorescence (y-axis) observed for the storage duration (x-axis) is presented in percentage relative to initial fluorescence value.

In order to observe the stability of reagents used for DNA hybridization, the stability of covalent bonding and the photobleaching effect of labels were monitored at two temperature conditions (ambient and about 4° C.) for about 30 days. FIG. 13a shows the photobleaching effect of $QD_{655}$ at two different storage temperatures over time for about 30 days. After about 10 days, the fluorescence of the QDs was at about 60% and 40% of the initial value at about 4° C. and ambient temperature, respectively. The remained intensity subsequently sustained for the last about 20 days. The covalent bond between MB and $QD_{655}$ was observed to be stable for about 30 days. Its fluorescence intensity remained over about 80% throughout the experiment (FIG. 13b). The remaining fluorescence (%) in the y-axis of FIG. 13b was obtained based on the subtraction of the fluorescence loss by photobleaching (FIG. 13a) from the total fluorescence loss. It is interesting to note that temperature is not an important factor for the stability of the covalent bonding. The stability of covalent bonding is more critical for the assay performance than the photobleaching of QDs. If the covalent bond between MB and QDs is disrupted, the magnetic separation may not yield the QD-DNA hybrids. The incomplete separation of hybrids will result in poor quantification by the assay.

Based on our findings, the covalent bonds between particle-particle is stable (i.e., maintain at least about 80% of the fluorescence) at about ambient temperature for about a month. The fluorescence intensity of QD label decreased due to the natural photobleaching: however, it is still acceptable to use QDs as photostable labels for storage duration of minimum abut 10 days. Therefore, the reagents of the MB-QD assay (i.e., particle complex and particle-DNA conjugate) can be prepared ahead of time and stored for a minimum of about 10 days without the need of refrigeration. Producing all of the reagents for the MB-QD assay requires about 6 h. The MB-QD assay requires about 8 h to perform for DNA hybridization and detection at about 25 and 37° C. In total, reagent synthesis, probe preparation and detection require about 1 day. It should be noted that the particle reagents can be stored at about 4° C. for weeks at a time, the total assay time will be decreased to about 8 h.

Assay Interference Test

The applicability of the MB-QD assay to environmental samples was demonstrated by its inhibitors resistance. The inhibitory change of gene quantification capability for both MB-QD and real-time PCR assays targeting gDNAs in the presence of four inhibitors is shown in FIGS. 14a-d. Here, the pure target gDNA was spiked with four inhibitors to simulate environmentally contaminated sample before purification. The incubation of four inhibitors without gDNA (i.e., negative control) resulted in no significant fluorescence signal. It indicated that the inhibitors did not behave like the target DNA which hybridizes with probe DNA. In other words, the inhibitors did not mimic gDNA as target material in the MB-QD assay.

Humic Acids.

Figure 14:
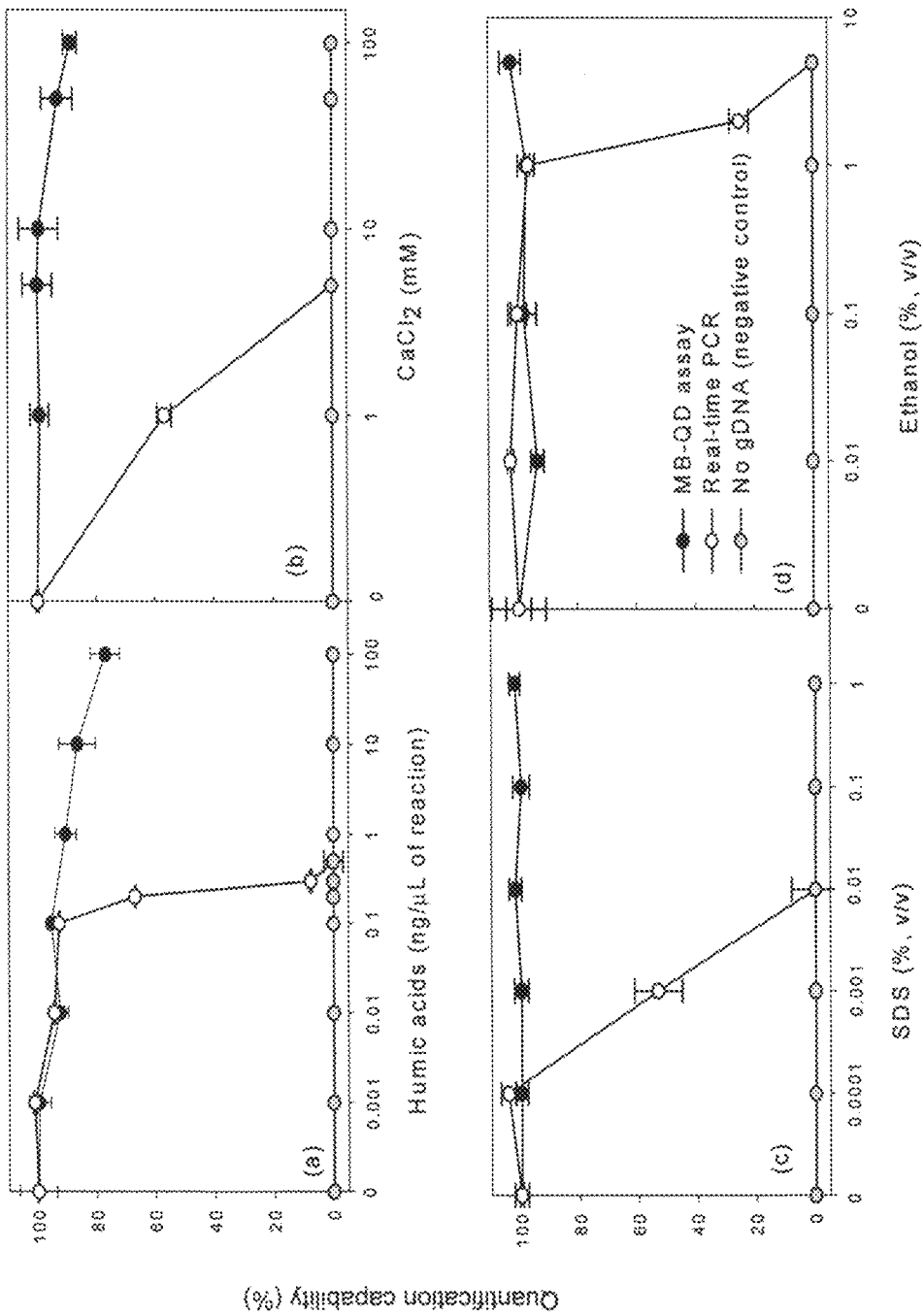
FIGS. 14A-D are graphs that illustrate the inhibitory change of gene quantification capability for both MB-QD assay and real-time PCR assay in the presence of various inhibitors: humic acids, $CaCl_2$, SDS, and ethanol. Gene quantifications targeting eaeA gene in pure $E.\ coli$ O157:H7 bacterial gDNA were performed by measuring the normalized fluorescence (i.e., $QD_{565}/QD_{655}$) and the gene copies for MB-QD assay and real-time assay, respectively. The same amount of gDNA template (i.e., 2 ng $\mu L^{-1}$ of reaction) was used to compare both assays and no gDNA was added to the negative control. The inhibition effects on the gene quantification in both assays were observed for the various inhibitor concentrations (x-axis). The quantity of gene was expressed in percentile (y-axis) relative to inhibitor-free conditions.

The effect of various amounts of humic acids on the MB-QD assay was observed. Due to the ubiquity and abundance of humic acids in the environment, they are often co-extracted along with the nucleic acids from soil, sediment, and water samples[27]. Humic acids can be partially removed by time-consuming purification techniques, and the complete removal of humic acids from the sample is nearly impossible. During the extensive purification technique of humic acids, DNA loss is also common[28]. The presence of humic acids has drastically decreased the quantification efficiency of real-time PCR assays[19-24]. We found that the MB-QD assay is resistant to humic acids (FIG. 14a). Even though the output (fluorescence) of MB-QD assay slightly decreased (from about 100% to 80%) at the high concentration of humic acids (about 100 ng per μL reaction), it maintained the linearity of gene quantification at all concentration ranges of humic acids. In comparison to the presented MB-QD assay, the real-time PCR assay was completely inhibited by humic acids at more than about 1 ng per μL reaction although it showed no inhibition (i.e., about 100% of output) in the low concentration range of humic acids (i.e., about 0.001-0.1 ng $\mu L^{-1}$ of reaction). Although not intending to be bound by any particular theory, the inhibition mechanisms of humic acids in real-time PCR assay may be due to the inhibited Taq polymerase by humic acids[28,40] and/or complexation of humic acids with $Mg^{2+}$ ions. $Mg^{2+}$ are vital cofactor for Taq polymerase in the PCR reaction[41]. As compared to the real-time PCR assay, the MB-QD assay maintained stable signals at the corresponding concentration of humic acids. More than 90% of the quantification capability was maintained without the drastic change of assay output. Overall, the MB-QD assay is more suitable for the environmental samples that contain high levels of humic acids than the real-time PCR assay.

Multivalent Ions.

Calcium is one of the abundant cations in the environment because of its natural occurrence in the earth's crust. The river in lime areas may contain amounts of $Ca^{2+}$ as high as 100 ppm (i.e., 2.5 mM)[42]. Since there is a possibility of $Ca^{2+}$ to be carried over from environmental samples to the extracted gDNA, the inhibitory effect of $Ca^{2+}$ was examined for both the MB-QD assay and real-time PCR assay. The output of the MB-QD assay was found to be stable for the entire range of $Ca^{2+}$ concentration tested (i.e., about 1-100 mM). This indicates that there is no major inhibitive effect of amplification reaction failed (i.e., zero signal) at a concentration of more than about 5 mM of $Ca^{2+}$ and only about 60% of the quantification was achieved at about 1 mM of $Ca^{2+}$. This is mainly due to the competitive interaction of $Ca^{2+}$ with $Mg^{2+}$, which is the vital cofactor for Taq polymerase in PCR reactions[43]. Recent literature also indicated that the high concentration of divalent cations such as $Ca^{2+}$ can induce a decrease (i.e, bleaching) in the fluorescence values of organic fluorophore dye[25]. Hybridization based MB-QD assay recruit neither polymerase nor organic fluorophores. Thus, the MB-QD assay is more suitable than real-time PCR for the samples from an environment with large quantities of multivalent cations.

SDS and Ethanol.

DNA extraction step is performed prior to the MB-QD assay. Residual amount of reagents used for DNA extraction may remain in the gDNA and may impair gene quantification[25,26]. In order to examine the effect of residual reagents on the gene quantification, varying amounts of SDS and ethanol were added to the hybridization reaction. The assay was severely inhibited by the presence of $Ca^{2+}$. $Ca^{2+}$ for the MB-QD assay. In comparison, the real-time PCR quantification output of the MB-QD assay was consistently maintained without any inhibition over the range of SDS (i.e., about 0.001-1%, v/v) used (FIG. 14c). However, the real-time PCR assay was severely inhibited by SDS. The amplification reaction completely failed at over about 0.01% SDS concentration. Even the lowest amount of SDS (i.e., about 0.001%) can cause about 50% inhibition of the real-time PCR assay. The FIG. 14d shows that the MB-QD assay continued to function with the presence of increasing ethanol concentration. In contrast, the real-time PCR assay was completely inhibited by about 5% ethanol and about 60% inhibited by about 2% ethanol. No inhibition was observed at the lower range of ethanol concentration (about 0.01-1%). The results indicated that the MB-QD assay can be used directly on gDNA extracted from environmental samples without further purification steps.

Conclusions

In summary, the MB-QD assay is resistant to contaminants such as humic acids and cations, which commonly exist in environmental samples. The MB-QD assay also appeared to be stable in the presence of residual reagents such as surfactant and ethanol, which can be carried over from DNA extraction. In comparison, real-time PCR has shown major inhibitions by the presence of the four compounds. Consequently, the MB-QD assay is more appropriate than real-time PCR for samples that are laden with contaminants and inhibitors. Further work pertaining to the inhibition mechanisms on the gene quantification will be necessary to eventually develop the MB-QD assay for in-situ application.

REFERENCES

Which are Herein Incorporated by Reference

1. P. S. Mead, L. Slutsker, V. Dietz, L. F. McCaig, J. S. Bresee, C. Shapiro, P. M. Griffin and R. V. Tauxe, *Emerg. Infect. Dis.*, 1999, 5, 607-625.
2. D. S. Francy and R. A. Darner, *Wat. Res.* 2000, 34, 2770-2778.
3. R. Girones, M. A. Ferrús, J. Alonso, J. Rodriguez-Manzano, B. Calgua, A. A. Corrêa, A. Hundesa, A. Carratala, S. Bofill-Mas, *Wat. Res.* 2010, 44, 4325-4339.
4. J. L. Sedillo, A. Quintana, K. Souza, K. H. Oshima, G. B. Smith, *J. Environ. Monit.*, 2008, 10, 718-723
5. D. R. Sheelton, J. A. Higgins, J. A. S. Van Kessel, Y. A. Pachepsky, K. Belt, J. S. Karns, *J. Microbiol. Methods*, 2004, 58, 553-231.
6. R. S. Brown and M. Hussain, *Analyst*, 2003, 128, 320-322.
7. A. M. Ibekwe and C. M. Grieve, *J. Appl. Microbiol.*, 2003, 94, 421-431.
8. N. Y. Fortin, A. Mulchandani and W. Chen, *Anal. Biochem.*, 2001, 289, 281-288.
9. V. K. Sharma and E. A. Dean-Nystrom, *Vet. Microbiol.* 2003, 93, 247-260.
10. A. A. Bhagwat, *Int. J. Food Microbiol.*, 2003, 84, 217-224.
11. N. Jothikumar and M. W. Griffiths, *Appl. Environ. Microbiol.*, 2002, 68, 3169-3171.
12. J.-C. Avarre, P. Laujudie and G. Bena, *J. Microbiol. Methods*, 2007, 69, 242-248.
13. M. Minunni, S. Tombelli and M. Mascini, *Anal. Lett.*, 2007, 40, 1360-1370.
14. C. A. Kreader, *Appl. Environ. Microbiol.*, 1996, 62, 1102-1106.
15. I. G. Wilson, *Appl. Environ. Microbiol.*, 1997, 63, 3741-3751.
16. J. Jiang, K. A. Alderisio, A. Singh and L. Xiao, *Appl. Environ. Microbiol.*, 2005, 71, 1135-1141.
17. J. Tuttle, T. Gomez, M. P. Doyle, J. G. Wells, T. Zhao, R. V. Tauxe and P. M. Griffin, *Epidemiol. Infect.*, 1999, 122, 185-192.
18. P. Singleton, *Bacteria in Biology, Biotechnology and Medicine*, 6th edn., Wiley, 2004.
19. J. Huang and Z. Kang, *Microbiol. Res.*, 2010, 165, 411-417.
20. T.-G. Park and Y.-T. Park, *Harmful Algae*, 2010, 9, 59-65.
21. L. A. Castrillo, L. Thomsen, P. Juneja and A. E. Hajek, *Mycol. Res.*, 2007, 111, 324-331.
22. H. Volkmann, T. Schwartz, P. Bischoff, S. Kirchen and U. Obst, *J. Microbiol.* Methods, 2004, 56, 277-286.
23. A. J. Gubala, *J. Microbiol. Methods*, 2006, 65, 278-293.
24. J. Behets, P. Declerck, Y. Delaedt, B. Creemers and F. Ollevier, *J. Microbiol.* Methods, 2007, 68, 137-144.
25. H. Zipper, C. Buta, K. Lammle, H. Brunner, J. Bernhagen and F. Vitzthum, *Nucleic Acids Res.*, 2003, 31, e39.
26. D. H. Gelfand, *PCR technology: principles and applications for DNA amplification*, Stockton Press, 1989.
27. C. R. Jackson, J. P. Harper, D. Willoughby, E. E. Roden and P. F. Churchill, *Appl. Environ. Microbiol.*, 1997, 63, 4993-4995.
28. D. S. Bachoon, E. Otero and R. E. Hodson, *J. Microbiol. Methods*, 2001, 47, 73-82.
29. F. Vitzthum, G. Geiger, H. Bisswanger, H. Brunner and J. Bernhagen, *Anal. Biochem.*, 1999, 276, 59-64.
30. G.-Y. Kim and A. Son, *Anal. Chim. Acta*, 2010, 677, 90-96.
32. X. Zhao, R. Tapec-Dytioco and W. Tan, *J. Am. Chem. Soc.*, 2003, 125, 11474-11475.
33. Y.-J. Liu, D.-J. Yao, H.-Y. Chang, C.-M. Liu and C. Chen, *Biosens. Bioelectron.*, 2008, 24, 558-565.
34. Z.-S. Wu, J.-H. Jiang, L. Fu, G.-L. Shen and R.-Q. Yu, *Anal. Biochem.*, 2006, 353, 22-29.
35. V. K. Sharma, E. A. Dean-Nystrom and T. A. Casey, *Mol. Cell. Probes* 1999, 13, 291-302.
36. C. M. Carey, M. Kostrzynska and S. Thompson, *J. Microbiol. Methods*, 2009, 77, 235-242.
37. C. Chen, W. Wang, J. Ge and X. S. Zhao, *Nucleic Acids Res.*, 2009, 37, 3756-3765.
38. L. E. Morrison and L. M. Stols, *Biochemistry*, 1993, 32, 3095-3104.
39. J. G. Wetmur and N. Davidson, *J. Mol. Biol.*, 1968, 31, 349-370.
40. E. W. Alm, D. Zheng and L. Raskin, *Appl. Environ. Microbiol.*, 2000, 66, 4547-4554.
41. Y.-L. Tsai and B. H. Olson, *Appl. Environ. Microbiol.*, 1992, 58, 2292-2295.
43. J. Bickley, J. K. Short, D. G. McDowell and H. C. Parkes, *Lett. Appl. Microbiol.*, 1996, 22, 153-158.

Example 3

Several studies project the production of CNTs at millions of tons in 2010 and the worldwide market for nanoproducts as $1 trillion by 2015. The escalating pace, scope, and scale at which engineered nanomaterials such as CNTs are being produced and used in numerous aspects of our lives parallel that of asbestos more than a century ago. Just as the newly industrialized world in the 1800s was mesmerized by the versatility of asbestos, the past few decades have witnessed burgeoning interest in the unique properties of engineered nanomaterials. As history has a tendency to repeat itself, it is not surprising that health implications of CNTs have begun to surface. Potential health risks of CNTs have been demonstrated in mice, rats, pigs, and human skin, all of which have experienced consequences of various diseases or cancer. Unfortunately, there are no CNT specific detection and quantification technologies developed for field studies on potential CNT contaminated sites.

The potential adverse effects that CNTs may have on public health and water resources due to indiscriminate use has necessitated an immediate investigation on the fate and transport of CNTs in the environment. However, such investigation cannot be carried out in the absence of a CNT detection tool. The present disclosure relates to a unique quantitative detection method specifically designed to measure CNT contamination in aquatic systems. This technique will play a pivotal role in the pursuit to study the impact and implications of nanomaterials such as CNTs in the environment. The methodology of the present disclosure can be adopted by various agencies to facilitate policy making and production regulation as well as the disposal of nanomaterials including CNTs.

Since its discovery in 1991, CNTs have demonstrated extraordinary mechanical, electrical, thermal and chemical properties and have become candidates for numerous applications such as nanocomposites, energy storage, and microelectronic/medical devices[1-4]. Several studies project the production of CNTs at millions of tons in 2010[5,6] and the worldwide market for nanoproducts as $1 trillion by 2015[7]. Just as asbestos found its way into concrete, pipe insulation, drywall, and fire-retardant coatings long ago, engineered nanomaterials, including CNTs, are beginning to find their way into several commercially available and commonly discarded products, including plastics, papers, textiles, cosmetics, sunscreens, and sporting goods[1-6]. Given the fervor at which CNTs are driven towards mass industrial and commercial applications and the apparent lack of control and regulation in its uses, it is not unreasonable to assume that the CNTs have already begun to find their way into aquatic systems. In these environments they can be present as single-walled carbon nanotubes (SWNTs) or multi-walled carbon nanotubes. SWNTs are one atomic layer thick hollow cylinders of carbon with diameters in the order of a nanometer and lengths ranging from hundreds of nanometers to micrometers[8, 9]. This structure results in a durable product, but at the same time their slender structure makes them hard to remove when ingested or inhaled. The escalating pace, scope, and scale at which CNTs are produced and used in numerous aspects of our lives are very similar to that of asbestos during the Industrial Revolution. It was during that time that asbestos claimed thousands of lives before a ban was finally put in place. The fate of CNTs in aquatic environments has invoked significant concern over its safety and environmental implications. These concerns pertain to its toxicity associated with cardiopulmonary diseases[10, 11], bio-persistence[12], and pathogenicity[12]. Potential health risks of CNTs have been demonstrated in mice[13, 14], rats[15], pigs[16], and human skin[17]. The toxicity resembles asbestos[18] and possibly results in lung disease like mesothelioma (lung cancer), which is caused via inducing oxidative stress[12]. It is therefore critical to detect and quantify the degree of CNT presence and contamination in the aquatic environment before it escalates into an environmental and public health catastrophe.

Despite the suspicion of CNT contamination in the aquatic system, potentially via wastewater runoff or landfill leachate, current detection technologies are inadequate for the verification of CNT contamination. Existing carbon chemistry based tests are not able to differentiate CNTs from other carbon based compounds that are in abundance in the environment. Differentiation via ultra-centrifugation[19], by virtue of the CNTs' inertia mass, is currently used in laboratories to separate CNTs from the solution. However, this method is not specific to CNTs. Any non-CNT suspended particles that have higher inertia mass than the CNTs will also be separated together with the CNTs via centrifugation. Optical methods such as near infrared (NIR) spectroscopy[20] may not yield a specific response from CNTs as its specific wavelength can overlap with that of other organic compounds or nanomaterials. Since CNTs are not soluble in water, they behave as a suspension. This also makes CNT detection using common analytical equipment (e.g., chromatography) nearly impossible.

Introduction

The present disclosure includes a method of quantitative detection of carbon nanotubes (CNTs) in water. The method of the present disclosure involves the "capturing" of CNTs by specific DNAs, which are simultaneously bound to a magnetic fluorescent bead. Magnetic separation is subsequently used to consolidate the captured CNT, and fluorescence measurement is used for quantification. The unique features of the proposed method (e.g., affinity of CNT and DNA, rapid magnetic separation, and improved quantification by using an internal standard) allow the selective detection and quantification of CNTs in the presence of non-specific, carbon-based materials in water. In an embodiment of present disclosure, CNTs in the form of single-walled CNT are used, however, the principle of detection of the present disclosure is also effective for multi-walled CNTs.

Both probe and signaling DNAs are able to co-capture a single CNT during hybridization, and therefore resulting fluorescence measurement exhibits a positive correlation to the CNT concentration. CNT-DNA binding is dominant among all the possible bindings between method components. No significant aggregation of CNTs occurs during quantification. Specificity of the method of the present disclosure is not affected by non-specific binders or environmental factors. In an embodiment of the method of the present disclosure, inline on-chip mixing/hybridization and magnetic trap comprise a portable CNT detection system, and, in another embodiment, the system is integrated in a briefcase platform.

The enabling features of the present disclosure include:

(1) the Specific Detection (Capturing) Method does not Rely on Carbon-Based Chemistry:

Carbon chemistry based methods cannot differentiate CNTs from other carbon structures and compounds. Instead, the specific affinity between CNT and DNA are employed to capture CNTs in water.

(2) Rapid, CNT-Specific Separation Via the Use of Magnetic Field:

Centrifugation or optical spectrometry cannot separate CNTs from non-CNTs, which have the similar (or higher) inertia mass or the potential optical overlaps. The present disclosure uses magnetic field for the rapid and specific separation of magnetic bead tethered CNT from water.

(3) Improved Quantification by Using an Internal Standard:

By employing magnetic fluorescent particles and signaling DNA of different wavelengths, the quantity of CNTs are normalized by the quantity of the CNT-complex that is captured and isolated. This improves quantification by avoiding the inherent error due to the different numbers of magnetic particles captured per each reaction. One signaling DNA (Cy5) serves as the signal of the quantification while the magnetic fluorescent particle serves as an internal standard.

Capturing single CNT by DNA, in the form of single stranded DNA (ssDNA) with the specific sequences, is possible due to π-stacking interaction concerted with van der Waals interaction. The π-stacking interaction refers to the intermolecular force (i.e., passive adsorption) that binds organic molecules with CNTs. These interactions can result in the helical wrapping of CNT by the DNA with a specific sequence. Zheng et al.[40, 41] showed the specific sequences of ssDNA can form a helical structure around CNTs and the corresponding sequences are the alternating Guanine/Thymine (G/T) or Guanine/Cytosine (G/C) in the range of 20 through 90 bp. The binding energy of DNA to CNT is in the same order of magnitude as that between two CNTs for each other[40]. DNA will then be able to compete effectively with the known strong tendency of CNTs to cling to each other.

Figure 15:
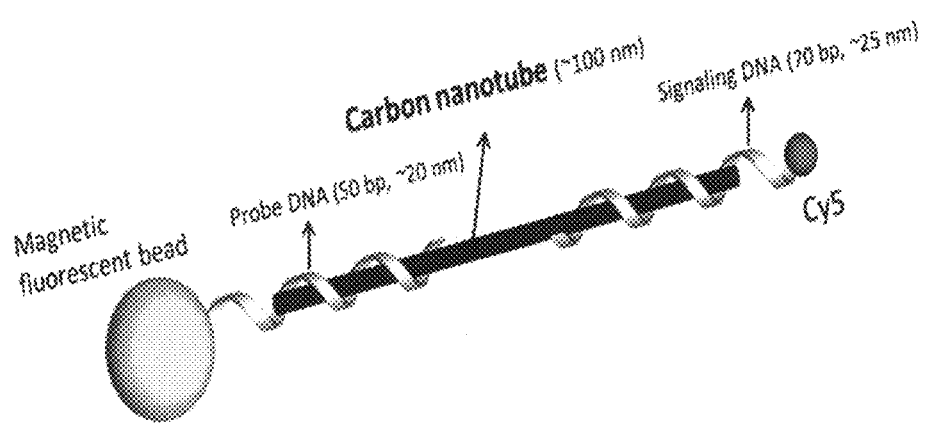
FIG. 15 illustrates an embodiment of the core schematic diagram of the method of detecting, capturing, separating, and/or quantifying carbon nanotubes in water of the present disclosure.

The present disclosure includes: (i) wrapping of CNTs with two G/T alternating DNA, by virtue of its specific affinity; (ii) magnetic separation of CNT-DNA complex from unbounded (incomplete) complexes in solution; and (iii) quantification of CNTs via the fluorescence of the beads and signaling probe (Cy5 and yellow fluorescence from the beads) embedded in the CNT-DNA complex. The schematic of an embodiment of the method of the present disclosure is presented in FIG. 15.

Carbon Nanotube Detection

The present disclosure includes CNT quantification in water. Both probe and signaling DNAs are able to co-capture a range of CNTs during hybridization. The separation and quantification via a magnetic fluorescent bead and signaling DNA enable a positive correlation between the fluorescence intensity and the CNT concentration in water.

Figure 16A:
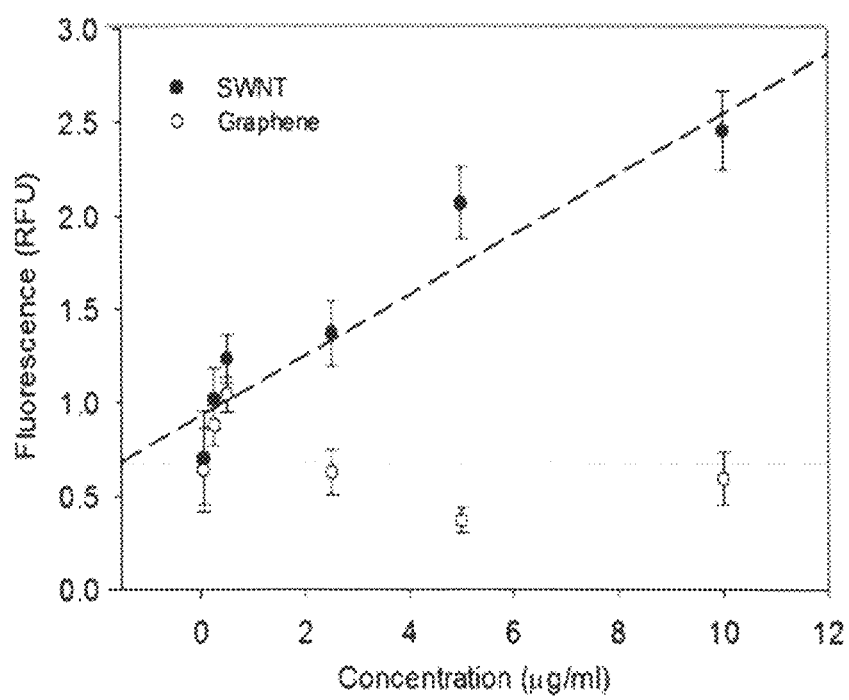
FIG. 16A is a graph that illustrates quantitative detection of CNT (0.05-10 µg/mL) in the configuration of the present disclosure (graphene was used as a negative control)
Figure 16B:
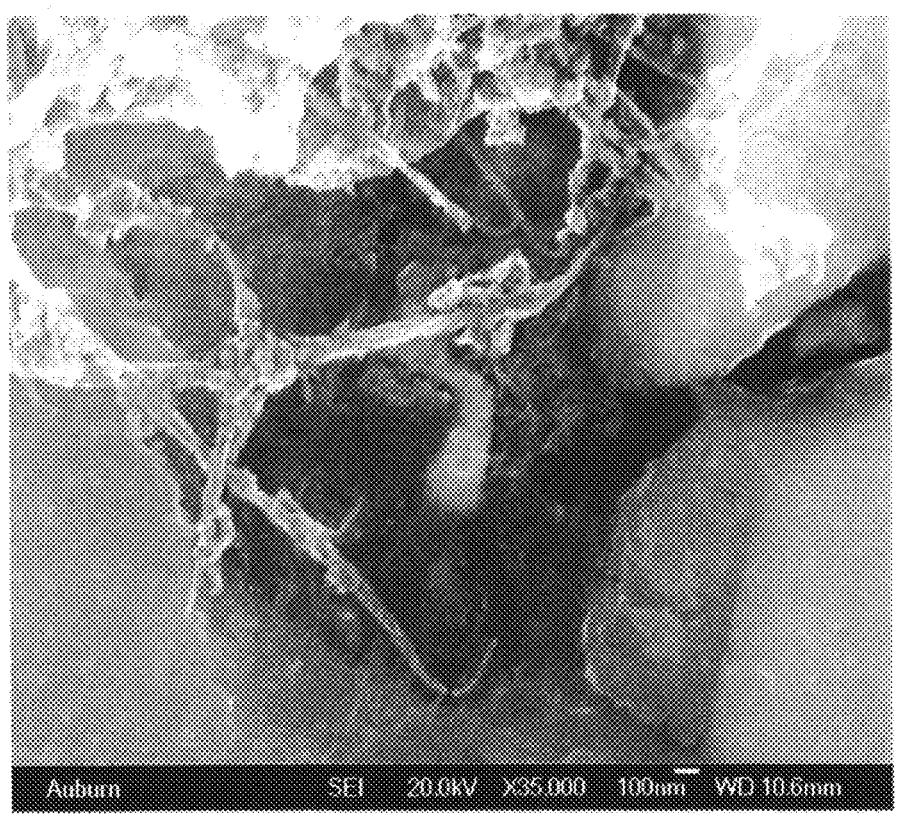
FIGS. 16-B-C are FE-SEM images illustrating the cylindrical structure of CNT (FIG. 16B) and the stacked sheets of graphene (FIG. 16C).
Figure 16C:
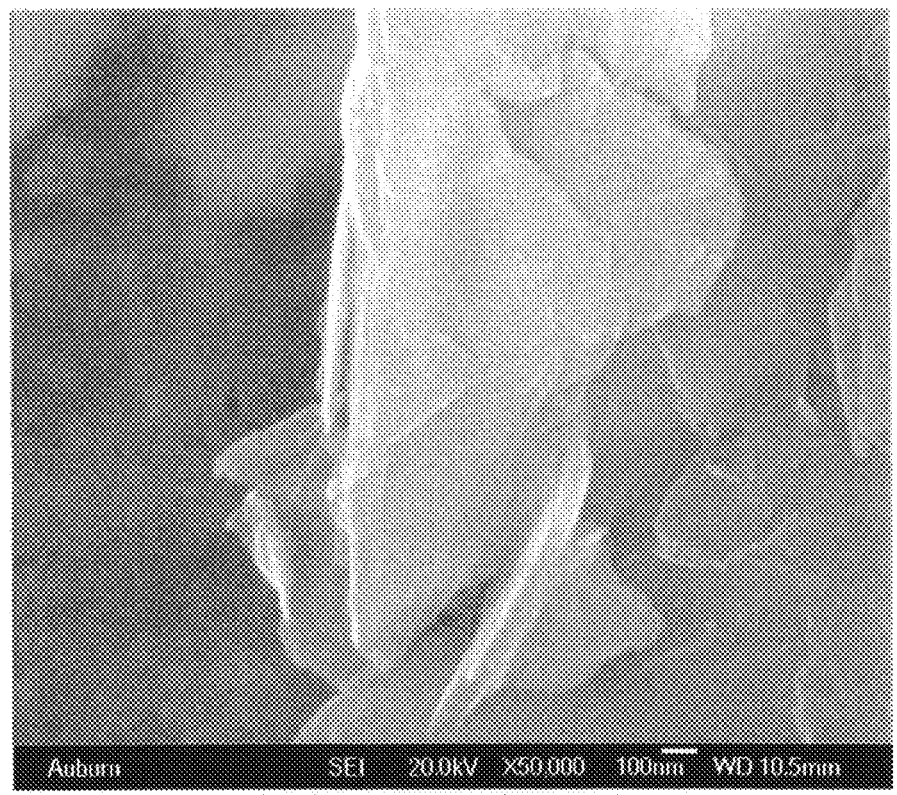

Embodiments of the present disclosure include capturing of single CNT by DNA via their specific affinity. Capturing CNTs has been demonstrated successfully by using the proposed DNA-particle configuration shown in FIG. 15. Both probe and signaling DNA in the form of G/T alternating ssDNA[41] were labeled with a magnetic fluorescent bead and Cy5. As a result, a positive correlation ($R^2$=0.90) was obtained between a varying concentration range of CNTs and the corresponding fluorescence (Cy5/flurorescence yellow) measured from the collected CNTs (FIG. 16A). Note that graphene as a negative control, which has a different structure (planar—see FIG. 16C) but the same carbonaceous composition, has shown negligible signals as compared to CNTs. This result indicates the specificity of the assay in an embodiment of the present disclosure that can enable the selective capturing of the CNTs by wrapping ssDNA around their cylindrical structure (FIG. 16B).

Experimental

Figure 17:
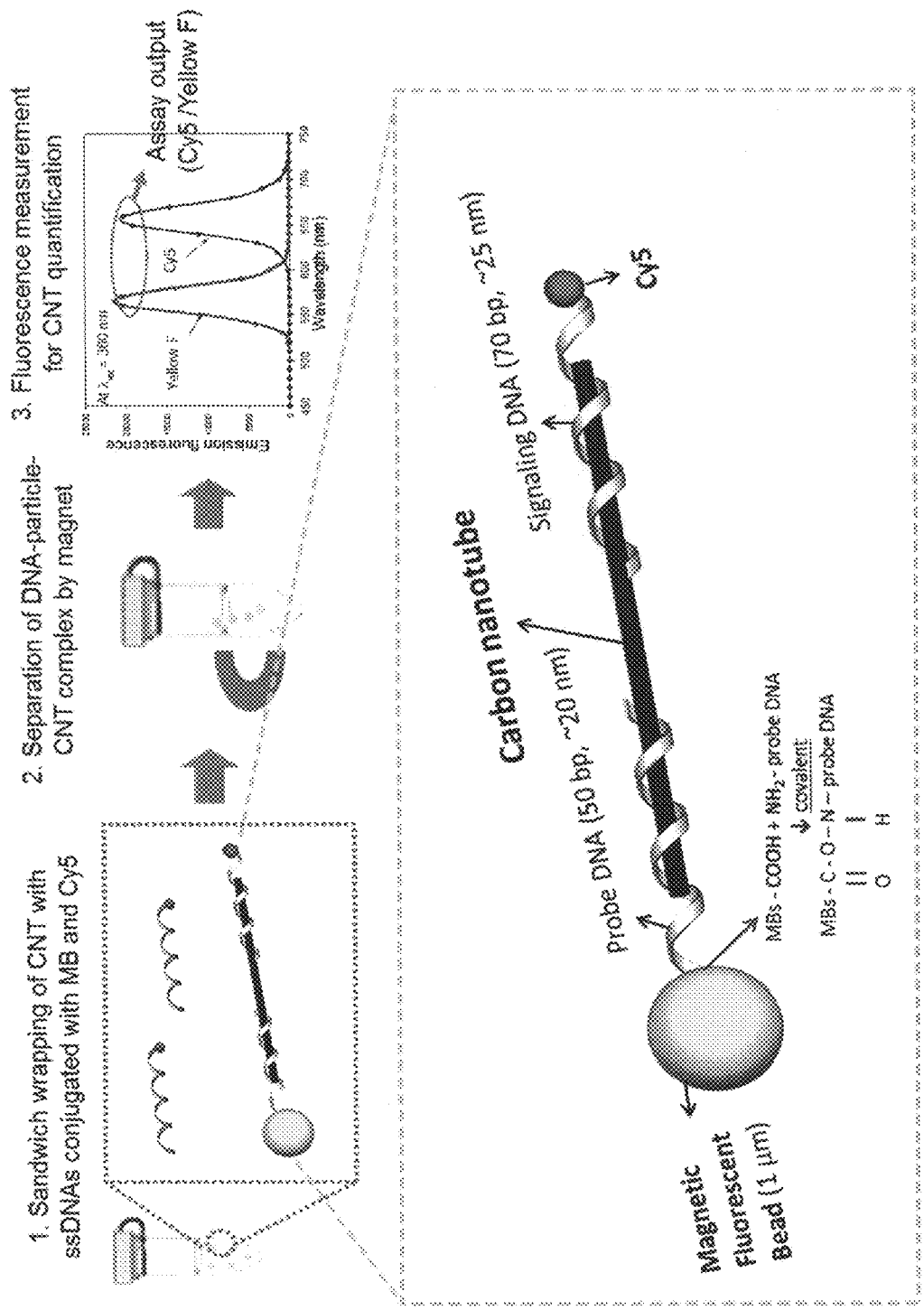
FIG. 17 illustrates a schematic diagram of an embodiment of the CNT detection technology of the present disclosure.

DNA Design and CNT Preparation:

G/T alternating ssDNAs were designed and synthesized for use as probe DNA (40-70 bp) and signaling DNA (40-70 bp, labeled with Cy5) by Integrated DNA Technologies (Coralville, Iowa). The probe DNA was functionalized with amine (—$NH_2$) such that it can be further covalently labeled with the carboxylated magnetic fluorescent particles (Spherotech, Lake Forest, Ill.). The SWNTs (Cheap Tubes Inc, Brattleboro, Vt.) were sonicated by a Misonix ultrasonic cell disruptor (8 W) for 10 minutes in a water batch containing ice to avoid aggregation. Per manufacturer's specifications, the SWNTs have about 0.8-1.6 nm diameters and are about 500-2000 nm in length. Graphenes (Cheap Tubes) as a negative control was also sonicated in the same condition. FIG. 17 shows the schematics of the method and its detailed chemistry.

Conjugation of DNA-Particle Complexes and Hybridization with CNTs:

As illustrated in FIG. 17, the capturing probe DNA is conjugated with the magnetic fluorescent bead, which serves as a carrier and an internal standard, via the formation of an amide bond, with the assistance from both ethylcarbodiimide hydrochloride and N-hydroxysuccinimide. Beads-probe DNA and signaling DNA labeled with Cy5 were added to the reaction buffer, which includes pH buffer (i.e., phosphate buffer, PB) and surfactant (i.e., sodium dodecyl sulfate, SDS). The pH effects were tested using a variety of PB with/without saline water. The hybridization with CNTs was implemented in a hybridization incubator (UVP HB-500 Minidizer, Fisher Scientific), which provided a constant temperature environment with a gentle mixing for the CNTs-DNA hybridization. The incubation time was varied from minutes to hours to identify the optimum time. Elevated temperatures (e.g., about 37, 45, and 60° C.) were used to increase the rapidity of the method.

Figure 18:
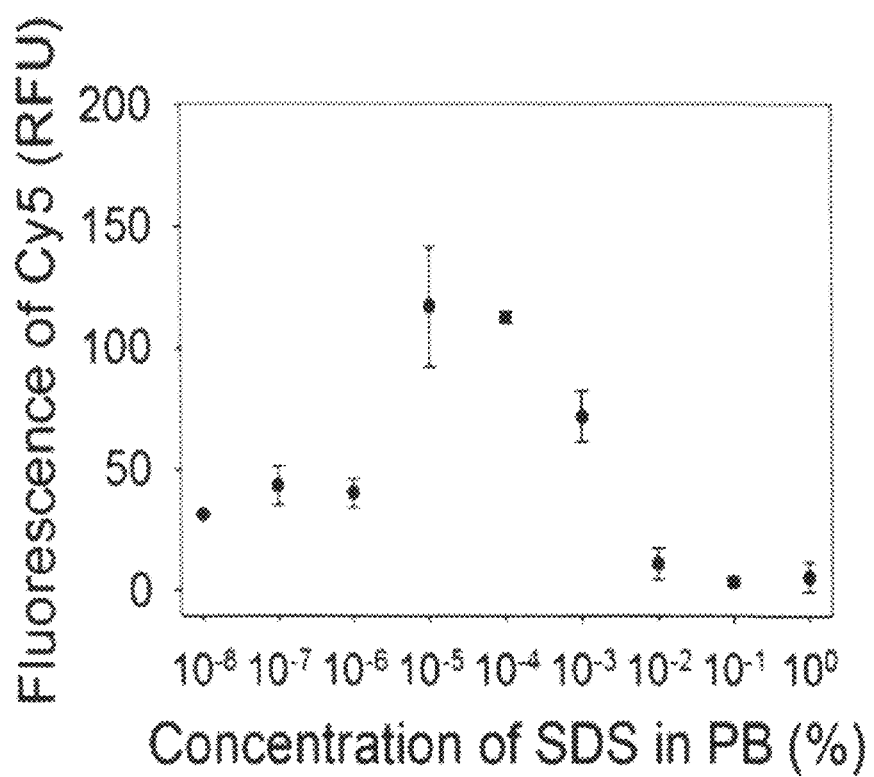
FIG. 18 is a graph that illustrates the optimum amount of SDS that corresponds to maximum fluorescence was about $10^{-5}\%$ (depicted by the arrow) in pH buffer (pH=about 7).

Optimization of Buffer:

The optimization of the amount of SDS was determined. Note that SDS can prevent the aggregation of CNTs[19, 42], but excessive amounts of SDS can saturate the surface of CNT and prevent DNA from binding to it. FIG. 18 shows the optimum amount of SDS for the detection of CNT shown in FIG. 16A. A similar incubation procedure with CNTs and DNA was carried out with varying amounts of SDS (about $10^{-8}$-$10^0$ %). The concentration of CNT was set at about 10 μg/L. The results indicated that the amount of SDS at about $10^{-5}$-$10^{-4}$% was optimum, and it maximized the fluorescence signal. About $10^{-8}$-$10^{-6}$% SDS was too diluted to disperse CNTs in water. About $10^{-2}$-$10^0$% SDS was too concentrated to render sufficient surface spaces for DNA interaction and binding. An optimized quantity of SDS has to be determined to obtain maximum binding of CNTs to DNA while avoiding the aggregation of CNTs. Since there is a possibility that the optimum amount of SDS may vary with different concentrations of CNT, it is important to characterize the range of CNT concentration, of which about $10^{-5}$-$10^4$% SDS is optimum and appropriate. In a similar manner, the interference compounds in the sample will necessitate the re-optimization of SDS.

Washing (Magnetic Separation) and Detection:

CNTs linked with DNA and particles in the 96-well plate (i.e., maximum volume of each well=about 200 μL) were separated using a magnetic field. A MPC-96S magnet (Invitrogen) in the form of 96-well plate was used to extract the DNA-CNTs complex from the solution for washing and separation. The fluorescent detection was performed by a MDS SpectraMax M2 spectrofluorometer. Fluorescent yellow from particles were determined at $\lambda_{ex}$=260 nm and $\lambda_{em}$=478 nm and Cy5 was determined at $\lambda_{ex}$=650 nm and $\lambda_{em}$=670 nm. The output of quantification is expressed by the ratio of the fluorescence between signaling DNA (Cy5) and capturing probe DNA (particles) (i.e., Cy5/fluorescence yellow), as the signal (i.e., Cy5) is normalized by the internal standard (i.e., fluorescent particles) in order to calculate the different numbers of particle complexes in each reaction. This normalization strategy that employs an additional set of fluorescence as an internal standard has been shown to improve quantification resolution[25].

Quantification: Sensitivity, Specificity, Precision, and Rapidity:

Analogous to the previously developed DNA quantification techniques using magnetic and fluorescent particles[25, 27], the plot of the normalized fluorescence versus target CNT concentration was generated. A varying amount of CNTs (ng/L through mg/L) was quantified to determine the sensitivity of the method. Note that the sensitivity on a zeptomolar ($10^{-21}$ mol/L) level for gene quantification in an embodiment of the present disclosure[25] has been shown. The method of the present disclosure conducted at lower concentrations established the limit of quantification. The detection limit is defined as the lowest concentration level that can be determined to be statistically different from a blank (at 99% confidence interval).

Specificity of the assay of the present disclosure was shown in the results based on the parallel experiment with graphene. Graphene in a wider range of quantification was applied.

Other carbonaceous nanomaterial including fullerene was applied to show the specificity of the assay. The specificity in the environmental sample was also elucidated.

Precision (reproducibility) of the assay of the present disclosure was assessed by standard deviation or standard error of multiple experiments, which established the reliability of the technique.

Kinetics of the reaction of the present disclosure were determined by varying the target CNT concentration and temperature. The main reaction in kinetic experiments is the intermolecular binding that occurs between the capturing probe DNA and target CNT. These quantification parameters are relevant to the binding affinity between the method components.

Validation of Quantification:

The absorbance analysis was used to independently validate the CNTs quantification by the method of the present disclosure. Based on the absorbance scan (data not shown), CNT absorbance at UV/visible range overlapped with that of other components (i.e., fluorescent particles). However, unique peaks of CNTs were observed at wavelengths of around about 1,200-1,300 nm (visible-near infrared range)[40, 41, 43]. This allows the use of NIR absorption spectra analysis via a Shimadzu UV-3600 UV-vis-NIR spectrophotometer (185-3,300 nm, equipped at AU) to independently measure the relative abundance of CNTs in aqueous solution so long as the suspension consists of pure CNTs.

Data Analysis

The successful co-capturing of CNT enables the detection and quantification of a pure suspended CNT sample in water. This demonstration involved the execution of a set of default protocols and the presentation of the quantification curve from the regression equation and its correlation coefficient (i.e., fluorescence intensity vs. CNT concentration). The graph was plotted against a range of CNT concentrations. From this graph, the sensitivity of the method of the present disclosure was determined. A table illustrating the detection limit, range of quantification, linearity (i.e., R-square value obtained from regression analysis), standard deviations obtained from replications, and kinetic rate constants and orders is discussed below.

Even though the helical structure formation of G/T alternating DNAs in the form of ssDNA has been demonstrated[41], potential binding may occur between the probe and the signaling DNA. If the binding affinity between two DNAs is higher than that between CNT and DNA, it will result in the formation of DNA dimers. If this occurs, sequences and sizes of the probe DNAs may be varied to minimize dimerization. Based on the study by Zheng et al.[40, 41], other sequences (e.g., GGTT) can also form a helical structure which can wrap around carbon nanotubes. Lower sensitivity can be mitigated by: (1) using larger sample and reagent size, (2) increasing the concentration of reagents such as beads, and/or (3) using higher fluorescence intensity labels such as quantum dots.

Binding Affinity, Aggregation, and Potential Interferences by Environmental Factors CNT-DNA binding is dominant among all the possible binding combinations of CNT, DNA, and beads. Further, no significant aggregation of CNTs occurs during quantification. Moreover, specificity of the method is not affected by non-specific binders or environmental factors.

Figure 19A:
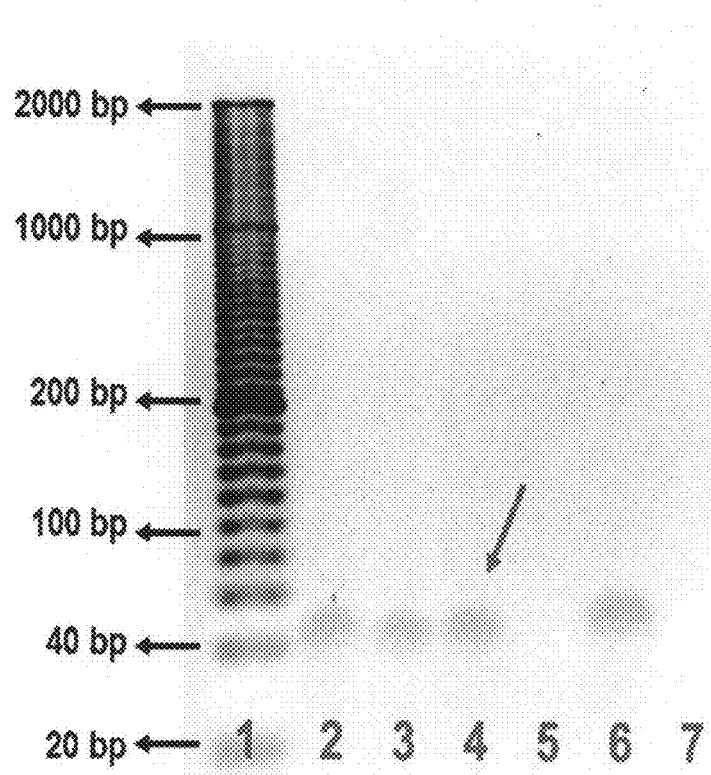
FIG. 19A illustrates investigation of DNA-DNA interaction (potential polymerization) via gel electrophoresis. Lane 1: 20 bp incremented DNA ladder; lane 2: 50 µM probe DNA (40 bp); lane 3: 50 µM signaling DNA (40 bp); lane 4: the mixture of probe DNA and signaling DNA; lane 5: 10 ppm SWNT; lane 6: mixture of probe DNA and SWNT; lane 7: SDS (negative control)
Figure 19B:
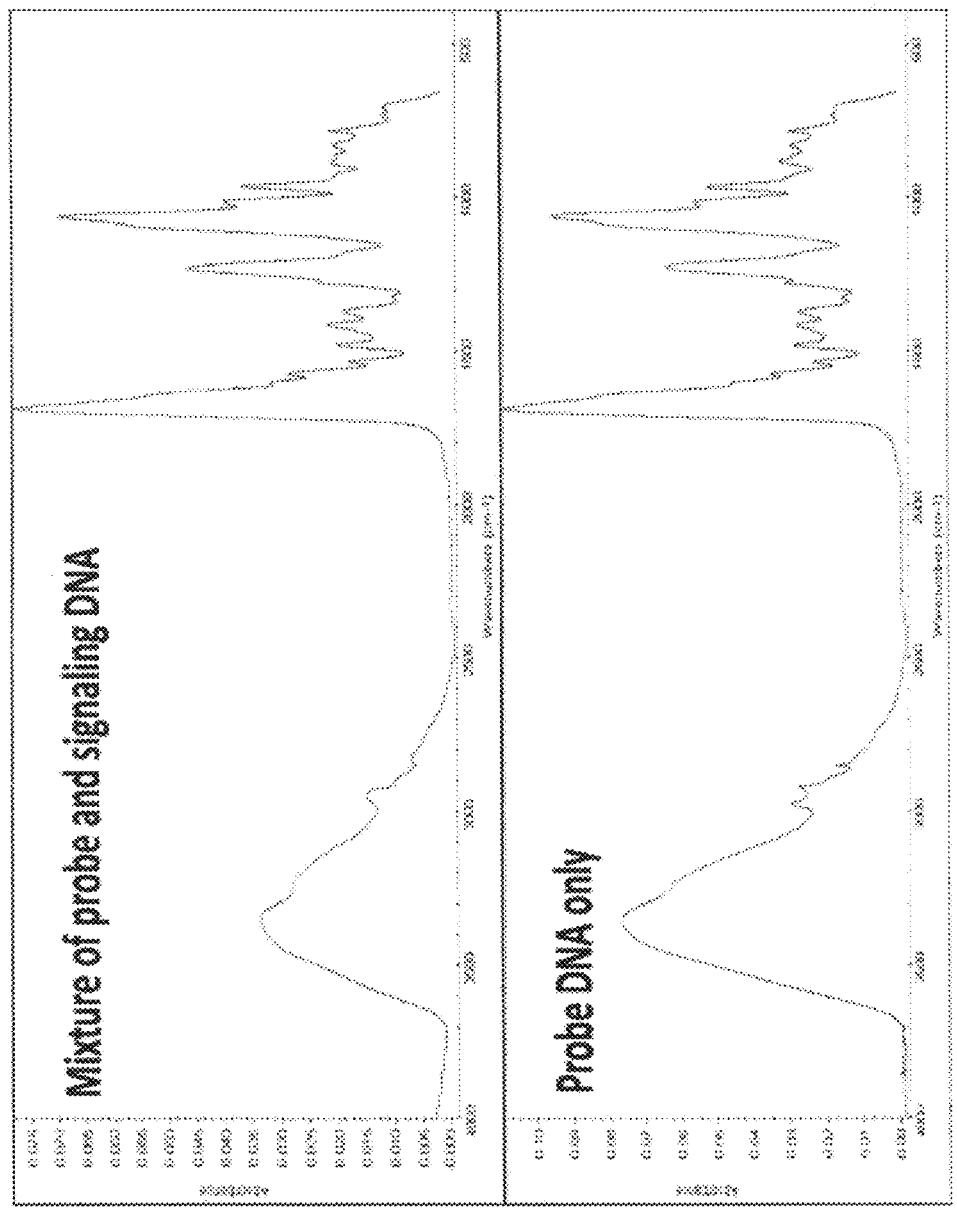
FIG. 19B are graphs that illustrate FT-IR spectra obtained from the incubation of ssDNAs.

Potential interruption to CNT-DNA binding by other interactions between components was investigated by gel electrophoresis as well as FT-IR analysis. After hybridization, the mixture (lane 4, as depicted by the arrow in FIG. 19A) of probe and signaling DNA (each 40 bp) was observed to maintain around 40 bp after hybridization, as compared to the same size of each DNA (lanes 2 and 3). This result indicated that there was no polymerization between DNAs against DNA-CNT interaction (lane 6) throughout the incubation. FT-IR analysis (FIG. 19B) also showed no cross-interaction (polymerization) between DNAs, indicated by the same spectra of probe DNA (or signaling DNA) only and the mixed DNA.

CNT-DNA Binding is Dominant Among all the Possible Binding Combinations Between CNT, DNA, and Beads DNA-DNA interaction: G/T alternating probe and signaling DNAs were used in the method, therefore there is a possibility of forming dimerization or polymerization between the two DNAs during hybridization. The free energy of intermolecular binding (i.e., hydrogen bond between hydrogen atom and oxygen atom) between guanine (G) and cytosine (C) is greater than adenine (A) and thymine (T). Three hydrogen bonds are available for bonding between G and C (i.e., 4.5 kcal/mole×3 bonds=13.5 kcal/mole) as compared to the two hydrogen bonds available between A and T (i.e., 9 kcal/mole). In other words, G/T alternating sequence should not form dimers or polymers because G and T are not the complementary nucleotides. In order to verify that there was no formation of dimers, the DNAs were designed with different sizes (i.e., 50 bp of probe DNA and 70 bp of signaling DNA) for hybridization. Any dimer (120 by or 140 bp) or polymer (170 bp or more) formed after hybridization will be observed in the agarose gel electrophoresis. It was also possible to identify the individual likelihood of both probe and signaling DNA in forming dimers.

Free Energy of Binding:

The binding between CNT and DNA is the key interaction of an embodiment of the method of the present disclosure. In order to quantitatively investigate the affinity among the materials used in the method via its thermodynamics, isothermal titration calorimetry was used. It is a quantitative technique that directly measures the binding affinity constant ($K_a$), enthalpy changes ($\Delta H$), and binding stoichiometry (n) of the interaction between two or more molecules in solution. From these initial measurements, Gibbs energy changes ($\Delta G$) and entropy changes ($\Delta S$) can be determined using the relationship (Eq. 1) in equation of:

$$\Delta G = -RT \ln k = \Delta H - T\Delta S \quad \text{(Eq. 1)}$$

Experimental

DNA-DNA Interaction:

Dimerization or polymerization of probe and signaling DNAs was investigated via gel electrophoresis. It was used to measure the size of DNAs after hybridization. Agarose gel (2%) was used for determining the size of post incubation DNAs. The gel was run at 100 V for 50 min. After ethidium bromide staining, the gel image was acquired via Kodak Gel Logic 100 gel imaging system with a Fisher Carestream health molecular imaging system.

FT-IR Spectroscopy:

The interactions (covalent bonds, π-stacking, polymerization of ssDNAs) among the method components was investigated by a Thermo Fisher Nicolet is 10 ATR-FTIR spectroscopy. To precipitate the DNA, samples were incubated in ethanol and 3 M sodium acetate at −20° C. for three days. Samples were centrifuged at 13,000 rpm for about 10 min and were air-dried before the analysis. The powder of each sample was placed on a single bounce germanium crystal plate iTR/iD5 (Thermo Fisher) with an about 45° incident angle. All samples will be analyzed by running 64 scans at a resolution of 4.

Binding Affinity:

The $K_a$ demonstrates the molecular binding affinity between CNT and DNA as opposed to other combinations (e.g., CNT-beads). The binding affinity, between (1) CNT and probe DNA (and/or signaling DNA); (2) CNTs and beads; and (3) CNTs and CNTs, was determined by Microcal isothermal titration calorimetry. The CNT samples were titrated into the sample cell with the DNAs (i.e., probe and signaling DNA). Any binding process that occurs will result in heat either being generated (exothermic) or absorbed (endothermic). The total energy or power integral used to maintain the constant temperature is equivalent to the amount of thermal energy released or absorbed. The binding curve will be obtained and analyzed with a binding model to obtain the various thermodynamic parameters that pertain to the interaction. The $K_a$ value as an output for CNT-DNA is significantly larger (or at least equivalent) than that for other combinations (e.g., CNT and particles). Thus the binding between CNT and DNA will remain as the key interaction in an embodiment of the method of the present disclosure.

No Significant Aggregation of CNTs Occurs During Quantification

Figure 20:
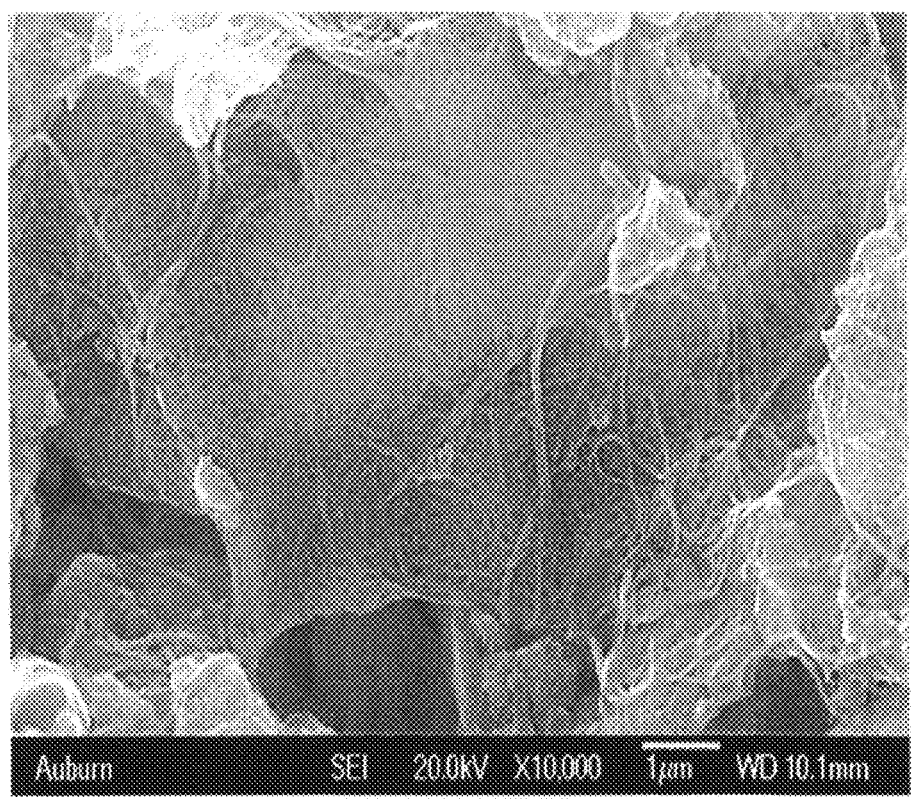
FIG. 20 illustrates a field emission scanning electron microscopic (FE-SEM) image of the highly aggregated CNTs in water.

Aggregation of CNTs will result in erroneous separation and quantification in the method. For example, a single DNA-particle conjugate can be tethered to multiple CNTs instead of a single CNT. Therefore, aggregation of CNTs is kept to a minimum throughout the execution of the protocol, especially during hybridization. Most colloidal suspensions dispersed in an aqueous system will acquire a surface charge either by ionization of surface groups or adsorption of charged species. The significance of zeta potential lies in its relation to the stability of colloidal dispersions. If −30 mV<zeta potential <30 mV, CNTs will aggregate due to charge neutralization. In this case, the size distribution of CNTs based on dynamic light scattering indicates the occurrence of CNTs aggregation. High surface charge implies that CNTs are resistant to aggregation during hybridization. Aggregation of CNTs can be caused by their hydrophobicity[43-45]. FIG. 20 shows the picture of highly aggregated CNTs (SWNTs) in water without the aid of surfactant.

Experimental

Zeta Potential and Size Distribution:

The aggregation of both CNT-CNT (before quantification) and CNT-DNA complex (after quantification) was investigated using a series of experiments to determine the surface charges and size distribution. To observe CNTs aggregation prior to the hybridization, a range of of CNTs (about 0.1-10,000 μg/L) was prepared in water. To observe CNTs aggregation after the hybridization, the same amount of CNTs were incubated with the buffer (optimized in Task I) and DNA with magnetic fluorescent beads. After washing, the complex was transferred into the disposable capillary cells for subsequent zeta potential and size measurement. The electrophoretic mobility (p) of samples was measured in a 1 mM NaCl solution using a ZetaPALS analyzer (Brookhaven, equipped at USC). The subsequent zeta potential was calculated from the measured electrophoretic mobility using the Smoluchowski approximation[43]. The size distribution was obtained by measuring the hydrodynamic radii of CNTs complex via dynamic light scattering.

High Resolution Transmission Electron Microscopy (TEM):

It is one of the most common imaging techniques for nanoscale materials. TEM was used to verify CNT aggregation as it is the most common imaging techniques for characterizing nanoscale materials. A high resolution TEM (JEM 2100F, JEOL, Japan, equipped at USC) fitted with Schottky field emission gun and Fischione HA-DA detector was used to investigate the aggregation of CNTs during hybridization. The samples obtained from the hybridization were dispersed in deionized water and a drop of the suspension was placed directly on a nickel TEM grid coated with Formvar.

Raman Spectroscopy:

Raman spectroscopy is also commonly used for CNT characterization[41]. It has been used to study the colloidal stability of CNTs at various water chemistry conditions such as pH, ions, and dissolved organic carbons (DOC)[46]. The radial breathing mode of CNTs in the form of SWNT (appearing between 120 and 250 $cm^{-1}$ Raman shift) was used for determining CNT diameters. Its frequency is inversely proportional to the CNT diameter with which the aggregation of CNTs can be made known. The Raman spectra were recorded using LabRam Raman spectrometer equipped with a confocal microscope at USC. The samples (same as described in zeta potential and size distribution) were prepared by the filtration (0.2 μm membrane) and dried in a desiccator overnight. Note that Raman spectroscopy was also used to further evaluate ultrasonication (described below) which was used to disperse CNTs in solution.

Specificity of the Method is not Affected by Non-Specific Binders or Environmental Factors The effects and magnitude of interference by carbon based, non-specific binders and environmental factors on the method were investigated. This shed light on potential reduction of the default protocol's performance if field samples are to be used instead of pure CNTs in water sample. The interference by non-CNT, carbon based materials (or contaminants) that are abundant in the environment was evaluated. Their presence in the test sample can induce non-specific binding to the probe and signaling DNA, and result in reduced specificity for CNT quantification. The interference pertaining to environmental factors (e.g., pH, ions, DOC, and turbidity) was also studied.

Figure 21:
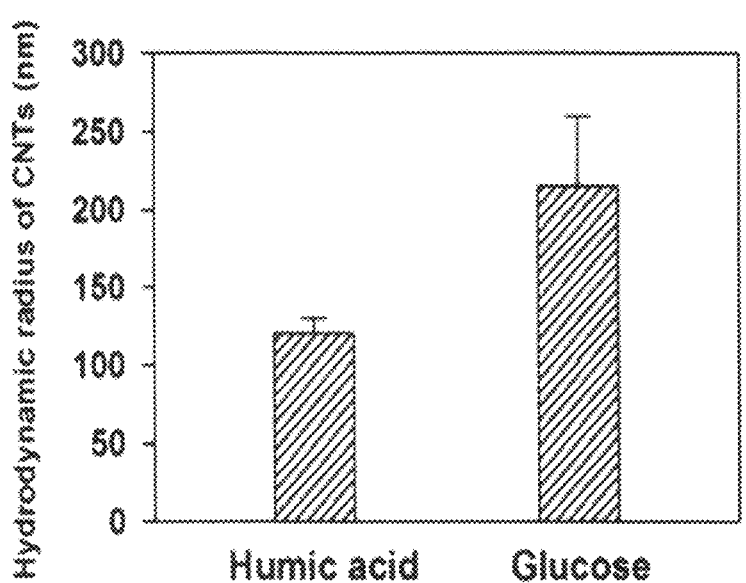
FIG. 21 is a graph that illustrates the effects of organic matters on the CNT aggregation.

The study (FIG. 21) has shown CNT aggregation based on the measurement of the hydrodynamic radii of CNTs (obtained via dynamic light scattering) in the presence of two types of organic matter. FIG. 21 shows CNT aggregation in the presence of humic acid and glucose. Interestingly, more aggregation of CNTs occurred in the presence of glucose, which is more hydrophilic than humic acids. The hydrophobicity of DOC may be related to the degree of CNT aggregation. This finding is particularly important because it shows the environmental factors may affect CNT quantification.

Specificity in the Presence of Carbon Based Materials:

Non-specific binding by other non-CNT organic contaminants can be an issue. Thus, specificity was examined using a series of carbon based controls such as graphene, graphite, and fullerene that possess structural differences from CNT. The method's ability to discriminate between these structural differences demonstrates its specificity. Table 1 lists the non-specific binders to be tested. Each of the non-specific binder in Table 1 was be quantified using the method protocol previously established. Pure CNTs were used as the control. The fluorescence obtained from the experiment using each of the non-specific binder was compared to that for pure CNT control. In other words, the calibration curves for each non-specific binder was compared to that for CNTs.

TABLE 1

The list of non-specific binders
to be tested in Task II.

| Names | Characteristics | Abundance in nature |
|---|---|---|
| Graphene | Same carbon materials with the structural difference (planar, single) | Not yet, but potentially yes |
| Graphite | Same carbon materials with the structural difference (planar, multiple) | Possible |
| Fullerene | Same carbon materials with the structural difference (spherical) | Not yet, but potentially yes |
| Soot | Similar carbon materials with aggregated and non-pure nature | Yes |

A range of non-specific binders (about 0.1-10,000 μg/L) were added to CNT samples (about 0.1-10,000 μg/L) to simulate the actual water sample that contains non-specific binders. CNT samples with and without non-specific binders were quantified using the method protocol and their difference in the fluorescence measurements were observed. From both experiments above, it was expected that there would be no (or minimal) significant difference between the fluorescence measurements of the control versus test samples laden with non-specific binders.

Effects of Environmental Factors:

In addition to carbon based non-specific binders, a number of environmental factors can also affect the efficacy of the method by promoting CNT aggregation or lowering the specificity of assay. For example, the presence and variation of environmental factors such as pH, ions, DOC, and turbidity, may exacerbate the aggregation of CNTs. Furthermore, CNTs in aquatic environments can undergo chemical and physical transformations and encounter a multitude of solution conditions that can cause aggregation. The environmental factors include solution pH, dissolved background ions, DOC (including natural organic matter), and turbidity. In order to elucidate the effects of the environmental factors on CNTs aggregation and assay specificity, the following experiments were performed using (1) field collected water samples and (2) laboratory prepared water samples.

Field Collected Water Sample.

A total of 42 (triplicate) water samples were collected from a total of 14 points (two sampling points for seven locations) considering diverse environmental characteristics. Water sample were collected from (1) a surface water source (Lake Murray, S.C.); (2) local domestic wastewater plants (Columbia, S.C.). After basic measurements (e.g., pH, ions, conductivity, DOC, turbidity) and screening, representative field water samples were selected for each environmental factor tested. Anions concentrations were measured by an ion chromatography instrument, while cation concentrations were determined using inductively coupled plasma emission spectroscopy. DOC was determined by a DOC analyzer (Shimadzu, at USC). Turbidity was determined by a turbidity meter.

Laboratory Prepared Water Sample.

The environmental factors used to prepare the laboratory sample are listed in Table 2. Various sample compositions of ions (e.g., conductivity of 300-1,200 μS/cm), pH (acidic, neutral, and basic), DOC (1-20 mg/L), and turbidity (1-20 NTU) were spiked into pure deionized water. DOC was prepared for hydrophobic (e.g., humic acids) and hydrophilic (e.g., glucose) hydrocarbons. The humic acids were prepared as Suwannee River reverse osmosis isolate obtained from International Humic Substance Society. A varying amount of CNT (about 0.1-10,000 μg/L) was spiked into the water sample intended for CNT quantification experiment. Based on the protocol developed, CNT quantification was carried out using the water samples prepared as described above.

TABLE 2

The list of environmental factors to be tested in the Task III.

| Parameter | Types or range | Potential adverse effect on CNT detection |
|---|---|---|
| pH | basic, neutral, acidic | Yes at low pH |
| Background ions | NaCl, $Na_2SO_4$, $CaCl_2$ | Yes with divalent cations |
| Conductivity | 300-1200 (μS/cm) | Yes at high conductivity |
| DOC | hydrophobic, hydrophilic, | Yes with hydrophilic organic matter |
| Turbidity | 1-20 NTU | Potentially yes |

Data Analysis

Thorough characterization allowed understanding of the enabling mechanisms behind the method of the present disclosure. CNT-DNA binding is thus dominant and specific and CNT aggregation is minimized. The effect of interfering carbon based non-specific binders on the performance of the method is minimal. Statistical analysis was used to determine the significance of any differences observed between results from using pure CNTs and interference laden samples. The presence of environmental factors such as ions and DOC does not result in significant errors by nonspecific binding with CNTs. In an embodiment of the present disclosure, a low level of CNT in a turbid and heterogeneous water is detected.

Development of System Components & Integration into a Microfluidic Environment

Disclosed is an embodiment of the In-situ carbon Nanotube Detection System (INDS) as a portable platform implementation of the present disclosure. Embodiments of the present disclosure include miniaturized fluidic systems to achieve mixing and hybridization, an inline magnetic trap to enable magnetic separation, and the integration of system components including electrical specification into a briefcase platform.

Experimental

Inline on-Chip Mixing and Hybridization

Figure 23A:
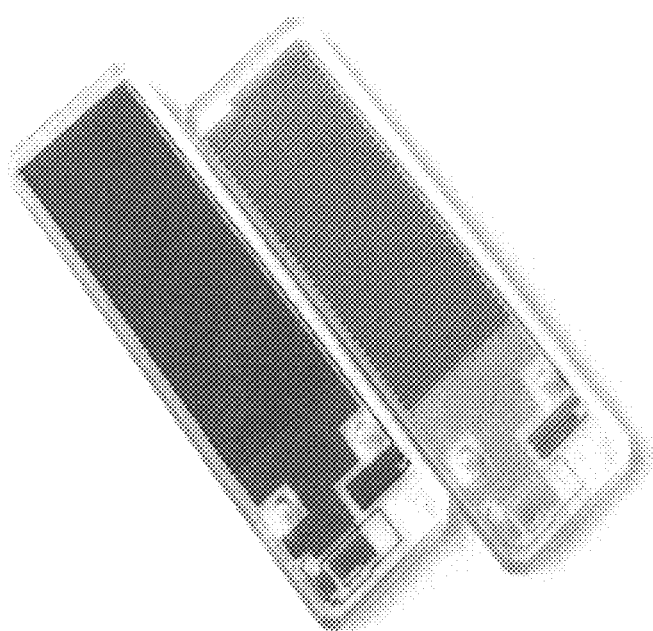
FIG. 23A illustrates dolomite microreactor chips for use in an embodiment of the present disclosure.
Figure 23B:
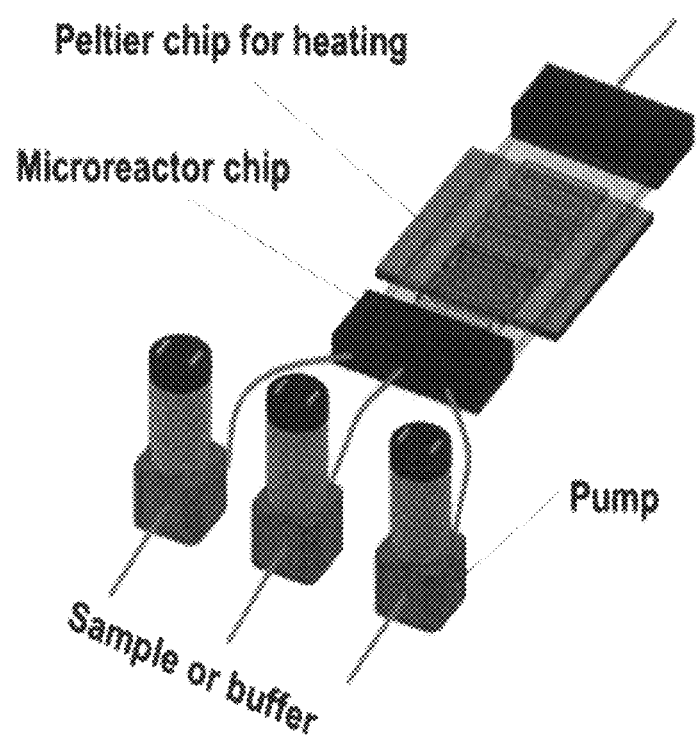
FIG. 23B illustrates a schematic of a hybridization module of an embodiment of the present disclosure.

The use of static mixing for achieving on-chip mixing and hybridization was investigated. For this purpose, the implementation of the mixing/hybridization step was performed with commercially available microfluidic based microreactor chip. A fine balance between flow rates, concentrations of reagents, residence time, temperature, and magnetic bead size is necessary in order to achieve rapid mixing and hybridization. The characterization of static mixing and hybridization was carried out using Dolomite 250 μL Microreactor Chip (P/N 3000281) as shown in FIG. 23A (www.dolomite-microfluidics.com). FIG. 23B shows the hybridization module that was implemented on the briefcase platform.

Incubation Using Microfluidic Mixer Chip:

Mixing and hybridization parameters investigated included flow rates, residence times (number of flow-through), temperature, reagents concentrations, and magnetic bead sizes. CNT samples in the water were injected and incubated with particle-DNA complex in the 250 μL Dolomite microreactor chip using Dolomite Mitos miniature peristaltic pump (P/N 3200054) at various flow rates (about 0.2-0.5 mL/min). Reaction temperature was varied (about 15-45° C.) by heating the microreactor chip via a bench hot plate tandem with Dolomite hot plate adaptor (P/N 3000207) or thermoelectric Peltier Chip (TEC1-12705). Surface temperature of the microreactor chip was monitored using Kintrex IRT0421 Non-Contact Infrared Thermometer. After hybridization, the CNT-particle hybrids ejected from the microreactor chip were subsequently separated by the magnet (MPC®-965 or MPC®-9600, Invitrogen) and washed with phosphate buffer (pH=about 7.5). The fluorescence measurement was implemented by a MDS Spectramax M2 spectrofluorometer.

The hybridization results from employing the microreactor chip were compared against the standard laboratory method of using an incubator. Fluorescence intensities from both methods were comparable.

Inline Magnetic Trap

Figure 24:
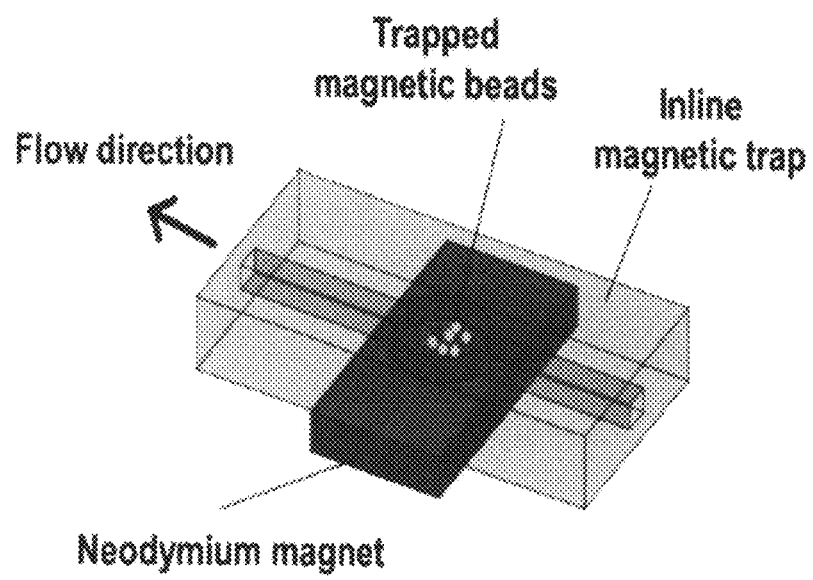
FIG. 24 illustrates a schematic of an inline magnetic trap of an embodiment of the present disclosure.

An inline magnetic trap to separate the particle/CNT hybrids from solution was developed. FIG. 24 shows the schematic of the inline magnetic trap. The neodymium magnet pulls the magnetic beads and hybridized CNT out of the flow stream as the hybridized product is being injected into the trap. The input to the inline magnetic trap is the output from the microreactor chip characterized above. The inline magnetic trap is the briefcase platform equivalent of the magnetic separation step using the external magnet. With the inline magnetic trap, we also performed the rinsing procedure by flushing the magnetic trap with a washing buffer. The similar concept was shown to be successful to separate magnetic beads in microfluidic platform[50]. Various parameters were tested to investigate the trapping efficiency of the inline magnetic trap.

Inline Magnetic Trap Fabrication:

The inline magnetic trap comprised a channel layer sandwiched between two cover layers. The channel layer was made of NSF 51 silicone rubber (about 1.5 mm thickness). The channel and trap geometry used were about 3 mm wide and 30 mm long channel. The cover layers comprised glass sheets (about 1.5 mm thickness). The silicone rubber channel layer also served as a gasket when the layers were mechanically sandwiched together. Barbed tubing connectors for about 1.5 mm ID tubing were attached to one of the cover layers. The neodymium magnet used was N48 disc 25 mm diameter and 3 mm thick.

Flow Rate, Trap Geometry, and Rinsing:

The flow rate should be sufficiently slow for the magnetic beads to be pulled out from the flow stream. In addition, the drag forces on the magnetic beads should not cause the trapped magnetic beads to re-entrain back into the flow stream. Using the flow rates established above, Spherotech magnetic fluorescent beads (D=1 μm) suspension were injected into the inline magnetic trap. After the beads were trapped, additional washing buffer was injected into the channel for additional about 1, 5, and 10 minutes. The rinsing cycle will require the flow to stop and the particle/CNTs to shuffle between the trap surfaces before resuming the flow. This allows unbound particles to be freed from the cluster and to be carried away once the flow resumes. Shuffling was achieved by stopping the flow and moving the neodymium magnet to the surface of opposite cover layer. Each shuffling is equivalent to one rinsing cycle. The experiment was repeated for 1, 5, and 10 rinsing cycles before collecting the trapped particles/CNT.

Results

The trapping efficiency was equivalent using laboratory based method via the Invitrogen magnet. The plot between flow rates and trapping efficiency for a given washing buffer rinse showed that the trapping efficiency decreases with increasing flow rates. In addition, with increasing washing buffer flow times, the contribution to the fluorescence intensity from unbound nanoparticles will decrease. With the increasing rinsing cycles, the contribution to fluorescence intensity from unbound nanoparticles decreased significantly. The rinsing cycle was compared to existing laboratory methods of rinsing it with washing buffer three times.

System Integration on a Briefcase Platform

Figure 22:
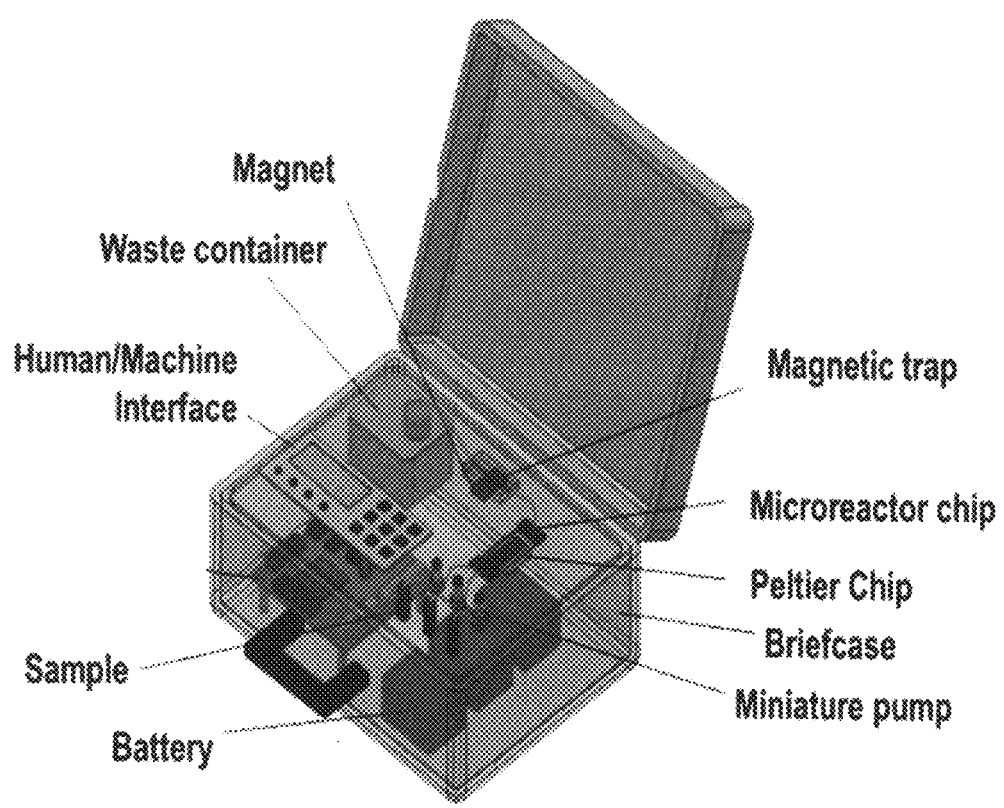
FIG. 22 illustrates an embodiment of an in-situ carbon nanotube detection system (INDS) in a briefcase platform of the present disclosure.

In an embodiment of the present disclosure, the microreactor chip is connected with the magnetic trap on a briefcase platform as shown in FIG. 22. The bench-top or portable spectrofluorometer was used to measure the fluorescence of the CNT/particles trapped by the inline magnetic trap.

Specification of Electronic Components

The electronic controller used was Trilogi T100MD888+ PLC with Trilogi MD HMI (Triangle Research Inc., Blaine, Wash.). Both units are powered by 24 VDC supply. The peristaltic pumps will be powered via the analog output in order to control the pump voltage and therefore its flow rate.

Specification for Portable Spectrofluorometer

In an embodiment of the present disclosure, a portable spectrofluorometer (380-1050 nm wave length) for use in the method is manufactured by Ocean Optics (Dunedin, Fla.). The same company carries the illumination source for this unit.

Integration and CNT Detection (1) Reagent injection: The reagents injected into the chip include particle-probe DNA complex, target CNTs, signaling DNA, and hybridization buffer. Based on the results from previous study[27], the particle-probe DNA complex was prepared in advance and stored until the hybridization for a maximum of 30 days. (2) Injection, mixing and hybridization: Injection flow rate into the chip was at the value determined above. Injection only begins after the heating source is able to heat the microreactor chip to the required temperature, if necessary. (3) Post hybridization trapping and rinsing: The output from the chip was injected into the inline magnetic trap. The extended buffer wash and number of rinsing cycles was based on results discussed above. Additional buffer was injected into the line via one or all the reagent/sample inlets. This will ensure that all particle complexes are flushed from the chip into the magnetic trap. (4) Fluorescence detection: The bounded CNT-beads that are held on by the neodymium magnet in the inline magnetic trap were flushed out (after magnet removal) and underwent fluorescence measurement. The target CNT quantification was compared to the control (i.e., non-microfluidic experiment) results using the developed protocol.

Complete transfer of CNT-hybrid from injection, via incubation and separation, to fluorescence detection is important to minimize errors resulting from trapped beads along the fluidic lines. This can be minimized by ensuring the internal diameter of the fluidic lines changes gradually. If there is no existing portable spectrofluorometer suitable to perform fluorescence detection due to its detection limit, the integrated briefcase platform can be used with existing bench top spectrofluorometer. Lower sensitivity can also be mitigated by: (1) using larger sample and reagent size, (2) increasing the concentration of beads, and/or (3) using higher fluorescence intensity labels such as quantum dots.

Applications

The potential adverse effects that CNTs may have on public health, and water resources as a result of indiscriminate use necessitates an immediate investigation of the fate and transport of CNTs in potentially influenced environments[2, 3, 6, 7, 51]. However, such an investigation cannot be carried out in the absence of proper detection tools for CNTs in water. Embodiments of the present disclosure will result in the availability of a technique for the quantitative detection of CNTs in a water sample that is laden with other carbon based non-specific compounds. This technique will play a pivotal role in the pursuit to study the impact and implications of nanomaterials such as CNTs in the environment.

REFERENCES

Which are Herein Incorporated by Reference

1. Baughman, R. H.; Zakhidov, A. A.; de Heer, W. A., Carbon nanotubes—the route toward applications. Science 2002, 297, (5582), 787-792.
2. Harutyunyan, A. R.; Pradhan, B. K.; Surnanasekera, G. U.; Korobko, E. Y.; Kuznetsov, A. A., Carbon nanotubes for medical applications. European cells and materials 2002, 3, 84-87.
3. Valcarcel, M.; Simonet, B. M.; Cardenas, S.; Suarez, B., Present and future applications of carbon nanotubes to analytical science. Analytical and Bioanalytical Chemistry 2005, 382, (8), 1783-1790.
4. O'Connell, M. J., Carbon nanotubes: properties and applications. CRC Press: Boca Raton, Fla., 2006.
5. Ball, P., Roll up for the revolution. Nature 2001, 414, 142-144.
6. Taubes, An interview with Dr. Richard Smalley; ESI special topic of Nanotechnolgy. Nanotechnology 2001.
7. Roco, M. C., Environmentally responsible development of nanotechnology. Environmental Science and Technology 2005, 39, (5), 106A-112A.
8. Iijima, S.; Ichihashi, T., Single-shell carbon nanotubes of 1-nm diameter. Nature 1993, 363, (6430), 603-605.
9. Hersam, M. C., Progress towards monodisperse single-walled carbon nanotubes. Nat Nano 2008, 3, (7), 387-394.
10. Pope, C. A. r.; Burnett, R. T.; Thurston, G. D.; Thun, M. J.; Calle, E. E.; Krewski, D.; Godleski, J. J., Cardiovascular mortality and long-term exposure to particulate air pollution: epidemiological evidence of general pathophysiological pathways of disease. Circulation 2004, 109, 71-77.
11. Lam, C. W.; James, J. T.; McCluskey, R.; Arepalli, S.; Hunter, R. L., A review of carbon nanotube toxicity and assessment of potential occupational and environmental health risks. Critical Reviews in Toxicology 2006, 36, (3), 189-217.
12. Pacurari, M.; Yin, X. J.; Zhao, J.; Ding, M.; Leonard, S. S.; Schwegler-Berry, D.; Ducatman, B. S.; Sbarra, D.; Hoover, M. D.; Castranova, V.; Vallyathan, V., Raw sigle-wall carbon nanotubes induce oxidative stress and activate MAPKs, AP-1, NF-kB, and Akt in normal and malignant human mesothelial cells. Environmental health perspectives 2008, 116, 1211-1217.
13. Lam, C. W.; James, J. T.; McCluskey, R.; Hunter, R. L., Pulmonary toxicity of single-wall carbon nanotubes in mice 7 and 90 days after intratracheal instillation. Toxicological Sciences 2004, 77, 126-134.
14. Shvedova, A. A.; Kisin, E. R.; Mercer, R.; Murray, A. R.; Johnson, V. J.; Potapovich, A. I.; Tyurina, Y. Y.; Gorelik, O.; Arepalli, S.; Schwegler-Berry, D.; Hubbs, A. F.; Antonini, J.; Evans, D. E.; Ku, B. K.; Ramsey, D.; Maynard, A.; Kagan, V. E.; Castranova, V.; Baron, P., Unusual inflammatory and fibrogenic pulmonary responses to single walled carbon nanotubes in mice. American Journal of Physiology—Lung Celluar and Molecular Physiology 2005, 289, L696-L697.
15. Warheit, D. B.; Laurence, B. R.; Reed, K. L.; Roach, D. H.; Reynolds, G. A. M.; Webb, T. R., Comparative pulmonary toxicity assessment of single-wall carbon nanotubes in rats. Toxicological Sciences 2004, 77, 117-125.
16. Huczko, A.; Lange, H.; Catko, E.; Grubek-Jaworska, H.; Droszcz, P., Physiological test of carbon nanotubes: Are they asbestos-like? Fullerenes Nanotubes Carbon Nanostruct 2001, 9, 251-254.
17. Shvedova, A. A.; Castranova, V.; Kisin, E. R.; Schwegler-Berry, D.; Murray, A. R.; Gandelsman, V. Z.; Maynard, A.; P., B., Exposure to carbon nanotube material: Assessment of nanotube cytotoxicity using human keratinocyte cells. Journal of Toxicology and Environmental Health. Part A 2003, 66, 1909-1926.
18. Poland, C. A.; Duffin, R.; Kinloch, I.; Maynard, A.; Wallace, W. A. H.; Seaton, A.; Stone, V.; Brown, S.; MacNee, W.; Donaldson, K., Carbon nanotubes introduced into the abdominal cavity of mice show asbestos-like pathogenicity in a pilot study. Nature Nanotechnology 2008, 3, (7), 423-428.
19. O'Connell, M. J.; Bachilo, S. M.; Huffman, C. B.; Moore, V. C.; Strano, M. S.; Haroz, E. H.; Rialon, K. L.; Boul, P. J.; Noon, W. H.; Kittrell, C.; Ma, J.; Hauge, R. H.; Weisman, R. B.; Smalley, R. E., Band gap fluorescence from individual single-walled carbon nanotubes. Science 2002, 297, (5581), 593-596.
20. cherukuri, P.; Bachilo, S. M.; Litovsky, S. H.; Weisman, R. B., Near-Infrared fluorescence microscopy of single-walled carbon nanotubes in phagocytic cells. Journal of American Chemical Society 2004, 126, 15638-15639.
21. Son, A.; Dosev, D.; Nichkova, M.; Ma, Z.; Kennedy, I. M.; Scow, K. M.; Hristova, K. R., Quantitative DNA hybridization in solution using magnetic/luminescent core-shell nanoparticles. Analytical Biochemistry 2007, 370, 186-194.
22. Son, A.; Dhirapong, A.; Dosev, D.; Kennedy, I. M.; Weiss, R. H.; Hristova, K., Rapid and quantitative DNA analysis of genetic mutations for polycystic kidney disease (PKD) using magnetic/luminescent nanoparticles. Analytical and Bioanalytical Chemistry 2008, 390, (7), 1829-1835.
23. Son, A.; Nichkova, M.; Dosev, D.; Kennedy, I. M.; Hristova, K. R., Luminescent lanthanide nanoparticles as labels in DNA microarrays for quantification of MTBE-degrading bacteria. Journal of Nanoscience and Nanotechnology 2008, 8, (5), 2463-2467.
24. Son, A.; Kennedy, I. M.; Scow, K. M.; Hristova, K., Quantitative gene monitoring of microbial tetracycline resistance using magnetic luminescent nanoparticles. Journal of Environmental Monitoring 2010, 12, 1362-1367.
25. Kim, G. Y.; Son, A., Development and characterization of a magnetic bead-quantum dot nanoparticles based assay capable of *Escherichia coli* O157:H7 quantification. Analytica Chimica Acta 2010, 677, 90-96.
26. Kim, G. Y.; Son, A., Quantitative detection of *E. coli* O157:H7 eaeA gene using quantum dots and magnetic particles. Biotechnology and Bioprocess Engineering 2010, 15, (6), 1084-1093.
27. Kim, G. Y.; Wang, X.; Son, A., Inhibitor resistance and in-situ capability of nanoparticle based gene quantification. Journal of Environmental Monitoring 2011, 13, 1344-1350.
28. Kim, G. Y.; Wang, X.; Ahn, H.; Son, A., Gene quantification by NanoGene assay is resistant to humic acids. Environmental Science and Technology 2011, 45, 8873-8880.
29. Kilpatrick, K.; Chua, B.; Son, A., In-situ capable method for detecting pathogenic bacteria in water. 2012, In preparation.
30. Lee, J.-T.; Son, A.; Dosev, D.; Kennedy, I. M.; Hristoval, K. R., DNA quantification by magnetic luminescent nanoparticles in a microchannel system. 2012, In preparation 31. Yoon, J.; Yoon, Y.; Amy, G.; Cho, J.; Foss, D.; Kim, T. H., Use of surfactant modified ultrafiltration for perchlorate ($ClO_4^-$) removal. Water Research 2003, 37, (9), 2001-2012.
32. Westerhoff, P.; Yoon, Y.; Snyder, S.; Wert, E., Fate of endocrine-disruptor, pharmaceutical, and personal care product chemicals during simulated drinking water treatment processes. Environmental Science and Technology 2005, 39, (17), 6649-6663.
33. Yoon, Y.; Lueptow, R. M., Reverse osmosis membrane rejection for ersatz space mission wastewaters. Water Research 2005, 39, (14), 3298-3308.
34. Her, N.; Park, N.; Yoon, Y., Sonochemical enhancement of hydrogen peroxide production by $TiO_2$ coated glass beads. Chemical Engineering Journal 2011, 166, 184-190.
35. Her, N.; Park, J. S.; Yoon, J.; Sohn, J.; Lee, S.; Yoon, Y., Comparative study of sonocatalytic enhancement for removal of bisphenol A and 17 alpha-ethinyl estradiol. Industrial and Engineering Chemistry Research 2011, 50, (11), 6638-6645.
36. Park, N.; Her, N.; Yoon, Y., Sonochemical degradation of chlorinated phenolic compounds in water: physicochemical properties of compounds on degradation. Water, Air, and Soil Pollution 2011, 215, 585-593.
37. Yoon, Y.; Lueptow, R. A., Concentration of colloidal silica suspensions using fluorescence spectroscopy. Colloids and Surfaces a-Physicochemical and Engineering Aspects 2006, 277, (1-3), 107-110.
38. Joseph, L.; Zaib, Q.; Khan, I. A.; Berge, N. D.; Park, Y. G.; Saleh, N. B.; Yoon, Y., Removal of bisphenol A and 17 alpha-ethinyl estradiol from landfill leachate using single-walled carbon nanotubes. Water Research 2011, 45, (13), 4056-4068.
39. Park, J. S.; Her, N.; Oh, J.; Yoon, Y., Sonocatalytic degradation of bisphenol A and 17 alpha-ethinyl estradiol in the presence of stainless steel wire mesh catalyst in aqueous solution. Separation and Purification Technology 2011, 78, (2), 228-236.
40. Zheng, M.; Jagota, A.; Semke, E. D.; Diner, B. A.; McLean, R. S.; Lustig, S. R.; Richardson, R. E.; Tassi, N. G., DNA-assisted dispersion and separation of carbon nanotubes. Nature Materials 2003, 2, (5), 338-342.
41. Zheng, M.; Jagota, A.; Strano, M. S.; Santos, A. P.; Barone, P.; Chou, S. G.; Diner, B. A.; Dresselhaus, M. S.; McLean, R. S.; Onoa, G. B.; Samsonidze, G. G.; Semke, E. D.; Usrey, M.; Walls, D. J., Structure-based carbon nanotube sorting by sequence-dependent DNA assembly. Science 2003, 302, (5650), 1545-1548.
42. Islam, M. F.; Rojas, E.; Bergey, D. M.; Johnson, A. T.; Yodh, A. G., High weight fraction surfactant solubilization of single-wall carbon nanotubes in water. Nano Letters 2003, 3, (2), 269-273.
43. White, B.; Banerjee, S.; O'Brien, S.; Turro, N. J.; Herman, I. P., Zeta potential measurements of surfactant-wrapped individual single-walled carbon nanotubes. The Journal of Physical Chemistry C 2007, 111, (37), 13684-13690.
44. Saleh, N. B.; Pfefferle, L. D.; Elimelech, M., Aggregation kinetics of multiwalled carbon nanotubes in aquatic systems: measurements and environmental implications. Environmental Science and Technology 2008, 42, (21), 7963-7969.
45. Alpatova, A. L.; Shan, W.; Babica, P.; Upham, B. L.; Rogensues, A. R.; Masten, S. J.; Drown, E.; Mohanty, A. K.; Alocilja, E. C.; Tarabara, V. V., Single-walled carbon nanotubes dispersed in aqueous media via non-covalent functionalization: effect of dispersant on the stability, cytotoxicity, and epigenetic toxicity of nanotube suspensions. Water Research 2010, 44, (2), 505-520.
46. Hyung, H.; Kim, J. H., Natural organic matter (NOM) adsorption to multi-walled carbon nanotubes: Effect of NOM characteristic and water quality parameters. Environmental Science and Technology 2008, 42, 4416-4421.
47. Huang, Y.; Terentjev, E., Dispersion and rheology of carbon nanotubes in polymers. International Journal of Material Forming 2008, 1, (2), 63-74.
48. Hilding, J.; Grulke, E. A.; Zhang, Z. G.; Lockwood, F., Dispersion of carbon nanotubes in liquids. Journal of Dispersion Science and Technology 2003, 24, (1), 1-41.
49. Joseph, L.; Heo, J.; Park, Y. G.; Flora, J. R. V.; Yoon, Y., Adsorption of bisphenol A and 17 alpha-ethinyl estradiol on single walled carbon nanotubes from seawater and brackish water. Desalination 2011, 281, 68-74.
50. Senapati, S.; Mahon, A. R.; Gordon, J.; Nowak, C.; Sengupta, S.; Powell, T. H. Q.; Feder, J.; Lodge, D. M.; Chang, H.-C., Rapid on-chip genetic detection microfluidic platform for real world applications. Biomicrofluidics 2009, 3, 022407.
51. O'Connell, M. J., Carbon nanotubes: Properties and Applications. CRC Press: Boca Raton, Fla., 2006.

Example 4

Abstract

NanoGene assay is a magnetic bead and quantum dot nanoparticles based gene quantification assay. It relies on a set of probe and signaling probe DNAs to capture the target DNA via hybridization. We have demonstrated the inhibition resistance of the NanoGene assay using humic acids laden genomic DNA (gDNA). At about 1 µg humic acid per mL, quantitiative PCR (qPCR) was inhibited to 0% of its quantification capability whereas NanoGene assay was able to maintain more than 60% of its quantification capability. In order to further increase the inhibition resistance of NanoGene assay at high concentration of humic acids, we have identified the specific mechanisms that are responsible for the inhibition. We examined five potential mechanisms with which the humic acids can partially inhibit our NanoGene assay. The mechanisms examined were: (1) adsorption of humic acids on the particle surface; (2) particle aggregation induced by humic acids; (3) fluorescence quenching of quantum dots by humic acids during hybridization; (4) humic acids mimicking of target DNA; and (5) nonspecific binding between humic acids and target gDNA. The investigation showed that no adsorption of humic acids onto the particles' surface was observed for the humic acids' concentration. Particle aggregation and fluorescence quenching were also negligible. Humic acids also did not mimic the target gDNA except about 1000 µg humic acids per mL and hence should not contribute to the partial inhibition. Four above mechanisms were not related to the inhibition effect of humic acids particularly at the environmental relevant concentrations (<100 µg/mL). However a substantial amount of non-specific binding was observed between the humic acids and target gDNA. This possibly results in lesser amount of target gDNA being captured by the probe and signaling DNA.

Introduction

Gene quantification techniques such as fluorescent in-situ hybridization or quantitative polymerase chain reaction (qPCR) are widely used in environmental science and engineering to detect and quantify specific bacterial genes in environmental samples. Unfortunately these environmental samples also often contain humic compounds that can inhibit the quantification capability of these techniques. This significantly limits the use of these gene quantification techniques to field studies whose samples are not laden with humic compounds. Humic compounds such as humic acid, fulvic acid or humin are naturally occurring organic compounds that contain anionic functional groups (i.e., phenolic and carboxylic groups) as well as hydrophobic components (i.e., aromatic and aliphatic moieties)[1]. Humic compounds are known as the most commonly reported group of inhibitors in environmental samples. For the techniques based on DNA hybridization such as fluorescent in-situ hybridization, humic compounds appear to have deleterious effects on several reaction components and their interactions[2, 3]. They lower the efficiency in DNA-DNA hybridization[4, 5] and reduce the amount of DNA/RNA binding to membrane by occupying some of the nucleic acid binding sites on the membrane[6, 7].

The effect of humic compounds on the performance of PCR is well documented[8-11]. It was reported that 1 μL of humic acid-like extract was sufficient to inhibit a 100 μL reaction mix[12]. Several studies also showed that the humic impurities (<0.1 μg/mL) interfere with the interaction between target DNA and Taq polymerase, which is a key enzyme in PCR amplification[13-15]. The inhibitory effect of humic acids on qPCR assay may be due to the inhibition of Taq polymerase by humic acids[6, 7] and/or the complex formation of $Mg^{2+}$ ions, vital cofactor for Taq polymerase, with humic acids[12, 14]. Young et al. suggested that soil humic compounds possessed phenolic groups and they can either denature biological molecules via bonding with amides or oxidize to form a quinone which covalently binds to DNA or proteins[16]. Zipper et al. proposed several molecular mechanisms underlying the impact of humic acids on the fluorimetric assay using SYBR Green dye. They include inner filter effect, collisional quenching, and competitive binding between the dye and humic acids. The mechanisms are potentially responsible for the fluorescence quenching of the dye-DNA complex by humic acids[17]. Humic impurities are often co-extracted with nucleic acids from soil, sediment, and water samples[18]. Since extensive DNA purification does not ensure complete removal of humic compounds[9], it is necessary to enable and improve the inhibition resistance of gene quantification assays.

We have developed a nanoparticle based gene quantification (NanoGene) assay which is shown to be resistant to a number of environmental inhibitors[19]. It uses DNA hybridization with dual nanosize quantum dot (QD) labels and magnetic bead carrier[20]. The NanoGene assay captures the target genomic DNA (gDNA) via hybridization with two DNAs which are bound to a magnetic bead (MB) and fluorescent QDs. Magnetic separation is used to consolidate the captured target gene and fluorescence measurement is used for quantification.

Figure 25:
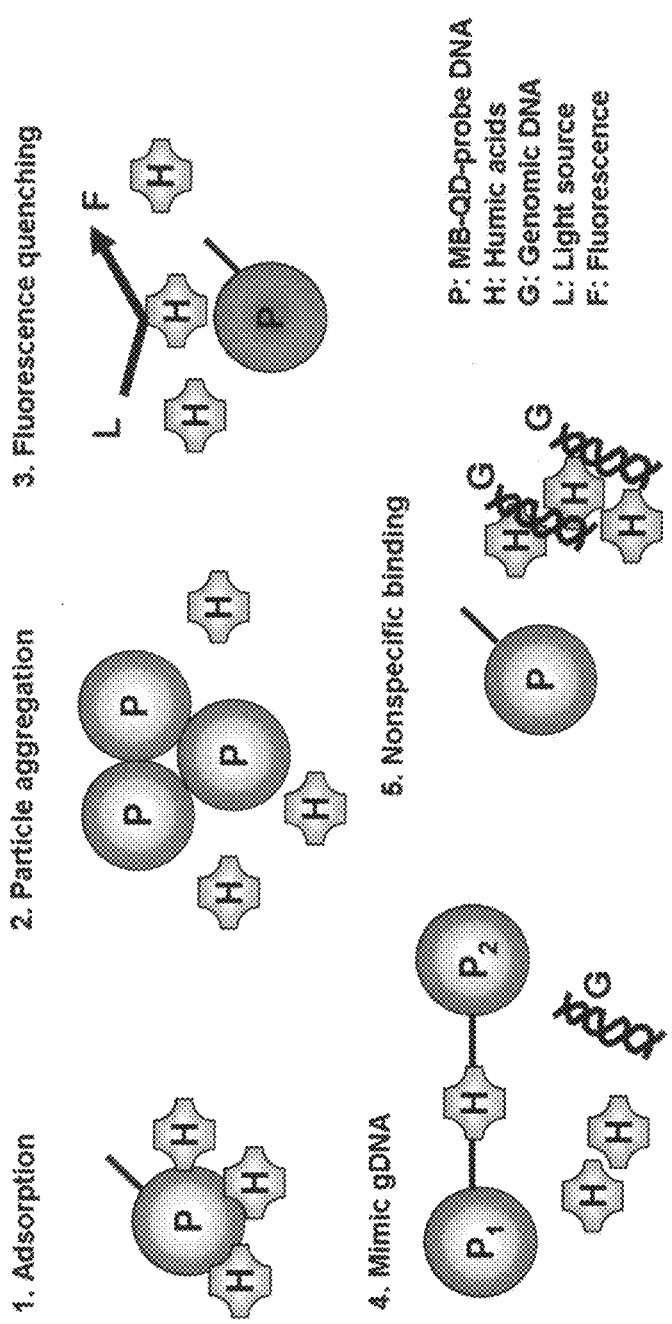
FIG. 25 illustrates the possible mechanisms of humic acids-resistance of the NanoGene assay. 1. Adsorption of humic acids on the particle surface, 2. Particle aggregation induced by humic acids, 3. Fluorescence quenching of QDs by humic acids during hybridization, 4. Humic acids mimicking target DNA, 5. Random nonspecific binding between humic acids and target gDNA. MB stands for magnetic beads and QD stands for quantum dot nanoparticles.

In the present disclosure, we specifically address the need for an inhibitor resistance gene quantification technique via in-depth characterization of the inhibition resistance of the NanoGene assay of the present disclosure to the presence of humic acids in test samples containing target gDNA. Using qPCR as a comparison, the quantification capability of the NanoGene assay was measured for various concentrations of humic acids (7 orders of magnitude) in the test samples. In addition, potential interactions between humic acids and the components of the assay were also investigated for their role in determining the performance of the assay. Without being bound by any particular theory, we believe that the following mechanisms are contributing to the observed inhibition: (1) adsorption of humic acids on the particle surface; (2) particle aggregation induced by humic acids; (3) fluorescence quenching of QDs by humic acids during hybridization; (4) humic acids mimic target DNA; and (5) random nonspecific binding between humic acids and target gDNA. The schematic of these is presented in FIG. 25.

Materials and Methods

NanoGene Assay.

The recent study by Kim and Son[20] describes the details of the NanoGene assay including its particle-particle and particle-DNA conjugates. The denatured form of target E. coli O157:H7 gDNA was hybridized with MB-$QD_{655}$-probe DNA and $QD_{565}$-signaling probe DNA in 400 μL DIG easy hybridization buffer (Roche Diagnostic, Basel, Switzerland) for about 12 h at about 37° C. using a gentle tilt rotation. After washing three times with phosphate buffer and its separation by a magnet (MPC®-96S, Invitrogen), the fluorescence of both QDs was measured by SpectraMax M2 microplate reader (MDS, Sunnyvale, Calif.). The fluorescence output was normalized ($QD_{565}/QD_{655}$). The quantification of target gene, eaeA gene of E. coli O157: H7, was performed in the absence and the presence of humic acids (Aldrich, St. Louis, Mo.). Gene copy numbers of gDNA were calculated based on the concentration of gDNA (ng/μL), gene sequences (151 bp), and molecular weight of each base (660 g/mol). Thus, gDNA of about 0.2-2.0 ng/μL is equivalent to about $8.0 \times 10^5$-$8.0 \times 10^6$ eaeA gene copies. A varying amount of humic acids (about 0.001-1000 μg/mL of reaction) were added. The environmentally relevant concentration range of humic acids is about 0.02-30 μg/mL[21]. The inhibition effect of humic acids was presented as the quantification capability (%), which was the output (i.e., fluorescence) of the assay performed with various amounts of humic acids divided by the output of assay without humic acids (no inhibition).

Quantitative PCR Assay.

The qPCR assay was used as a comparison in this study. The detailed procedure for qPCR[20] was described. In parallel to NanoGene assay, various amounts of humic acids were injected to the reaction with the gDNA in SYBR Green buffer (total volume of about 25 μL). The qPCR assay was performed using StepOne™ Real-Time PCR system (Applied Biosystems, Foster City, Calif.)[22]. The quantification capability (%) of qPCR was obtained in the same manner as that of the NanoGene assay.

Field Emission Scanning Electron Microscopy (FE-SEM).

The pattern of adsorbed humic acids on the particle conjugate of NanoGene assay was observed by FE-SEM (JSM-7000F, JEOL, Japan) after incubation. To simulate exposure to humic acids in test samples during hybridization, the MB-$QD_{655}$ particle conjugate was incubated with humic acids in two concentrations (about 100 and 1000 μg/mL) in the same manner as the hybridization of the NanoGene assay. The particle conjugate was subsequently dispersed in about 200 μL phosphate buffer (pH=about 7.4). About 5 μL of the samples were dispensed on carbon conductive tape (Electron Microscopy Sciences, Hatfield, Pa.) attached to and dried on the specimen holder (JEOL). The particle conjugate of NanoGene assay and humic molecules were observed by FE-SEM at an accelerating voltage of 20 kV.

Adsorption of Humic Acids on the Particles During Hybridization.

To quantify the adsorption of humic acids on the particle conjugates of NanoGene assay during hybridization, MB, MB-$QD_{655}$, and MB-$QD_{655}$-probe DNA (these particle conjugates will be referred to as MB-QD and MB-QD-DNA, respectively hereafter) were incubated in about 400 μL hybridization buffer containing humic acids for about 12 h.

The concentrations of humic acids used were about 0, 0.1, 1, 10, 100, and 1000 µg/mL. The particle reagents were subsequently isolated from the solution via magnetic separation. Supernatants were transferred to clear polystyrene 96-well plate (Nunc, Roskilde, Denmark) for absorbance measurement via SpectraMax M2 spectroscopy (MDS, Sunnyvale, Calif.) at $\lambda=332$ nm. The adsorbed amounts of humic acids on the particles were calculated by subtracting the absorbance of supernatant from the initial absorbance. The amounts (µg HA/mL/particle) of humic acids adsorbed on the particles were normalized by the absorbance of MB (measured at $\lambda=742$ nm). The remaining amounts of humic acids were statistically compared with initial amounts using a paired t test (n=3, two-tailed).

Particle Aggregation—Zeta Potential and Hydrodynamic Diameter.

The particles may aggregate in the presence of humic acids due to the influence from the various functional groups of humic acids. In order to examine the possibility of particle aggregation in the presence of humic acids, surface charge and hydrodynamic radii of the particles were observed in varying amounts of humic acids (about 0.001-1000 µg/mL). The pH change in solution was also monitored. The surface charges (i.e., zeta potential) of the particles were measured by Zetasizer nano ZS (Malven, UK) with laser Doppler anemometry with phase analysis light scattering in a capillary cell (750 µL, Malven). The dynamic viscosity of the hybridization buffer was determined as 2.6325 cP by the viscosity meter (GV 2200, Gilmont, Barrington, Ill.). The refractive index of the particles used is 1.5 for the measurements.

To estimate the particle aggregation, the size distribution of particles in solution was determined based on the hydrodynamic diameter of the particles. The hydrodynamic diameters were also measured by Zetasizer nano ZS with dynamic light scattering application using the same capillary cell. The measured particle size is the hydrodynamic radius of hydrated/solvated particle, including shape and surface roughness of particle and solvent molecules surrounding particle. All experiments were performed in triplicates and in each instance size of particle were measured ten times.

Quenching of Quantum Dots Fluorescence by Humic Acids.

The quenching effect of QD fluorescence by the presence of humic acids (about 0.001-1000 µg/mL) was investigated. The MB-QD particle conjugate was dispersed in about 200 µL of phosphate buffer and subsequently various concentrations of humic acids were added. The mixture of MB-QD particle conjugate and humic acids were transferred to a black 96-well plate for the fluorescence measurement ($\lambda_{em}=360$ nm, $\lambda_{ex}=660$ nm) to observe for potential collisional quenching effect. As compared to the control that contains no humic acids, the result would indicate the level of quenched fluorescence of samples that contained humic acids. The mixture of particles and humic acids were incubated for about 12 h and the UV-absorption analysis was performed to examine the static quenching effect.

Mimicking Target Genomic DNA.

The possibility of humic acids mimicking the target gDNA was examined by using humic acids instead of target gDNA in the hybridization process. Various amounts of humic acids (about 0.001-1000 µg/mL) including negative control (no humic acids) were added to the hybridization buffer containing MB-QD$_{655}$-probe DNA and QD$_{565}$-signaling probe DNA. The hybridization of humic acids with the probe and signaling probe DNA labeled with MB-QD$_{655}$ and QD$_{565}$, respectively, was determined by measuring the normalized fluorescence (QD$_{565}$/QD$_{655}$).

Nonspecific Binding Between Humic Acids and Genomic DNA (Passive Adsorption).

To examine the nonspecific binding between humic acids and gDNA, humic acids encapsulated MBs were incubated with various amounts of gDNA. Humic acids encapsulated MBs were prepared by adding about 5 µg of humic acids to MBs (about $2 \times 10^7$ beads) and incubated with coupling agents for covalent bonding (i.e., EDC and NHS) at about ambient temperature. After about 2 h, the humic acids coated MBs were separated by a magnet and washed three times with phosphate buffer. The humic acids coated MBs were subsequently dispersed in buffer and transferred to a clear polystyrene 96-well plate. The amount of humic acids used for the encapsulation of MBs was determined to be about 2.5 µg per $2 \times 10^7$ MBs based on the absorbance at 430 nm. The coated MBs were incubated with various amounts of gDNA (about 0.01-2.0 ng per µL of reaction) in hybridization buffer at about 37° C. with a slow tilt rotation. After about 12 h, the particle conjugates were separated by magnetic field. The amount of gDNA that was not adsorbed on the particles was isolated by centrifugation. The supernatants were collected to measure the residual amount of gDNA by absorbance at 260 nm. The amount of nonspecifically bound gDNA, resulting from the passive adsorption, was obtained by subtracting the gDNA in the supernatant from the prior gDNA applied.

Results and Discussion

Resistance of NanoGene Assay to Humic Acids.

The quantification capability (%) of the NanoGene assay was not completely inhibited by the presence of humic acids (FIG. 26a). But the quantification capability of qPCR reduced to 0% over about 1 µg/mL humic acids, although it maintained 90% at about 0.1 µg/mL humic acids (FIG. 26b). The output (fluorescence) of NanoGene assay slightly decreased at the high concentration of humic acids, however it maintained the gene quantification capability more than 50% at all concentration ranges of humic acids (about 0.001-1000 µg/mL) and target gDNA. Note the range of environmental relevant concentration of humic acids is 0.02-30 µg/mL. Therefore quantification of raw environmental samples using qPCR assay may not be plausible because the inhibition is very significant and the result will show no signals over about 1 µg/mL humic acids. In order to further increase the inhibition resistance of NanoGene assay at high humic acid concentrations, we identified the specific mechanisms that are responsible for the inhibition as described in FIG. 25.

Adsorption of Humic Acids on the Particles.

Figure 27A:
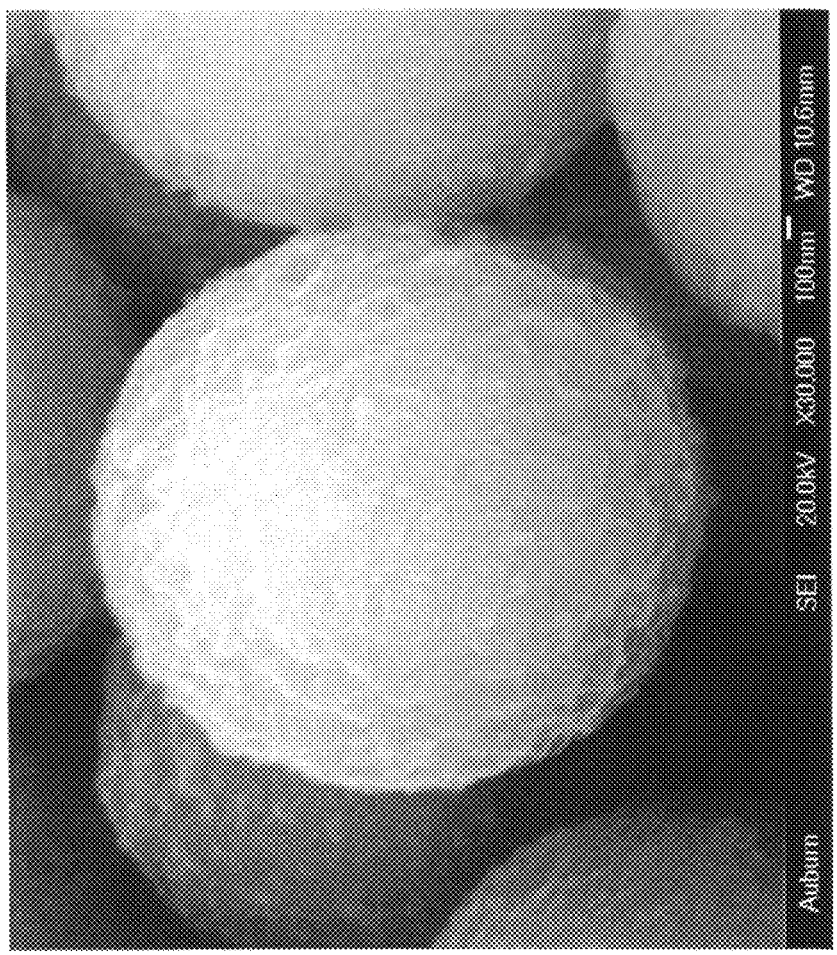
FIGS. 27A-C are FE-SEM images of MB-QDs (A) without humic acids, (B) with 100 µg/mL humic acids and (C) 1000 µg/mL humic acids. The locations of putative humic molecules are indicated by the arrows. The scale bar represents 100 nm.
Figure 27B:
Figure 27C:

FE-SEM analysis was performed to visualize the interaction of humic acids with the components (MB-QD) of NanoGene assay. As shown in FIG. 27, the humic molecules were observed as a coagulated pattern and resided on the surface of MB-QD at higher concentrations (about 100 and 1000 µg/mL). It was reported that the humic molecules can be held together in supramolecular conformations by weak hydrophobic bond at neutral and alkaline pH[23]. Since humic substances have both hydrophobic and hydrophilic functional groups (i.e., amphiphilic), they can form aggregates which have the hydrophobic interior with the highly charged exterior[24] and resides on the particle surface. However, the amount of information that can be derived from the image pertaining to the interactions (e.g., quantitative data of adsorption) between humic acids and MB-QD is limited. Therefore, we performed the following experiment in order to measure the adsorption of humic acids on the surface of particles. During DNA hybridization, humic acids may be adsorbed on the components of NanoGene assay. Therefore, it causes the interruption of DNA hybridization and further gene quantification of assay. Various amounts of humic acids were incubated with the particles (i.e., MB, MB-QD, and MB-QD-DNA) under hybridization condition to examine the adsorption of humic acids. Table 1 shows the amounts of adsorbed humic acids on the particles. No humic acids were adsorbed on the particles at lower concentrations (about <10 μg/mL of reaction), and a slight adsorption occurred at higher concentrations (about 10-1000 μg/mL). To determine the degree of humic acids adsorption at higher concentrations, the initial amount (μg/mL) and remaining (the initial amount–the adsorbed amount) portion of humic acids were compared using the paired t test. All tests were non-significant ($P>0.01$, $n=3$). In other words, there was no significant adsorption of humic acids throughout all the concentration applied (about 0.1-1000 μg/mL) on all particles tested: MB, MB-QD and MB-QD-DNA particle complex.

Figure 32:
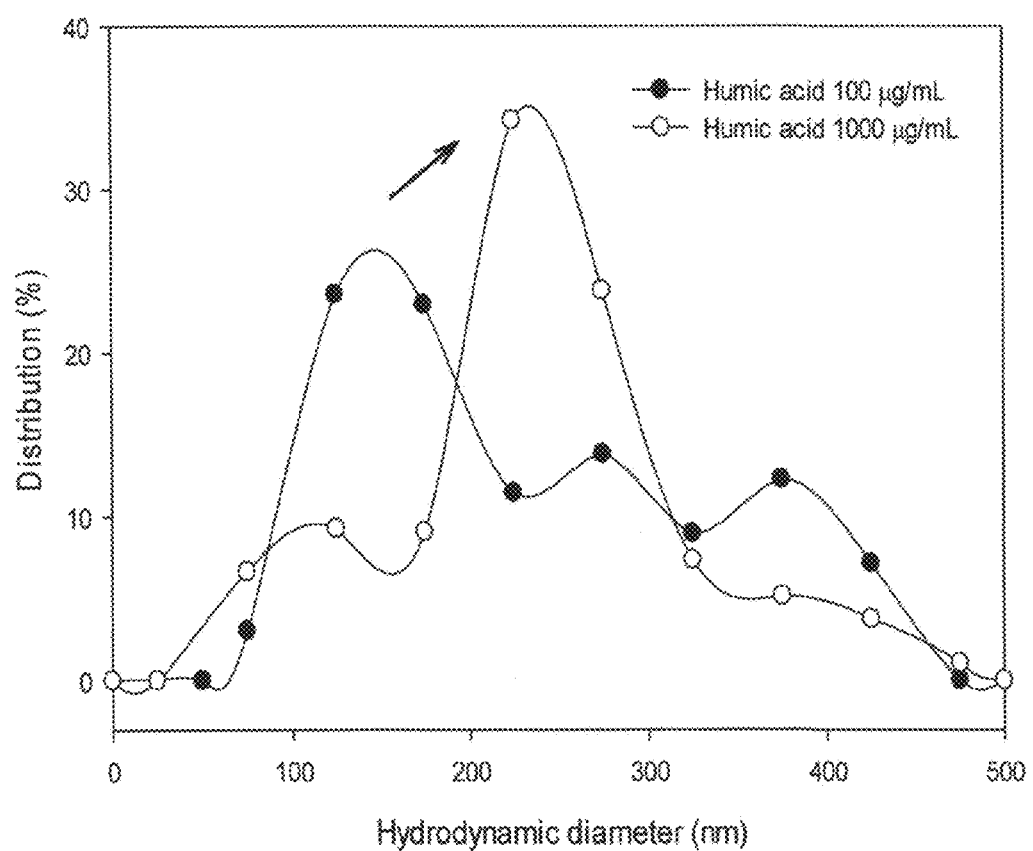
FIG. 32 is a graph that illustrates the hydrodynamic diameter distribution of coagulated humic acids with no particles involved. The size peak was shifted higher (depicted by the arrow) as the concentration of humic acids increases. It indicates the strong tendency of humic acids to coagulate.

FIG. 32 shows the shift of size distribution of humic acids molecules at different concentrations of humic acids. The size of the most abundant humic molecules increased from 150 to 250 nm as humic acids increased from 100 to 1000 μg/mL. Increasing concentration of humic acids induces the formation of humic coagulants instead of particle aggregation. It suggests that the binding affinity between humic acids is stronger (at least identical) than the interaction between humic acids and particles.

Fluorescence Quenching of Quantum Dots by Humic Acids.

To examine the fluorescence quenching effect of humic acids, the fluorescence of MB-QD in the presence of various humic acids was measured. The relative fluorescence intensities of samples were calculated based on the assumption

TABLE 1

The adsorption of humic acids on the particle complex of NanoGene assay:
(a) MB, (b) MB-QD, and (c) MB-QD-DNA.

| Humic acids (μg/mL) | MB Adsorbed (μg HA/mL/particle) | P-value | MB-QD Adsorbed (μg HA/mL/particle) | P-value | MB-QD-DNA Adsorbed (μg HA/mL/particle) | P-value |
|---|---|---|---|---|---|---|
| 0 | 0.0 | — | 0.0 | — | 0.0 | — |
| 0.1 | 0.0 | — | 0.0 | — | 0.0 | — |
| 1 | 0.0 | — | 0.0 | — | 0.0 | — |
| 10 | 0.34 ± 0.31 | 0.2244 | 0.05 ± 0.08 | 0.4226 | 0.0 | — |
| 100 | 4.24 ± 3.26 | 0.1538 | 2.31 ± 2.07 | 0.2018 | 3.34 ± 4.20 | 0.2811 |
| 1000 | 21.98 ± 7.67 | 0.0205 | 22.66 ± 21.77 | 0.2138 | 31.49 ± 5.57 | 0.0192 |

Particle Aggregation: Surface Charge and Particle Size Distribution.

We believe the particle complexes may aggregate in the presence of humic acids, as humic acids have various functional groups. In order to investigate particle aggregation, particle size distribution was determined using dynamic light scattering spectroscopy. FIG. 28a shows the hydrodynamic diameter measurement of the particles (i.e., MB, MB-QD, and MB-QD-DNA). The diameter of particles (FIG. 28a) was approximately 4 μm regardless of various amount of humic acids and the particle combinations. The particle size was uniform and less than about 5.6 μm (depicted by the line in FIG. 28a), which is twice of MB's diameter. The result showed that no significant particle aggregation was induced by humic acids.

The stability of particle dispersion in the presence of humic acids was also investigated. The stability of particles in solution decreases as the particle aggregation occurs due to charge neutralization. Surface charge values $>±30$ mV indicates well dispersed particles with no aggregation[25]. In the absence of humic acids (negative control), the surface charges of particle conjugates were around—60 mV. As shown in FIG. 28b, the surface charges of all three particle conjugates were approximately—60 mV over the range (about 0.001-1000 μg/mL) of humic acids used in the experiment. This meant no aggregation of particles occurred in the presence of humic acids. In other words, the humic acids do not function as the bridge between particles for further coagulation. In addition, the pH was maintained at about 7.4 without being affected by the amount of humic acids.

Figure 29A:
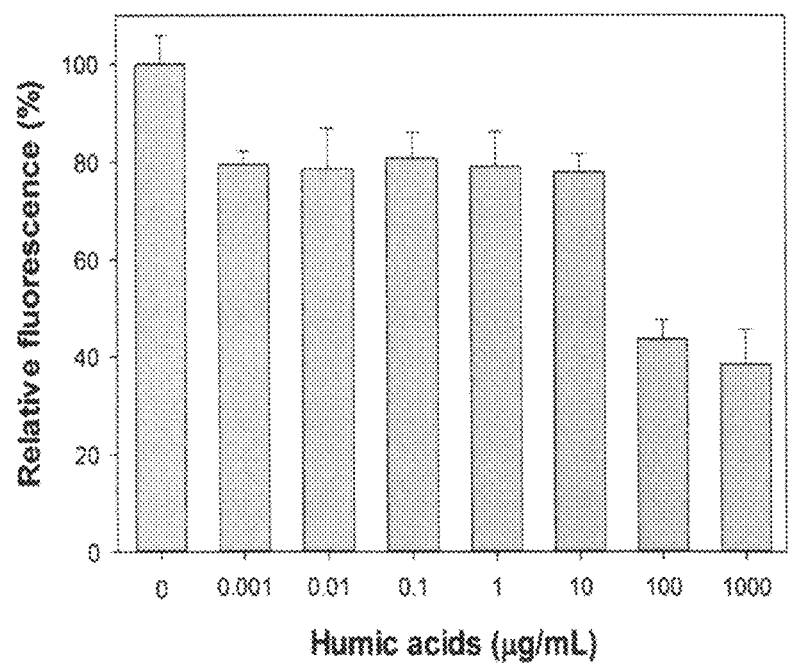
FIGS. 29A-B are graphs that illustrate fluorescence quenching effects by humic acids. (A) Collisional quenching: fluorescence intensity of MB-$QD_{655}$ with various concentrations of humic acids. (B) Static quenching: UV-vis absorbance spectra of MB-$QD_{655}$ incubated with varying humic acids (0.001-1000 µg/mL).

As the concentration of humic acids increases, humic acids may coagulate by clumping with each other instead of interacting with particles. In this regard, we have also determined the size distribution with humic acids only without the particle conjugates. The result showed that increasing humic acids caused the increased coagulation of humic molecules.

that the initial fluorescence intensity of MB-QD in the absence of humic acids was 100%. As shown in FIG. 29a, the fluorescence intensity of MB-QD was sustained at 80% of its initial value when exposed to humic acids concentration range from about 0.001 to 10 μg/mL. However, at the higher concentration of humic acids (about 100 and 1000 μg/mL), the fluorescence decreased to about 40%. One way ANOVA test indicated that the relative fluorescence (%) at higher concentrations of humic acids was significantly different ($P<0.05$, $n=16$). This observation is consistent with the earlier finding that humic acids at higher concentrations tend to coagulate each other as shown in both FIGS. 27 and 32. The coagulation of humic acids may result in erroneous fluorescence measurement of QD particle. In addition, the probability of collisional encounters between humic acids and particles increases with higher concentration of humic acids. The collision between humic acids and MB-QD may generate the loss of excitation energy in the form of heat instead of photon emission (fluorescence), resulting in the decrease of the MB-QD fluorescence. This loss in fluorescence is known as collisional (or dynamic) quenching. The collisional quenching is the interaction of transient excited state and does not affect the absorption spectrum[17, 26].

Figure 29B:
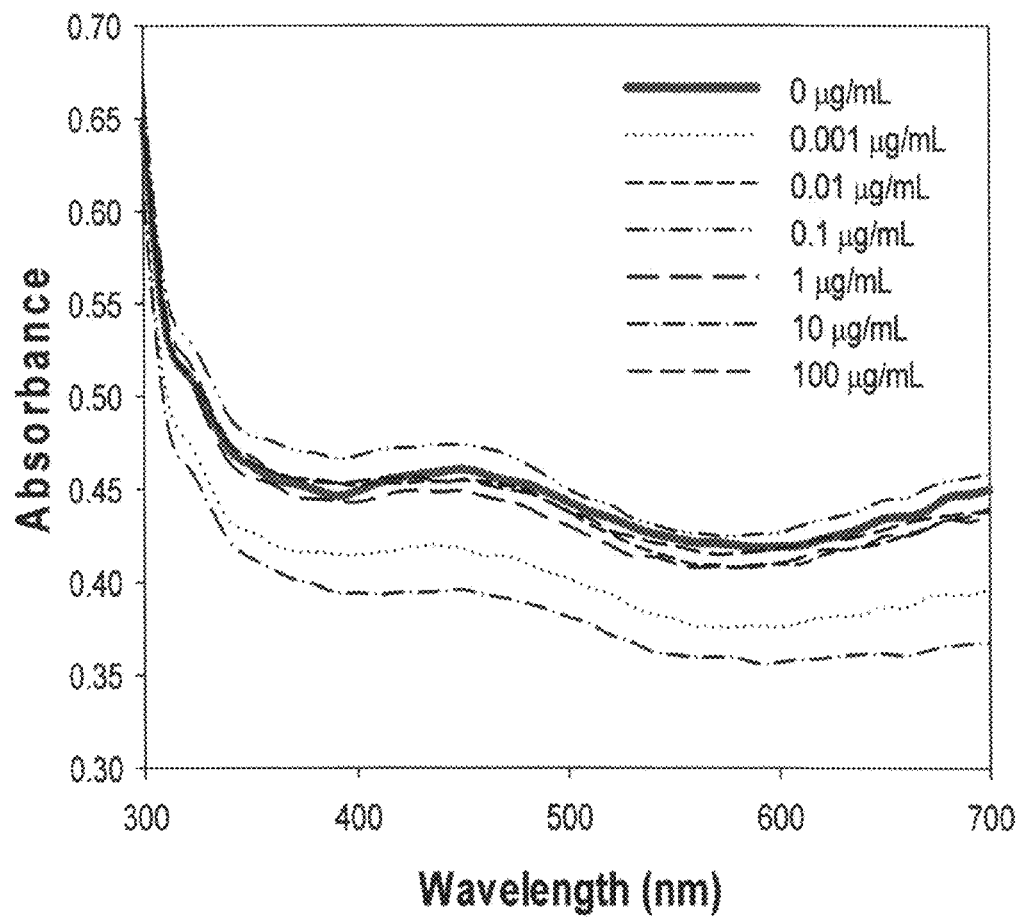

In the other hand, the interaction of the fluorophore with quencher can form a non-fluorescent complex, resulting in static quenching. Since the complex may have a different spectrum from the fluorophore, the change of absorption spectra would indicate static quenching[26]. As a result of UV-vis absorbance scanning, no peak shift was observed in the absorption spectrum of MB-QD incubated with various concentrations of humic acids relative to the absence of humic acids (FIG. 29b). The spectra of negative control (no humic acids), which is depicted as a thick line in FIG. 29b, showed a similar pattern for all tested samples over the entire concentration range of humic acids. One way ANOVA was used to test the significance of the absorbance peak shift. The ANOVA result showed no significant difference (P>0.05, n=7) between the wavelengths for the absorbance peak for all the samples tested. In other words, the presence of humic acids did not affect the optical characteristic of MB-QD by creating other complexes which would be represented by peaks in absorption spectra. This indicated that no static quenching occurred between humic acids and particle complex.

Humic Acids Mimicking Target Genomic DNA.

Figure 30:
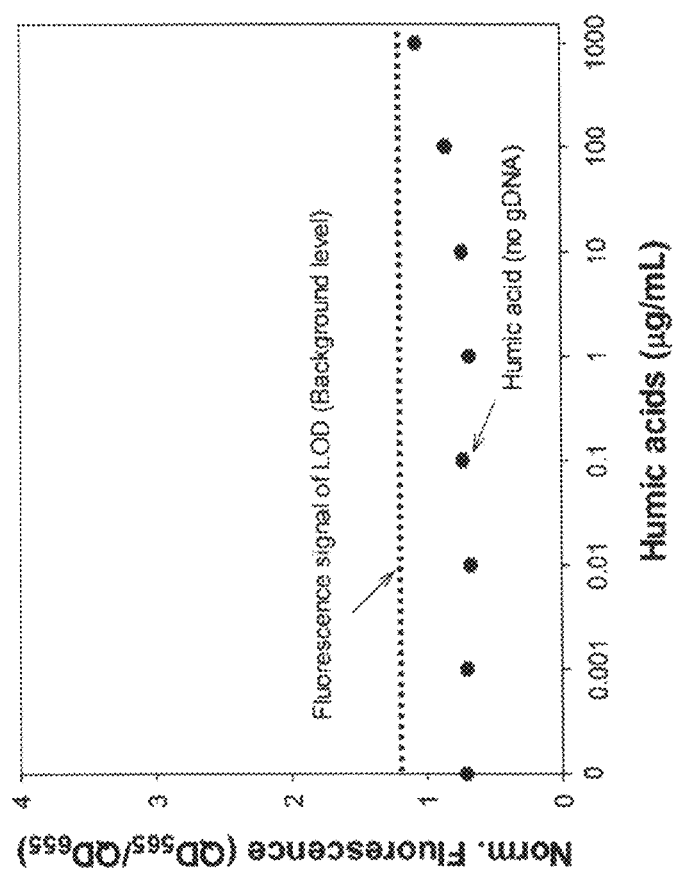
FIG. 30 is a graph that illustrates the mimicking effect of humic acids.

The possibility of humic acids mimicking target gDNA was examined by incubating the particles with humic acids instead of target gDNA. FIG. 30 shows the normalized fluorescence obtained by the hybridization of humic acids with the probe DNAs. The DNA hybridization in the NanoGene assay was carried out using humic acids in place of target gDNA. In the event that the humic acids mimic target gDNA, fluorescence ($QD_{565}/QD_{655}$) will be detected as a result of the hybridization between humic acids and probe/signaling probe DNAs. However, all the signals (FIG. 30) were lower than the background level (1.17 RFU) and it is the limit of detection of the NanoGene assay[20]. All the signals, except 1000 μg/mL (P>_0.05, n=7), were significantly different from the limit of detection (P<0.05, n=7, Student's t-test). Thus, the humic acids except 1000 μg/mL did not mimic the target gDNA and no hybridization would occur between humic acids and probe/signaling DNAs.

Nonspecific Binding Between Humic Acids and Target Genomic DNA.

Figure 31A:
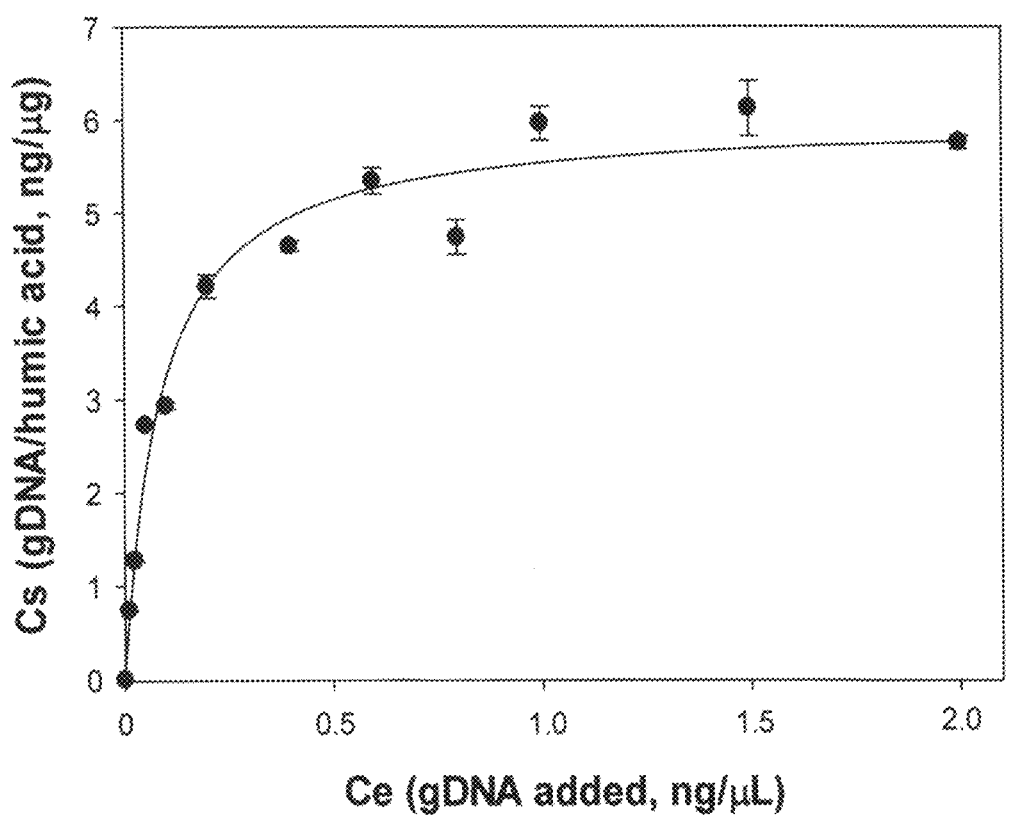
FIGS. 31A-B are graphs that illustrate nonspecific binding of gDNA and humic acids via passive adsorption. (A) The adsorption isotherm of gDNA on the humic acids-encapsulated MB. (B) Relative gene quantity that are obtained as a function of gDNA (0.4, 1, 2 ng/µL).

Adsorption test was used to investigate the degree of nonspecific binding between humic acids and target gDNA. FIG. 31a shows the adsorption isotherm of target gDNA on the surface of humic acids encapsulated MB. $C_e$ in y-axis indicates the mass of target gDNA over the mass of humic acids (ng/μg) and $C_e$ in x-axis indicates the concentration of target gDNA added (ng/μL), where the volume is the reaction volume of the assay. The adsorbed amount of target gDNA per unit amount of humic acids on MBs increased initially and reached a plateau value (5.5 ng/μg). The adsorption isotherm of target gDNA onto the humic acids coated on MBs was fitted using the Langmuir equation (eq. 1):

$$q = \frac{q_{max} K_A C}{1 + K_A C} \quad (\text{eq. 1})$$

where q=the adsorbed target gDNA concentration (ng gDNA/μg humic acids on MBs), $q_{max}$=the maximum concentration of adsorbed target gDNA, $K_A$=constant, and C=the residual concentration of target gDNA in solution. The constants $K_A$ and $q_{max}$ were evaluated from the linearized form represented by the eq. 2:

$$\frac{1}{q} = \frac{1}{q_{max} K_A} \frac{1}{C} + \frac{1}{q_{max}} \quad (\text{eq. 2})$$

A plot of 1/q against 1/C gives a straight line with a slope of $1/(q_{max} K_A)$ and an intercept of $1/q_{max}$. The correlation coefficient ($R^2$) describing the goodness of fit to the linearized Langmuir model was 0.99. The $q_{max}$ and $K_A$ were 5.71 (ng/μg) and 1.50×10⁻², respectively. This means a maximum of about 5.71 ng of gDNA can be adsorbed by about 1 μg of humic acids (bounded on MBs).

The binding between target gDNA and humic acids is likely due to passive adsorption. Passive adsorption can occur via the combination of both electrostatic and hydrophobic interactions. Humic acids have various hydrophilic functional groups as well as hydrophobic center. Similarly gDNA has hydrophilic groups such as amine and phosphate as well as hydrophobic impurities such as proteins. Since humic acids contain organic groups with variable aromaticity, the hydrophobic part of humic acids may attract the hydrophobic impurities of gDNA. In addition, the phenolic groups of humic substances can also denature biological molecules by forming amide bonds or oxidizing to form a quinone which covalently bonds to DNA or proteins[6, 16]. These various functional sites may induce the nonspecific binding between gDNA and humic acids.

Figure 31B:
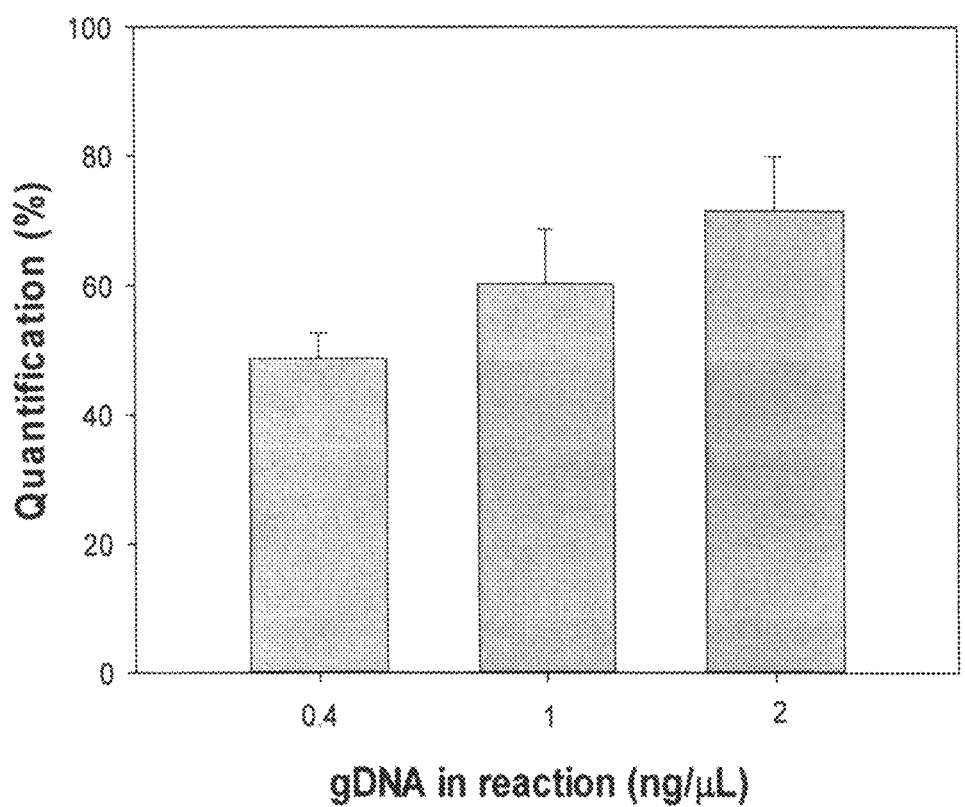

To further examine the nonspecific binding between gDNA and humic acids, additional quantification experiment (NanoGene assay) was performed with test samples containing varying amounts of gDNA and the same amount of humic acids (about 1 μg/μL: the highest humic acids concentration (about 1000 μg/mL) in the previous graphs). As shown in FIG. 31b, as the amount of gDNA increases, the quantification capability (percentage) of the NanoGene assay also increases. This observation is consistent with the belief that humic acids compete with the NanoGene assay components to bind with the gDNA via non-specific binding. In addition, the results showed that the humic acids were able to bind a larger absolute amount, but lower overall percentage, of the gDNA at a higher gDNA concentration. Therefore, it is indicative that the binding efficiency between humic acids and gDNA is on the same order of magnitude as that between components of NanoGene assay (MB-QDs) and gDNA.

In order to mitigate inhibition via non-specific binding between humic acids and gDNA, the binding efficiency between MB-QDs and gDNA can be increased via increasing the concentration of MB-QDs. Another mitigation strategy involves the use of the additional interceptor molecules (e.g., polymers), which can preferably bind with humic acids, prior to the quantification. The interceptor molecule will be chosen such that it will not bind to the MB-QDs. In this way, the humic acids in the sample will be bound to the interceptor molecule and therefore unable to further bind to the target gDNA. These methods are reasonable propositions because the binding efficiency between gDNA and the competing humic acids and MB-QDs are in the same order of magnitude.

In summary, we have demonstrated the inhibition resistance of NanoGene assay of the present disclosure to the presence of humic acids in test samples for concentration as high as about 10 μg humic acid per mL. At this concentration, the NanoGene assay was able to maintain more than about 60% of its quantification capability. The four following mechanisms: 1) adsorption of humic acids on the particles; 2) particle aggregation by humic acids; 3) fluorescence quenching by humic acids; and 4) binding between probe DNA and humic acids, did not show significant contribution to the inhibition effect of humic acids particularly at the environmental relevant concentrations (about <100 μg/mL). However substantial nonspecific binding (adsorption) between target gDNA and humic acids was observed. The adsorption may be attributed to the amphiphilic structures of both humic acids and gDNA. The present disclosure includes evidence of nonspecific binding as the mechanism by which humic acids can inhibit DNA hybridization in the NanoGene assay.

REFERENCES

Which are Herein Incorporated by Reference

1. Stumm, W.; Morgan, J. J., *Aquatic chemistry, chemical equilibria and rates in natural waters*. John Wiley & Sons, Inc.: New York, N.Y., 1996.

2. Jacobsen, C. S.; Rasmussen, O. F., Development and application of a new method to extract bacterial DNA from soil based on separation of bacteria from soil with cation-exchange resin. *Appl. Environ. Microbiol.* 1992, 58, 2458-2462.
3. Wilson, I. G., Inhibition and facilitation of nucleic acid amplification. *Appl. Environ. Microbiol.* 1997, 63, (10), 3741-3751.
4. Steffan, R. J.; Goksoyr, J.; Bej, A. K.; Atlas, R. M., Recovery of DNA from soils and sediments. *Appl. Environ. Microbiol.* 1988, 54, (12), 2908-2915.
5. Tijssen, P., *Hybridization with nucleic acid probes, part I: theory and nucleic acid precipitation.* Elsevier Science Publishers B.V.: Amsterdam, The Netherlands, 1993.
6. Alm, E. W.; Zheng, D.; Raskin, L., The presence of humic substances and DNA in RNA extracts affects hybridization results. *Appl. Environ. Microbiol.* 2000, 66, 4547-4554.
7. Bachoon, D. S.; Otero, E.; Hodson, R. E., Effects of humic substances on fluorometric DNA quantification and DNA hybridization. *J. Microbiol. Methods* 2001, 47, 73-82.
8. Chandler, D. P.; Schreckhise, R. W.; Smith, J. L.; Jr., H. B., Electroelution to remove humic compounds from soil DNA and RNA extracts. *J. Microbiol. Methods* 1997, 28, 11-19.
9. Zhou, J.; Bruns, M. A.; Tiedje, J. M., DNA recovery from soils of diverse composition. *Appl. Environ. Microbiol.* 1996, 62, 316-322.
10. Ogram, A.; Sayler, G. S.; Barkay, T., The extraction and purification of microbial DNA from sediments. *J. Microbiol. Methods* 1987, 7.
11. Porteus, L. A.; Armstrong, J. L., Recovery of bulk DNA from soil by a rapid, small-scale extraction method. *Curr. Microbiol.* 1991, 22, 345-348.
12. Tsai, Y.-L.; Olson, B. H., Detection of low numbers of bacterial cells in soils and sediments by polymerase chain reaction. *Appl. Environ. Microbiol.* 1992, 58, (2), 754-757.
13. Tebbe, C. C.; Vahjen, W., Interference of humic acids and DNA extracted directly from soil in detection and transformation of recombinant DNA from bacteria and a yeast. *Appl. Environ. Microbiol.* 1993, 59, 2657-2665.
14. Tsai, Y.-L.; Olson, B. H., Rapid method for separation of bacterial DNA from humic substances in sediments for polymerase chain reaction. *Appl. Environ. Microbiol.* 1992, 58, 2292-2295.
15. McGregor, D. P.; Forster, S.; Steven, J.; Adair, J.; Leary, S. E. C.; Leslie, D. L.; Harris, W. J.; Titball, R. W., Simultaneous detection of microorganisms in soil suspension based on PCR amplification of bacterial 16S rRNA fragments. *Biotechniques* 1996, 21, 463-471.
16. Young, C.; Burghoff, R. L.; Keim, L. G.; Minak-Bernero, V.; Lute, J. R.; Hinton., S. M., Polyvinylpyrrolidone-agarose gel electrophoresis purification of polymerase chain reaction-amplifiable DNA from soils. *Appl. Environ. Microbiol.* 1993, 59, 1972-1974.
17. Zipper, H.; Buta, C.; Lammle, K.; Brunner, H.; Bernhagen, J.; Vitzthum, F., Mechanisms underlying the impact of humic acids on DNA quantification by SYBR Green I and consequences for the analysis of soils and aquatic sediments. *Nucleic Acids Res.* 2003, 31, (7), e39.
18. Jackson, C. R.; Harper, J. P.; Willoughby, D.; Roden, E. E.; Churchill, P. F., A simple, efficient method for the separation of humic substances and DNA from environmental samples. *Appl. Environ. Microbiol.* 1997, 63, 4993-4995.
19. Kim, G.-Y.; Wang, X.; Son, A., Inhibitor resistance and in-situ capability of nanoparticle based gene quantification. *J. Environ. Monit.* 2011, 13, 1344-1350.
20. Kim, G.-Y.; Son, A., Development and characterization of a magnetic bead-quantum dot nanoparticles based assay capable of *Escherichia coli* O157:H7 quantification. *Analytica Chimica Acta* 2010, 677, 90-96.
21. Brum, M. C.; Oliveira, J. F., Removal of humic acid from water by precipitate flotation using cationic surfactants. *Miner. Eng.* 2007, 20, 945-949.
22. Carey, C. M.; Kostrzynska, M.; Thompson, S., *Escherichia coli* O157:H7 stress and virulence gene expression on Romaine lettuce using comparative real-time PCR. *J. Microbiol. Methods* 2009, 77, (2), 235-242.
23. Osterberg, R.; Lindovist, I.; Mortensen, K., Particle size of humic acid. *Soil Sci Soc Am J* 1993, 57, 283-285
24. Wershaw, R. L., Model for humus in soils and sediments. *Environ. Sci. Technol.* 1993, 27, 814-816.
25. Zeta potential of colloids in water and waste water, A. S. D.-., American Society for Testing and Materials, 1985
26. Lakowicz, J. R., Fluorescence quenching: theory and applications. 1991, 2nd ed. Kluwer Academic/Plenum, N.Y., N.Y.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of the disclosure. Many variations and modifications may be made to the above-described embodiments. All such modifications and variations are intended to be included herein within the scope of this disclosure and protected by the following claims.

Therefore, at least the following is claimed:

1. A method of analyzing a target in a sample comprising:
contacting the sample with a capturing probe DNA conjugated to both a magnetic bead (MB) and a first quantum dot (QD) and further contacting the sample with a signaling probe DNA covalently labeled with a second QD;
hybridizing a target with the capturing probe and the signaling probe DNA to a target to form a hybridized target, wherein the target is selected from the group consisting of: a single wall carbon nanotube (CNT), a multi-wall CNT, a genomic substance, a single strand DNA, a double strand DNA, and a combinations thereof;
separating the hybridized target using a magnetic field; and
quantifying the target by measuring the ratio of light emission from the second QD to the light emission from the first QD, wherein the method is resistant to an inhibitory substance and/or an interference substance present in the sample or introduced during performance of the method.

2. The method of claim 1, wherein the method is performed at least about room temperature.

3. The method of claim 1, wherein the sample is selected from the group consisting of: a purified sample and an unpurified sample.

4. The method of claim 3, wherein the unpurified sample comprises interference and inhibitory substances selected from the group consisting of: an organic compound, a non-target genomic substance, a non-target DNA, a humic acid, a mineral, an ion, a carbon chemistry based compound, graphene, a residual reagent, and a combination thereof.

5. The method of claim 1, wherein the first QD and second QD each comprises comprising a photo emission stable materials, wherein the materials fluoresce when excited.

6. The method of claim 5, wherein the photo emission stable materials comprise quantum dots.

7. The method of claim 1, wherein a geometry of the MB is selected from the group consisting of: a two-dimensional geometry, a three-dimensional geometry, and a combination thereof.

8. The method of claim 7, wherein the two-dimensional geometry is selected from the group consisting of: a flat disc, a flat square, a flat irregular shape, and a combination thereof.

9. The method of claim 7, wherein the three-dimensional geometry is selected from the group consisting of: a sphere, a block, and a combination thereof.

* * * * *